US012005259B2

(12) United States Patent
Yoon et al.

(10) Patent No.: US 12,005,259 B2
(45) Date of Patent: Jun. 11, 2024

(54) DUAL SENSORS TO CONTROL PACING RATE

(71) Applicant: Medtronic, Inc., Minneapolis, MN (US)

(72) Inventors: Hyun J. Yoon, Vadnais Heights, MN (US); Vincent P. Ganion, Blaine, MN (US); Yanina Grinberg, Plymouth, MN (US); Saul E. Greenhut, Denver, CO (US); Todd J. Sheldon, North Oaks, MN (US); Paul R. Solheim, Blaine, MN (US); Eric R. Williams, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 124 days.

(21) Appl. No.: 17/404,517

(22) Filed: Aug. 17, 2021

(65) Prior Publication Data

US 2022/0072316 A1 Mar. 10, 2022

Related U.S. Application Data

(60) Provisional application No. 63/076,420, filed on Sep. 10, 2020.

(51) Int. Cl.
*A61N 1/365* (2006.01)
*A61N 1/362* (2006.01)
(52) U.S. Cl.
CPC ....... *A61N 1/36542* (2013.01); *A61N 1/3622* (2013.01); *A61N 1/3624* (2013.01); *A61N 1/3655* (2013.01)

(58) Field of Classification Search
CPC .............. A61N 1/36542; A61N 1/3655; A61N 1/36585
See application file for complete search history.

(56) References Cited

U.S. PATENT DOCUMENTS

| 4,485,813 | A |    | 12/1984 | Anderson et al.        |
|-----------|---|----|---------|------------------------|
| 4,543,954 | A |    | 10/1985 | Cook et al.            |
| 4,782,836 | A | *  | 11/1988 | Alt ............ A61N 1/3655 607/19 |

(Continued)

FOREIGN PATENT DOCUMENTS

EP      2599523 B1    10/2016

OTHER PUBLICATIONS

Dell'Orto, et al., "Sensors for Rate Responsive Pacing," In the Indian Pacing and Electrophysiology Journal (ISSN 0972-6292), 4(3): pp. 137-145, 2004, 9 pages.

(Continued)

*Primary Examiner* — George R Evanisko

(57) ABSTRACT

A medical device is configured to generate an acceleration signal and a temperature signal. The device is configured to determine an activity metric from the acceleration signal that is representative of patient physical activity. In response to determining that the activity metric is equal to or greater than a previously determined activity metric, the device is configured to adjust a target cardiac pacing rate based at least on a temperature change determined from the temperature signal. The device may include a pulse generator for generating cardiac pacing pulses based on the target cardiac pacing rate.

25 Claims, 18 Drawing Sheets

(56) References Cited

U.S. PATENT DOCUMENTS

| | | | |
|---|---|---|---|
| 4,926,863 A * | 5/1990 | Alt | A61N 1/36542 607/18 |
| 5,005,574 A | 4/1991 | Fearnot et al. | |
| 5,052,388 A | 10/1991 | Sivula et al. | |
| 5,360,436 A * | 11/1994 | Alt | A61N 1/36542 607/18 |
| 5,507,782 A | 4/1996 | Kieval et al. | |
| 5,562,711 A | 10/1996 | Yerich et al. | |
| 5,593,431 A | 1/1997 | Sheldon | |
| 5,885,471 A | 3/1999 | Ruben et al. | |
| 6,044,297 A | 3/2000 | Sheldon et al. | |
| 6,249,700 B1 | 6/2001 | Alt | |
| 6,449,508 B1 | 9/2002 | Sheldon et al. | |
| 7,130,681 B2 | 10/2006 | Gebhardt et al. | |
| 7,937,148 B2 | 5/2011 | Jacobson | |
| 8,255,051 B2 * | 8/2012 | Cholette | A61B 5/01 607/18 |
| 8,543,205 B2 | 9/2013 | Ostroff | |
| 8,731,662 B2 | 5/2014 | Imran | |
| 9,168,383 B2 | 10/2015 | Jacobson et al. | |
| 9,833,624 B2 | 12/2017 | Chin et al. | |
| 10,207,116 B2 | 2/2019 | Sheldon et al. | |
| 10,315,036 B2 | 6/2019 | Sanghera et al. | |
| 10,512,424 B2 | 12/2019 | Demmer et al. | |
| 10,518,094 B2 | 12/2019 | Sheldon et al. | |
| 11,007,369 B2 | 5/2021 | Sheldon et al. | |
| 2012/0095521 A1 | 4/2012 | Hintz | |
| 2013/0261497 A1 | 10/2013 | Pertijs et al. | |
| 2013/0325081 A1 | 12/2013 | Karst et al. | |
| 2016/0129263 A1 | 5/2016 | Demmer et al. | |
| 2017/0100594 A1 | 4/2017 | Huelskamp et al. | |
| 2018/0021582 A1 | 1/2018 | An et al. | |
| 2018/0085588 A1 | 3/2018 | Splett et al. | |
| 2019/0083779 A1 | 3/2019 | Yang et al. | |
| 2019/0308022 A1 | 10/2019 | Demmer et al. | |
| 2020/0054880 A1 * | 2/2020 | Fishler | A61N 1/37512 |
| 2020/0540880 | 2/2020 | Fishler | |
| 2020/0121931 A1 | 4/2020 | Sheldon et al. | |
| 2021/0236825 A1 | 8/2021 | Sheldon et al. | |

OTHER PUBLICATIONS (PCT/US2021/047062) PCT Notification of Transmittal of the International Search Report and the Written Opinion of the International Searching Authority, dated Dec. 6, 2021, 11 pages.

Alt, et al., "A New Rate-Modulated Pacemaker System Optimized by Combination of Two Sensors," PACE—Pacing and Clinical Electrophysiology, vol. 11, No. 8, Aug. 1, 1988, pp. 1119-1129.

* cited by examiner

DUAL SENSORS TO CONTROL PACING RATE

REFERENCE TO RELATED APPLICATIONS

This application claims the benefit of U.S. Provisional Patent Application No. 63/076,420 filed on Sep. 10, 2020, incorporated herein by reference in its entirety.

TECHNICAL FIELD

This disclosure relates to a medical device configured to deliver rate response cardiac pacing based on at least two sensor signals.

BACKGROUND

During normal sinus rhythm (NSR), the heartbeat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (AV) node. The AV node responds by propagating a ventricular depolarization signal through the bundle of His of the ventricular septum and thereafter to the bundle branches and the Purkinje muscle fibers of the right and left ventricles, sometimes referred to as the "His-Purkinje system."

Patients with a conduction system abnormality, e.g., SA node dysfunction or poor AV node conduction, bundle branch block, or other conduction abnormalities, may receive a pacemaker to restore a more normal heart rhythm. A single chamber pacemaker coupled to a transvenous lead carrying electrodes positioned in the right atrium may provide atrial pacing to treat a patient having SA node dysfunction. When the AV node is functioning normally, single chamber atrial pacing may sufficiently correct the heart rhythm. The pacing-evoked atrial depolarizations may be conducted normally to the ventricles via the AV node and the His-Purkinje system maintaining normal AV synchrony. Some patients, however, may experience conduction abnormalities of the AV node, e.g., partial or complete AV block. AV block may be intermittent and may evolve over time. In the presence of high-grade AV block, atrial depolarizations are not conducted to the ventricles on every atrial cycle. A single chamber ventricular pacemaker may be implanted in some patients to provide ventricular sensing and ventricular rate support A dual chamber pacemaker may be implanted in patients experiencing AV block to pace both the atrial and ventricular chambers and maintain AV synchrony. The dual chamber pacemaker may be coupled to a transvenous atrial lead and a transvenous ventricular lead, for placing electrodes for sensing and pacing in both the atrial and ventricular chambers. The pacemaker itself is generally implanted in a subcutaneous pocket with the transvenous leads tunneled to the subcutaneous pocket.

Intracardiac pacemakers have been introduced or proposed for implantation entirely within a patient's heart eliminating the need for transvenous leads. For example, an atrial intracardiac pacemaker may provide sensing and pacing from within an atrial chamber of a patient having bradycardia or SA node dysfunction but is expected to have AV conduction. A ventricular intracardiac pacemaker may provide sensing and pacing from within a ventricular chamber of a patient having AV block to provide ventricular rate support.

Single and dual chamber pacemakers have been proposed or are available for providing rate response cardiac pacing, sometimes referred to as "rate adaptive" cardiac pacing. In a rate response pacemaker, the cardiac pacing rate can be increased when a patient is exercising to provide increased rate support during physical activity.

SUMMARY

The techniques of this disclosure generally relate to a pacemaker configured to sense at least two different sensor signals that are each correlated to patient physical activity and/or metabolic demand and control the cardiac pacing rate based on the two sensor signals. The pacemaker may include an accelerometer for determining a patient activity metric based on an acceleration signal responsive to patient body motion. The pacemaker may set a sensor indicated pacing rate (SIR), also referred to herein as a "target pacing rate," based on the patient activity metric. According to the techniques disclosed herein, the pacemaker includes a second sensor for sensing a second signal that is correlated to patient physical activity or metabolic demand. In one example, the second sensor is a temperature sensor. The second sensor signal may be used by the pacemaker to adjust the SIR. In some examples, a pacemaker operating according to the techniques disclosed herein determines an activity metric from the accelerometer signal, sets an SIR based on the activity metric, and adjusts the SIR based on the temperature signal.

In one example, the disclosure provides a medical device including an accelerometer configured to generate an acceleration signal and a temperature sensor configured to generate a temperature signal. The device includes a control circuit configured to determine an activity metric from the acceleration signal, determine that the activity metric is equal to or greater than a previously determined activity metric and determine a temperature change from the temperature signal. In response to the activity metric being equal to or greater than a previously determined activity metric, the control circuit adjusts a target pacing rate based at least on the temperature change.

In another example, the disclosure provides a method including generating an acceleration signal, sensing a temperature signal, determining an activity metric from the acceleration signal and determining that the activity metric is greater than or equal to a previously determined activity metric. The method includes determining a temperature change from the temperature signal and adjusting a target pacing rate based at least on the temperature change in response to the activity metric being greater than or equal to the previously determined activity metric.

In another example, the disclosure provides a non-transitory, computer-readable storage medium storing a set of instructions which, when executed by a control circuit of a medical device, cause the medical device to generate an acceleration signal, generate a temperature signal, determine an activity metric from the acceleration signal and determine that the activity metric is equal to or greater than a previously determined activity metric. The instructions further cause the medical device to determine a temperature change from the temperature signal and adjust a target pacing rate based at least on the temperature change in response to the activity metric being equal to or greater than a previously determined activity metric.

Further disclosed herein is the subject matter of the following clauses:

1. A medical device comprising:
   an accelerometer configured to generate an acceleration signal;
   a temperature sensor configured to generate a temperature signal;
   a control circuit configured to:
      receive the acceleration signal and the temperature signal;
      determine an activity metric from the acceleration signal, wherein the activity metric represents patient physical activity;
      determine that the activity metric is equal to or greater than a previously determined activity metric;
      determine a temperature change from the temperature signal; and
      adjust, in response to the activity metric being equal to or greater than the previously determined activity metric, a target pacing rate based at least on the temperature change.

2. The medical device of clause 1, wherein the control circuit is configured to determine that the activity metric is not decreasing by:
   determining the target pacing rate based on the activity metric; and
   determining that the target pacing rate is equal to or greater than a previously determined target pacing rate based on the previously determined activity metric.

3. The medical device of any of clauses 1-2, wherein the control circuit is configured to:
   determine the target pacing rate based on the activity metric;
   determine that at least one of the activity metric is greater than or equal to an activity threshold or the target pacing rate is greater than or equal to a rate threshold; and
   determine the temperature change in response to the at least one of the activity metric being greater than or equal to the activity threshold or the target pacing rate being greater than or equal to the rate threshold.

4. The medical device of any of clauses 1-3, wherein the control circuit is further configured to determine that the at least one of the activity metric is greater than or equal to the activity threshold or the target pacing rate is greater than or equal to the rate threshold when the activity metric threshold and the rate threshold correspond to activities of daily living.

5. The medical device of any of clauses 1-4, wherein the control circuit is configured to:
   determine the target pacing rate based on the activity metric;
   determine that the temperature change is less than a threshold change; and
   adjust the target pacing rate by holding the target pacing rate at a current rate in response to the temperature change being less than the threshold change.

6. The medical device of any of clauses 1-5, wherein the control circuit is configured to:
   determine a moving average of the temperature signal;
   determine a current temperature from the temperature signal;
   determine a difference between the current temperature and the moving average;
   determine that the difference is less than an exercise offset threshold;
   adjust the target pacing rate by decreasing the target pacing rate in response to the difference being less than the exercise offset threshold.

7. The medical device of any of clauses 1-6, wherein the control circuit is configured to:
   determine the target pacing rate based on the activity metric;
   determine that the temperature change is an increase in temperature;
   adjust the target pacing rate by increasing the target pacing rate in response to the temperature change being an increase.

8. The medical device of any of clauses 1-7, wherein the control circuit is configured to:
   determine the target pacing rate based on the activity metric;
   determine a temperature from the temperature signal at a first rate when at least one of the activity metric is less than an activity threshold or the target pacing rate is less than a rate threshold; and
   determine the temperature from the temperature signal at a second rate for determining the temperature change when at least one of the activity metric is greater than or equal to the activity threshold or the target pacing rate is greater than or equal to the rate threshold, the second rate higher than the first rate.

9. The medical device of clause 8, wherein the control circuit is configured to:
   determine the temperature from the temperature signal at the first rate by disabling determining the temperature change.

10. The medical device of any of clauses 1-9, wherein the control circuit is configured to:
    set the target pacing rate based on the activity metric according to a transfer function defined by at least one slope and at least one set point relating the activity metric to the target pacing rate;
    adjust the target pacing rate based on at least the temperature change by: adjusting the transfer function based on the temperature change by adjusting at least one of the at least one slope or the least one set point; and determining the adjusted target pacing rate according to the adjusted transfer function.

11. The medical device of any of clauses 1-10, wherein the control circuit is configured to:
    receive a signal transmitted by another device; and
    determine the temperature change in response to receiving the transmitted signal.

12. The medical device of any of clauses 1-11, wherein the control circuit determines the temperature change by:
    determining a moving average of the temperature signal over a time interval;
    determining a current temperature from the temperature signal;
    comparing the current temperature to the moving average; and
    determining the temperature change based on the comparison.

13. The medical device of any of clauses 1-12, wherein the control circuit determines the temperature change by:
    determining a plurality of consecutive differences between consecutive temperatures determined from the temperature signal; and
    determining the temperature change as an increase in response to a threshold number of the consecutive differences being positive;

determining the temperature change as a decrease in response to a threshold number of consecutive differences being negative; and determining the temperature change as no change in response to the plurality of consecutive differences including both positive and negative differences.

14. The medical device of any of clauses 1-13, wherein the control circuit is configured to:
   determine that the activity metric is equal to or greater than the previously determined activity metric by determining that the previously determined activity metric is less than or equal to a lower rate set point and determining that the activity metric increased from the lower rate set point;
   determine that the temperature change is one of a decrease in temperature or no change in temperature; and
   adjust the target pacing rate by holding the target pacing rate at a lower rate in response to the temperature change.

15. The medical device of any of clauses 1-14, further comprising a sensing circuit configured to sense a cardiac electrical signal;
   wherein the control circuit is configured to:
      detect a tachyarrhythmia from at least one of the sensed cardiac electrical signal and the acceleration signal; and
      determine the temperature change in response to detecting the tachyarrhythmia.

16. The medical device of any of clauses 1-15 further comprising a pulse generator configured to generate cardiac pacing pulses at a rate based on the target pacing rate.

17. The medical device of clause 16, further comprising:
   a housing enclosing the accelerometer, the temperature sensor, the control circuit and the pulse generator, and
   a pair of pacing electrodes on the housing and electrically coupled to the pulse generator.

18. A method comprising:
   generating an acceleration signal;
   generating a temperature signal;
   determining an activity metric from the acceleration signal, wherein the activity metric represents patient physical activity;
   determining that the activity metric is equal to or greater than a previously determined activity metric;
   determining a temperature change from the temperature signal; and
   in response to the activity metric being equal to or greater than the previously determined activity metric, adjust a target pacing rate based at least on the temperature change.

19. The method of clause 18, wherein determining that the activity metric is equal to or greater than a previously determined activity metric comprises:
   determining the target pacing rate based on the activity metric; and
   determining that the target pacing rate is equal to or greater than a previously determined target pacing rate based on the previously determined activity metric.

20. The method of any of clauses 18-19, comprising:
   determining the target pacing rate based on the activity metric;
   determining that at least one of the activity metric is greater than or equal to an activity threshold or the target pacing rate is greater than or equal to a rate threshold; and
      determine the temperature change in response to the at least one of the activity metric being greater than or equal to the activity threshold or the target pacing rate being greater than or equal to the rate threshold.

21. The method of any of clauses 18-20, comprising determining that the at least one of the activity metric is greater than or equal to the activity threshold or the target pacing rate is greater than or equal to the rate threshold when the activity metric threshold and the rate threshold correspond to activities of daily living.

22. The method of any of clauses 18-21, further comprising:
   determining the target pacing rate based on the activity metric;
   determining that the temperature change is less than a threshold change; and
   adjusting the target pacing rate by holding the target pacing rate at a current rate in response to the temperature change being less than the threshold change.

23. The method of any of clauses 18-22, comprising:
   determining a moving average of the temperature signal;
   determining a current temperature from the temperature signal;
   determining a difference between the current temperature and the moving average;
   determining that the difference is less than an exercise offset threshold; and
   adjusting the target pacing rate by decreasing the target pacing rate in response to the difference being less than the exercise offset threshold.

24. The method of any of clauses 18-23, comprising:
   determining the target pacing rate based on the activity metric;
   determining that the temperature change is an increase in temperature;
   adjusting the target pacing rate by increasing the target pacing rate in response to the temperature change being an increase.

25. The method of any of clauses 18-24, further comprising:
   determining the target pacing rate based on the activity metric;
   determining a temperature from the temperature signal at a first rate when at least one of the activity metric is less than an activity threshold or the target pacing rate is less than a rate threshold; and
   determining the temperature from the temperature signal at a second rate for determining the temperature change when at least one of the activity metric is greater than or equal to the activity threshold or the target pacing rate is greater than or equal to the rate threshold, the second rate higher than the first rate.

26. The method of clause 25, comprising:
   determining the temperature from the temperature signal at the first rate by disabling determining the temperature change.

27. The method of any of clauses 18-26, comprising:
   setting the target pacing rate based on the activity metric according to a transfer function defined by at least one slope and at least one set point relating the activity metric to the target pacing rate; and
   adjusting the target pacing rate based on at least the temperature change by: adjusting the transfer function based on at least the temperature change by adjusting at least one of the at least one slope or the least one set point; and
   determining the adjusted target pacing rate based on the activity metric according to the adjusted transfer function.

28. The method of any of clauses 18-27, comprising:
   receiving a signal transmitted by another device; and
   determining the temperature change in response to receiving the transmitted signal.
29. The method of any of clauses 18-28, wherein determining the temperature change comprises:
   determining a moving average of the temperature signal over a time interval;
   determining a current temperature from the temperature signal;
   comparing the current temperature to the moving average; and
   determining the temperature change based on the comparison.
30. The method of any of clauses 18-29, wherein determining the temperature change comprises:
   determining a plurality of consecutive differences between consecutive temperatures determined from the temperature signal;
   determining the temperature change as an increase in response to a threshold number of the consecutive differences being positive;
   determining the temperature change as a decrease in response to a threshold number of consecutive differences being negative; and
   determining the temperature change as no change in response to the plurality of consecutive differences including both positive and negative differences.
31. The method of any of clauses 18-29 further comprising generating cardiac pacing pulses at a rate based on the target pacing rate.
32. The method of any of clauses 18-31, comprising:
   determining that the activity metric is equal to or greater than the previously determined activity metric by determining that the previously determined activity metric is less than or equal to a lower rate set point and determining that the activity metric is increased from the lower rate set point;
   determining that the temperature change is one of a decrease in temperature or no change in temperature; and
   adjusting the target pacing rate by holding the target pacing rate at a lower rate in response to the temperature change.
33. The method of any of clauses 18-32, comprising:
   sensing a cardiac electrical signal;
   detecting a tachyarrhythmia from at least one of the sensed cardiac electrical signal and the acceleration signal; and
   determining the temperature change in response to detecting the tachyarrhythmia.
34. The method of any of clauses 18-33 comprising generating cardiac pacing pulses at a rate based on the target pacing rate.
35. A non-transitory, computer-readable storage medium storing a set of instructions which, when executed by a control circuit of a medical device, cause the medical device to:
   generate an acceleration signal;
   generate a temperature signal;
   determine an activity metric from the acceleration signal;
   determine that the activity metric is greater than or equal to a previously determined activity metric;
   determine a temperature change from the temperature signal; and
   in response to the activity metric being greater than or equal to the previously determined activity metric, adjust a target pacing rate based at least on the temperature change.
36. A medical device comprising:
   an accelerometer configured to generate an acceleration signal;
   a temperature sensor configured to generate a temperature signal;
   a control circuit configured to:
      receive the acceleration signal and the temperature signal;
      determine an activity metric representative of patient physical activity from the acceleration signal;
      determine that the activity metric is equal to or greater than a previously determined activity metric;
      determine a temperature change from the temperature signal; and
      adjust, in response to the activity metric being equal to or greater than the previously determined activity metric, a target cardiac pacing rate based at least on the temperature change.
37. The medical device of clause 36, wherein the control circuit is further configured to:
   determine the target cardiac pacing rate based on the activity metric;
   determine that at least one of the activity metric is greater than or equal to an activity threshold or the target cardiac pacing rate is greater than or equal to a rate threshold; and
   determine the temperature change in response to the at least one of the activity metric being greater than or equal to the activity threshold or the target cardiac pacing rate being greater than or equal to the rate threshold.
38. The medical device of any of clauses 36-37, wherein the control circuit is configured to:
   determine the target cardiac pacing rate based on the activity metric;
   detect an increase in the activity metric;
   determine that the temperature change is less than a threshold change; and
   adjust the target cardiac pacing rate by holding the target cardiac pacing rate at a current rate in response to the temperature change being less than the threshold change and the increase in the activity metric is detected.
39. The medical device of any of clauses 36-38, wherein the control circuit is further configured to:
   determine a moving average of the temperature signal;
   determine a current temperature from the temperature signal;
   determine a difference between the current temperature and the moving average;
   determine that the difference is less than an exercise offset threshold; and
   adjust the target cardiac pacing rate by decreasing the target cardiac pacing rate in response to the difference being less than the exercise offset threshold.
40. The medical device of any of clauses 36-39, wherein the control circuit is further configured to:
   determine the target cardiac pacing rate based on the activity metric;
   determine that the temperature change is an increase in temperature; and adjust the target cardiac pacing rate by increasing the target cardiac pacing rate in response to the temperature change being an increase.

41. The medical device of any of clauses 36-40, wherein the control circuit is configured to:
   determine the target cardiac pacing rate based on the activity metric;
   determine a temperature from the temperature signal at a first rate when at least one of the activity metric is less than an activity threshold or the target cardiac pacing rate is less than a rate threshold; and
   determine the temperature from the temperature signal at a second rate for determining the temperature change when at least one of the activity metric is greater than or equal to the activity threshold or the target cardiac pacing rate is greater than or equal to the rate threshold, the second rate higher than the first rate.

42. The medical device of any of clauses 36-41, wherein the control circuit is further configured to:
   set the target cardiac pacing rate based on the activity metric according to a transfer function defined by at least one slope and at least one set point that relates the activity metric to the target cardiac pacing rate; and
   adjust the target cardiac pacing rate based on at least the temperature change by:
      adjusting the transfer function by adjusting at least one of the at least one slope or the least one set point; and
      determining the adjusted target cardiac pacing rate according to the adjusted transfer function.

43. The medical device of any of clauses 36-42, wherein the control circuit is further configured to:
   receive a signal transmitted by another device; and
   determine the temperature change in response to receiving the transmitted signal.

44. The medical device of any of clauses 36-43, wherein the control circuit is configured to determine the temperature change by:
   determining a moving average of the temperature signal over a time interval;
   determining a current temperature from the temperature signal;
   comparing the current temperature to the moving average; and
   determining the temperature change based on the comparison.

45. The medical device of any of clauses 36-44, wherein the control circuit is further configured to:
   determine that the previously determined activity metric is less than or equal to a lower rate set point;
   determine that the activity metric is increased from the lower rate set point;
   determine the target cardiac pacing rate based on the activity metric that is increased from the lower rate set point;
   determine that the temperature change is not increasing; and
   adjust the target cardiac pacing rate by holding the target cardiac pacing rate at a predetermined pacing lower rate in response to the temperature change not increasing when the activity metric is increased from the lower set point.

46. The medical device of any of clauses 36-45 1, further comprising a sensing circuit configured to sense a cardiac electrical signal;
   wherein the control circuit is further configured to:
      detect a tachyarrhythmia from at least one of the sensed cardiac electrical signal and the acceleration signal; and
      determine the temperature change in response to detecting the tachyarrhythmia.

47. The medical device of any of clauses 36-56, further comprising a pulse generator configured to generate cardiac pacing pulses at a rate based on the target cardiac pacing rate.

48. A method comprising:
   generating an acceleration signal;
   generating a temperature signal;
   determining an activity metric representative of patient physical activity from the acceleration signal;
   determining that the activity metric is equal to or greater than a previously determined activity metric;
   determining a temperature change from the temperature signal; and
   in response to the activity metric being equal to or greater than the previously determined activity metric, adjust a target cardiac pacing rate based at least on the temperature change.

49. The method of clause 48, further comprising:
   determining the target cardiac pacing rate based on the activity metric;
   determining that at least one of the activity metric is greater than or equal to an activity threshold or the target cardiac pacing rate is greater than or equal to a rate threshold; and
   determining the temperature change in response to the at least one of the activity metric being greater than or equal to the activity threshold or the target cardiac pacing rate being greater than or equal to the rate threshold.

50. The method of any of clauses 48-49, further comprising:
   determining the target cardiac pacing rate based on the activity metric;
   detecting an increase in the activity metric;
   determining that the temperature change is less than a threshold change; and
   adjusting the target cardiac pacing rate by holding the target cardiac pacing rate at a current rate in response to the temperature change being less than the threshold change and the increase in the activity metric is detected.

51. The method of any of clauses 48-50, further comprising:
   determining a moving average of the temperature signal;
   determining a current temperature from the temperature signal;
   determining a difference between the current temperature and the moving average;
   determining that the difference is less than an exercise offset threshold; and
   adjusting the target cardiac pacing rate by decreasing the target cardiac pacing rate in response to the difference being less than the exercise offset threshold.

52. The method of any of clauses 48-51, further comprising:
   determining the target cardiac pacing rate based on the activity metric;
   determining that the temperature change is an increase in temperature; and
   adjusting the target cardiac pacing rate by increasing the target cardiac pacing rate in response to the temperature change being an increase.

53. The method of any of clauses 48-52, further comprising:
   determining the target cardiac pacing rate based on the activity metric;

determining a temperature from the temperature signal at a first rate when at least one of the activity metric is less than an activity threshold or the target cardiac pacing rate is less than a rate threshold; and determining the temperature from the temperature signal at a second rate for determining the temperature change when at least one of the activity metric is greater than or equal to the activity threshold or the target cardiac pacing rate is greater than or equal to the rate threshold, the second rate higher than the first rate.

54. The method of any of clauses 48-53, comprising:
setting the target cardiac pacing rate based on the activity metric according to a transfer function defined by at least one slope and at least one set point that relates the activity metric to the target cardiac pacing rate; and
adjusting the target cardiac pacing rate based on at least the temperature change by:
adjusting the transfer function by adjusting at least one of the at least one slope or the least one set point; and
determining the adjusted target cardiac pacing rate based on the activity metric according to the adjusted transfer function.

55. The method of any of clauses 48-54, further comprising:
receiving a signal transmitted by another device; and
determining the temperature change in response to receiving the transmitted signal.

56. The method of any of clauses 48-55, wherein determining the temperature change comprises:
determining a moving average of the temperature signal over a time interval;
determining a current temperature from the temperature signal;
comparing the current temperature to the moving average; and
determining the temperature change based on the comparison.

57. The method of any of clauses 48-56, further comprising:
determining that the previously determined activity metric is less than or equal to a lower rate set point;
determining that the activity metric is increased from the lower rate set point;
determining that the temperature change is not increasing; and
adjusting the target cardiac pacing rate by holding the target cardiac pacing rate at a predetermined pacing lower rate in response to the temperature change not increasing when the activity metric is increased from the lower set point.

58. The method of any of clauses 48-57, further comprising:
sensing a cardiac electrical signal;
detecting a tachyarrhythmia from at least one of the sensed cardiac electrical signal and the acceleration signal; and
determining the temperature change in response to detecting the tachyarrhythmia.

59. The method of any of clauses 48-58, further comprising generating cardiac pacing pulses at a rate based on the target cardiac pacing rate.

60. A non-transitory, computer-readable storage medium storing a set of instructions which, when executed by a control circuit of a medical device, cause the medical device to:
generate an acceleration signal;
generate a temperature signal;
determine an activity metric representative of patient physical activity from the acceleration signal;
determine that the activity metric is greater than or equal to a previously determined activity metric;
determine a temperature change from the temperature signal; and
in response to the activity metric being greater than or equal to the previously determined activity metric, adjust a target cardiac pacing rate based at least on the temperature change.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

In general, this disclosure describes a pacemaker and techniques for controlling rate response cardiac pacing. The pacemaker includes at least two different sensors for sensing a signal correlated to patient physical activity and/or metabolic demand. The pacemaker controls the pacing rate based on the two different sensor signals.

Figure 1:
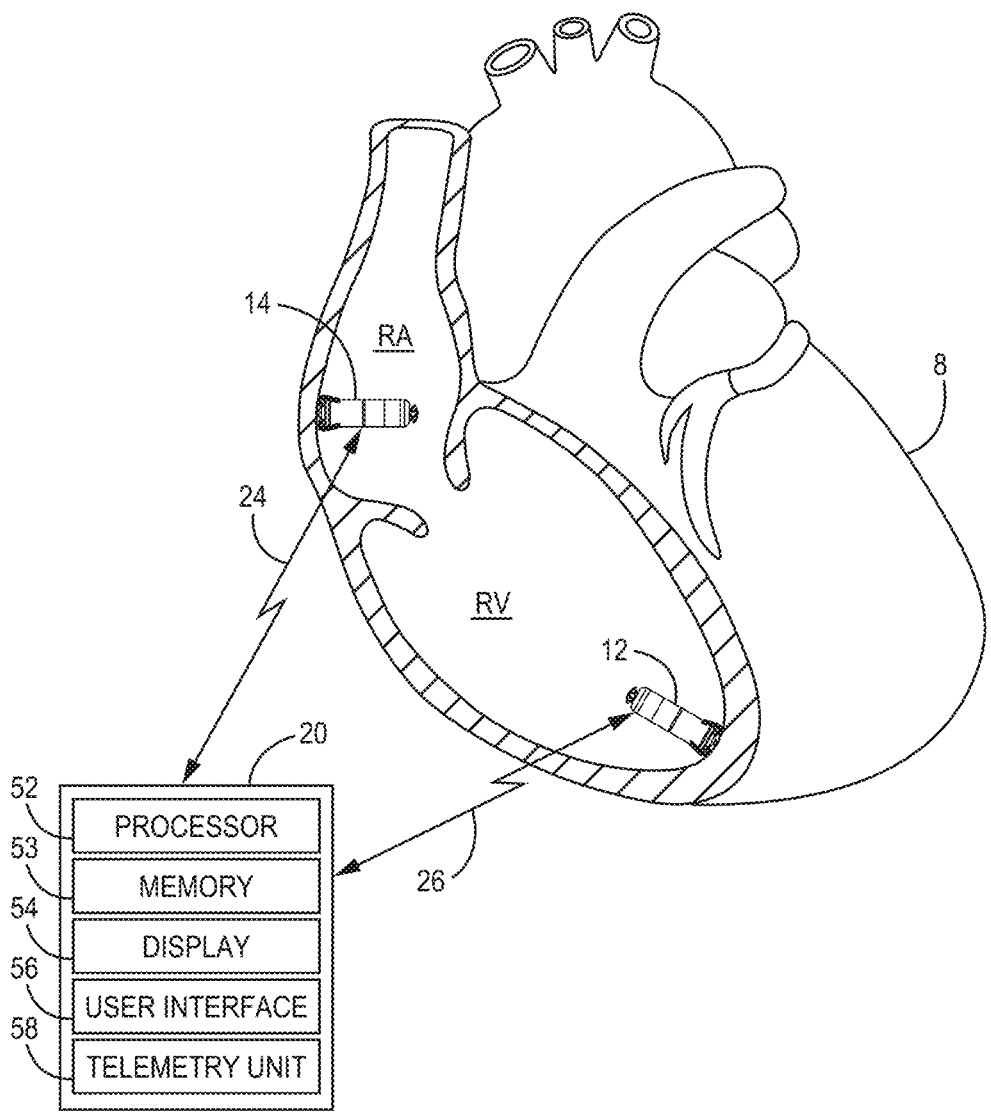
FIG. 1 is a conceptual diagram illustrating an implantable medical device (IMD) system that may be used to sense cardiac signals and provide rate response cardiac pacing.

FIG. 1 is a conceptual diagram illustrating an implantable medical device (IMD) system 10 that may be used to sense cardiac signals and provide rate response cardiac pacing. IMD system 10 is shown including a pacemaker 14, shown implanted within the right atrium (RA). Pacemaker 14 may be a transcatheter leadless pacemaker which is implantable wholly within a heart chamber, e.g., wholly within the right atrium (RA) of heart 8 for sensing cardiac signals and delivering atrial pacing pulses from within the atrium. Pacemaker 14 may be implanted along the lateral endocardial wall as shown though other locations are possible within or on the RA, different than the location shown. For example, pacemaker 14 may be implanted along the inferior end of the interatrial septum, beneath the AV node and near the tricuspid valve annulus to position an electrode for advancement into the interatrial septum toward the His bundle for providing ventricular pacing, which may provide pacing along the ventricular conduction system to capture the heart's native conduction system. Examples of various pacing electrode arrangements and medical device configurations for providing cardiac pacing along the native conduction system of the heart, which may be configured to perform the rate response pacing techniques disclosed herein, are generally disclosed in U.S. Publication No. 2019/0083779 (Yang, et al.) and U.S. Pat. No. 11,007,369 (Sheldon, et al.), both of which are incorporated herein by reference in their entirety.

IMD system 10 may additionally or alternatively include ventricular pacemaker 12, shown implanted in the right ventricle (RV). Pacemaker 12 may also be a transcatheter leadless pacemaker, which may be wholly implantable within a ventricular heart chamber (as shown) or on a ventricular chamber, e.g., at an epicardial location, for sensing cardiac signals and delivering ventricular pacing pulses. Pacemakers 12 and 14 may be reduced in size compared to subcutaneously implanted pacemakers and may be generally cylindrical in shape to enable transvenous implantation via a delivery catheter. The techniques disclosed herein are not necessarily limited to a particular pacemaker location and may be implemented in an implantable medical device implanted in a variety of locations.

Pacemakers 12 and 14 may each include housing-based electrodes for sensing cardiac electrical signals and delivering pacing pulses. Pacemaker 14 may include cardiac electrical signal sensing circuitry configured to sense atrial P-waves attendant to the depolarization of the atrial myocardium and a pulse generator for generating and delivering an atrial pacing pulse in the absence of a sensed atrial P-wave. Pacemaker 12 includes cardiac electrical signal sensing circuitry configured to sense ventricular R-waves attendant to ventricular myocardial depolarizations and a pulse generator for generating and delivering a ventricular pacing pulse in the absence of a sensed R-wave.

Pacemakers 12 and/or 14 include an accelerometer enclosed within or on the housing of the pacemaker. The accelerometer is subjected to acceleration forces due to cardiac and blood motion as well as patient body motion, e.g., during physical activity. The acceleration signal produced by the accelerometer may be correlated to patient physical activity, therefore, and used by processing circuitry included in the pacemaker for determining a patient activity metric. The rate of cardiac pacing pulses generated and delivered by pacemaker 12 or 14 may be adjusted based on the patient activity metric determined from the accelerometer signal. In some examples, the accelerometer signal may be used for sensing cardiac events for use in controlling pacing, such as in a dual chamber pacing mode. For instance, ventricular pacemaker 12 may sense atrial events from the accelerometer signal for providing atrial synchronous ventricular pacing pulses, e.g., delivered at an atrioventricular delay interval from a preceding sensed atrial event. Examples of a leadless dual chamber pacemaker that may be configured to perform rate response pacing according to the techniques disclosed herein are generally described in U.S. Patent Publication No. 2021/0236825 (Sheldon, et al.), incorporated herein by reference in its entirety.

Pacemakers 12 and/or 14 may additionally include a second sensor for use in controlling the rate response pacing rate. A second sensor is a temperature sensor in some examples. When the accelerometer is included in or on the housing of pacemaker 12 and/or 14 implanted in or on the heart 8, cardiac and blood motion contribute to the acceleration signal produced by the accelerometer. As the heart 8 is paced faster in response to an increased patient activity metric, the increased cardiac rate may further contribute to an elevated patient activity metric determined from the acceleration signal. This increased contribution of cardiac motion to the acceleration signal during patient physical activity may be a confounding factor in determining a patient activity metric that reflects the actual maximum activity level reached by the patient and/or determining when the patient physical activity decreases or ceases, since the heart 8 may still be paced at a higher rate.

In some instances, atrial tachyarrhythmia may contribute to the acceleration signal before or after the onset of increased patient physical activity. Intervals of non-sustained or intermittent atrial tachyarrhythmia, including atrial tachycardia and atrial fibrillation, may occur in some patients having pacemaker 14 implanted in the RA and/or pacemaker 12 implanted in the RV. The onset of atrial tachyarrhythmia while the patient is at rest may cause an increase the cardiac contribution to the accelerometer signal, potentially resulting in an increase in the patient activity metric determined from the acceleration signal and an increased pacing rate output by the pacemaker, particular pacemaker 14 implanted in the RA. When the onset of atrial tachyarrhythmia occurs before or during increased patient physical activity, the increased contribution of cardiac motion to the acceleration signal during patient physical activity may prevent or slow a decrease in the rate response pacing rate as patient physical activity declines or ceases.

According to the techniques disclosed herein, a second sensor, e.g., a temperature sensor, is included in pacemaker 12 and/or 14 to provide a second signal that is correlated to patient physical activity and metabolic need. The second sensor signal may be used by the pacemaker to control rate response pacing in addition to the accelerometer signal. As described below, the second sensor signal may be used to withhold an adjustment to the pacing rate based on the patient activity metric determined from the accelerometer signal or used directly to adjust the applied pacing rate. In some examples, the second sensor signal may be used to determine the applied pacing rate over selected intervals of pacing rates instead of the accelerometer signal.

While both a ventricular pacemaker 12 and an atrial pacemaker 14 are shown in FIG. 1 for the sake of illustration, it is to be understood that a patient may receive one pacemaker, either ventricular pacemaker 12 or atrial pacemaker 14, or both pacemakers 12 and 14 for providing cardiac signal sensing and cardiac pacing functions. When the patient receives both pacemakers 12 and 14, one or both pacemaker 12 and pacemaker 14 may be configured to perform rate response pacing according to the techniques disclosed herein.

Pacemakers 12 and 14 may be capable of bidirectional wireless communication with an external device 20 for programming sensing and pacing control parameters, which may include control parameters used for sensing the acceleration signal and the second sensor signal, determining the SIR, and providing rate response pacing. Aspects of external device 20 may generally correspond to the external programming/monitoring unit disclosed in U.S. Pat. No. 5,507,782 (Kieval, et al.), hereby incorporated herein by reference in its entirety. External device 20 is often referred to as a "programmer" because it is typically used by a physician, technician, nurse, clinician or other qualified user for programming operating parameters in an implantable medical device, e.g., pacemaker 12 or pacemaker 14. External device 20 may be located in a clinic, hospital or other medical facility. External device 20 may alternatively be embodied as a home monitor or a handheld device that may be used in a medical facility, in the patient's home, or another location. Operating parameters, including sensing and therapy delivery control parameters, may be programmed into pacemaker 12 or pacemaker 14 by a user interacting with external device 20.

External device 20 may include a processor 52, memory 53, display unit 54, user interface 56 and telemetry unit 58. Processor 52 controls external device operations and processes data and signals received from pacemaker 12 or 14 (or other examples of implantable medical device given herein). Display unit 54 may generate a display, which may include a graphical user interface, of data and information relating to pacemaker functions to a user for reviewing pacemaker operation and programmed parameters as well as cardiac electrical signals, accelerometer signals, second sensor signals or other physiological data that may be acquired by pacemaker 12 and/or pacemaker 14 and transmitted to external device 20 during an interrogation session. For example, pacemaker 12 or 14 may generate an output for transmission to external device 20 including patient activity metrics, SIR, second sensor signal data such as temperature change data, applied pacing rate data, or other rate response pacing-related data. Transmitted data may include an episode of a cardiac electrical signal produced by pacemaker sensing circuitry including markers indicating pacing pulse delivery and sensed cardiac event signals, e.g., ventricular sensed events and/or atrial sensed events corresponding to sensed R-waves and sensed P-waves, respectively.

User interface 56 may include a mouse, touch screen, keypad or the like to enable a user to interact with external device 20 to initiate a telemetry session with pacemaker 12 or pacemaker 14 for retrieving data from and/or transmitting data to the pacemaker 12 or 14, including programmable parameters for controlling rate response pacing. Telemetry unit 58 includes a transceiver and antenna configured for bidirectional communication with a telemetry circuit included in pacemakers 12 and 14 and is configured to operate in conjunction with processor 52 for sending and receiving data relating to pacemaker functions via communication link 24 and communication link 26. Telemetry unit 58 may establish a wireless bidirectional communication link 24 or 26 with pacemaker 14 or 12, respectively. Communication link 24 may be established using a radio frequency (RF) link such as BLUETOOTH®, Wi-Fi, Medical Implant Communication Service (MICS) or other communication bandwidth. In some examples, external device 20 may include a programming head that is placed proximate pacemaker 12 or 14 to establish and maintain a communication link 24, and in other examples external device 20 and pacemakers 12 and 14 may be configured to communicate using a distance telemetry algorithm and circuitry that does not require the use of a programming head and does not require user intervention to maintain a communication link.

It is contemplated that external device 20 may be in wired or wireless connection to a communications network via a telemetry circuit that includes a transceiver and antenna or via a hardwired communication line for transferring data to a centralized database or computer to allow remote management of the patient. Remote patient management systems including a centralized patient database may be configured to utilize the presently disclosed techniques to enable a clinician to view data relating to rate response pacing operations performed by pacemaker 12 or pacemaker 14.

Figure 2:
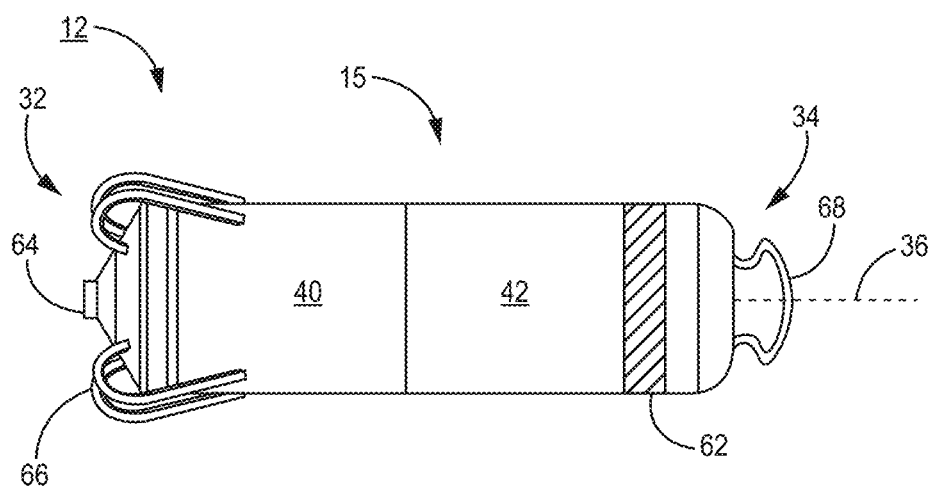
FIG. 2 is a conceptual diagram of a transcatheter leadless pacemaker according to one example.

FIG. 2 is a conceptual diagram of a transcatheter leadless pacemaker according to one example. The pacemaker shown in FIG. 2 may correspond to pacemaker 12 of FIG. 1, configured for implantation in or on a ventricular chamber. Features of pacemaker 12 described in conjunction with FIG. 2, however, may generally correspond to features included in a pacemaker deployable at other cardiac locations, such as pacemaker 14 shown in the RA in FIG. 1. For example, the shape and/or locations of electrodes, fixation members or other features of pacemaker 12 may be adapted for use at other implantation locations in, on or around the patient's heart.

Pacemaker 12 includes a housing 15 that may enclose a control electronics subassembly 40 and a battery subassembly 42, which provides power to the control electronics subassembly 40. Pacemaker 12 includes electrodes 62 and 64 spaced apart along the housing 15 of pacemaker 12 for sensing cardiac electrical signals and delivering pacing pulses. Electrode 64 is shown as a tip electrode extending from a distal end 32 of pacemaker 12, and electrode 62 is shown as a ring electrode circumscribing the lateral wall of housing 15, along a mid-portion of housing 15. In the example shown, electrode 62 is shown adjacent proximal end 34 of housing 15. Distal end 32 is referred to as "distal" in that it is expected to be the leading end of pacemaker 12 as pacemaker 12 is advanced through a delivery tool, such as a catheter, and placed against a targeted pacing site.

Electrodes 62 and 64 form an anode and cathode pair for bipolar cardiac pacing and sensing. In alternative embodiments, pacemaker 12 may include two or more ring electrodes, two tip electrodes, and/or other types of electrodes exposed along pacemaker housing 15 for delivering electrical stimulation to heart 8 and sensing cardiac electrical signals. Electrodes 62 and 64 may be, without limitation, titanium, platinum, iridium or alloys thereof and may include a low polarizing coating, such as titanium nitride, iridium oxide, ruthenium oxide, platinum black, among others. Electrodes 62 and 64 may be positioned at locations along pacemaker 12 other than the locations shown and may include ring, button, hemispherical, hook, helical or other types of electrodes.

Housing 15 is formed from a biocompatible material, such as a stainless steel or titanium alloy. In some examples, the housing 15 may include an insulating coating. Examples of insulating coatings include parylene, urethane, PEEK, or polyimide, among others. The entirety of the housing 15 may be insulated, but only electrodes 62 and 64 uninsulated. Electrode 64 may serve as a cathode electrode and be coupled to internal circuitry, e.g., a pacing pulse generator and cardiac electrical signal sensing circuitry, enclosed by housing 15 via an electrical feedthrough crossing housing 15. Electrode 62 may be formed as a conductive portion of housing 15 defining a ring electrode that is electrically isolated from the other portions of the housing 15 as generally shown in FIG. 2. In other examples, the entire periphery of the housing 15 may function as an electrode that is electrically isolated from tip electrode 64, instead of providing a localized ring electrode such as electrode 62. Electrode 62 formed along an electrically conductive portion of housing 15 serves as a return anode during pacing and sensing.

Control electronics subassembly 40 includes the electronics for sensing cardiac signals, producing pacing pulses and controlling therapy delivery and other functions of pacemaker 12 as described herein. A motion sensor implemented as an accelerometer may be enclosed within housing 15 in some examples. The accelerometer provides a signal to a processor included in control electronics subassembly 40 for signal processing and analysis for determining a patient activity metric for use in controlling rate response cardiac pacing.

The accelerometer may be a multi-axis or multi-dimensional accelerometer where each axis of the accelerometer generates an acceleration signal in a different dimension. In some examples, the accelerometer may have one "longitudinal" axis that is parallel to or aligned with the longitudinal axis 36 of pacemaker 12 and two orthogonal axes that extend in radial directions relative to the longitudinal axis 36. Practice of the techniques disclosed herein, however, are not limited to a particular orientation of the accelerometer within or along housing 15 or a particular number of axes. In other examples, a one-dimensional accelerometer may be used to obtain an acceleration signal from which a patient activity metric may be determined. In still other examples, a two dimensional accelerometer or other multi-dimensional accelerometer may be used. Each axis of a single or multi-dimensional accelerometer may be defined by a piezoelectric element, micro-electrical mechanical system (MEMS) device or other sensor element capable of producing an electrical signal in response to changes in acceleration imparted on the sensor element, e.g., by converting the acceleration to a force or displacement that is converted to the electrical signal. In a multi-dimensional accelerometer, the sensor elements may be arranged orthogonally with each sensor element axis orthogonal relative to the other sensor element axes. Orthogonal arrangement of the elements of a multi-axis accelerometer, however, is not necessarily required.

Each sensor element or axis may produce an acceleration signal corresponding to a vector aligned with the axis of the sensor element. A vector signal of a multi-dimensional accelerometer (also referred to herein as a "multi-axis" accelerometer) for use in monitoring patient physical activity may be selected as a single axis signal or a combination of two or more axis signals. For example, one, two or all three axis signals produced by a three-dimensional accelerometer may be selected for processing and analysis for use in determining a patient physical activity metric by pacemaker 12. In a three-dimensional accelerometer, having one axis aligned with longitudinal axis 36 and two axes aligned orthogonally in two radial directions, one of the radial axis signals may be selected as a default axis for obtaining an acceleration signal for determining a patient physical activity metric. The axis signal or combination of axis signals used for determining a patient physical activity metric, however, may be selectable and may be programmable by a user. In some examples, the vector selection techniques for monitoring patient physical activity generally disclosed in U.S. Pat. No. 10,512,424 (Demmer, et al.) may be implemented in conjunction with the rate response control techniques disclosed herein. The '424 reference is incorporated herein by reference in its entirety.

Pacemaker 12 may include a second sensor on or enclosed by housing 15 for producing a signal correlated to metabolic demand for use in controlling rate response pacing. As described below in conjunction with FIG. 5, pacemaker 12 may include a temperature sensor enclosed by housing 15 as a second sensor for controlling rate response. When pacemaker 12 is implanted in or on the patient's heart, the accelerometer is subjected to acceleration forces due to cardiac motion as well as patient body motion. When pacemaker 12 increases the pacing rate to provide rate response pacing, the increased cardiac rate, as well as increased cardiac contractility that may occur as a normal response to exercise to increase cardiac output, contributes to increased acceleration signals. As a result, a patient activity metric based on the acceleration signal alone may remain elevated due to the increased cardiac rate, even when the patient activity begins to decline. This positive feedback effect of paced heart rate may lead to a sustained high, rate response pacing rate longer than needed to support the actual patient physical activity. A second sensor, such as a temperature sensor, may be less sensitive or insensitive to cardiac motion and provide a better indication of decreased patient physical activity and metabolic demand than the accelerometer during atrial tachyarrhythmia and when the rate response pacing rate is increased from a base, lower rate. Accordingly, pacemaker 12 and/or pacemaker 14 may include a temperature sensor in addition to the accelerometer and process both signals for determining an appropriate cardiac pacing rate response.

Pacemaker 12 may include features for facilitating deployment and fixation of pacemaker 12 at an implant site. For example, pacemaker 12 may include a set of fixation tines 66 to secure pacemaker 12 to patient tissue, e.g., by actively engaging with the ventricular endocardium and/or interacting with the ventricular trabeculae. Fixation tines 66 are configured to anchor pacemaker 12 to position electrode 64 in operative proximity to a targeted tissue for delivering therapeutic electrical stimulation pulses. Numerous types of active and/or passive fixation members may be employed for anchoring or stabilizing pacemaker 12 in an implant position. A pacemaker configured for implantation in an atrial chamber, such as pacemaker 14 shown in FIG. 1, may include a fixation member, which may include multiple fixation tines, having a different size and/or shape than tines 66 for fixation in the atrial endocardium or interacting with the atrial pectinate muscle.

Pacemaker 12 may optionally include a delivery tool interface 68. Delivery tool interface 68 may be located at the proximal end 34 of pacemaker 12 and is configured to connect to a delivery device, such as a catheter, used to position pacemaker 12 at an implant site during an implantation procedure, for example within or on a heart chamber.

Figure 3A:
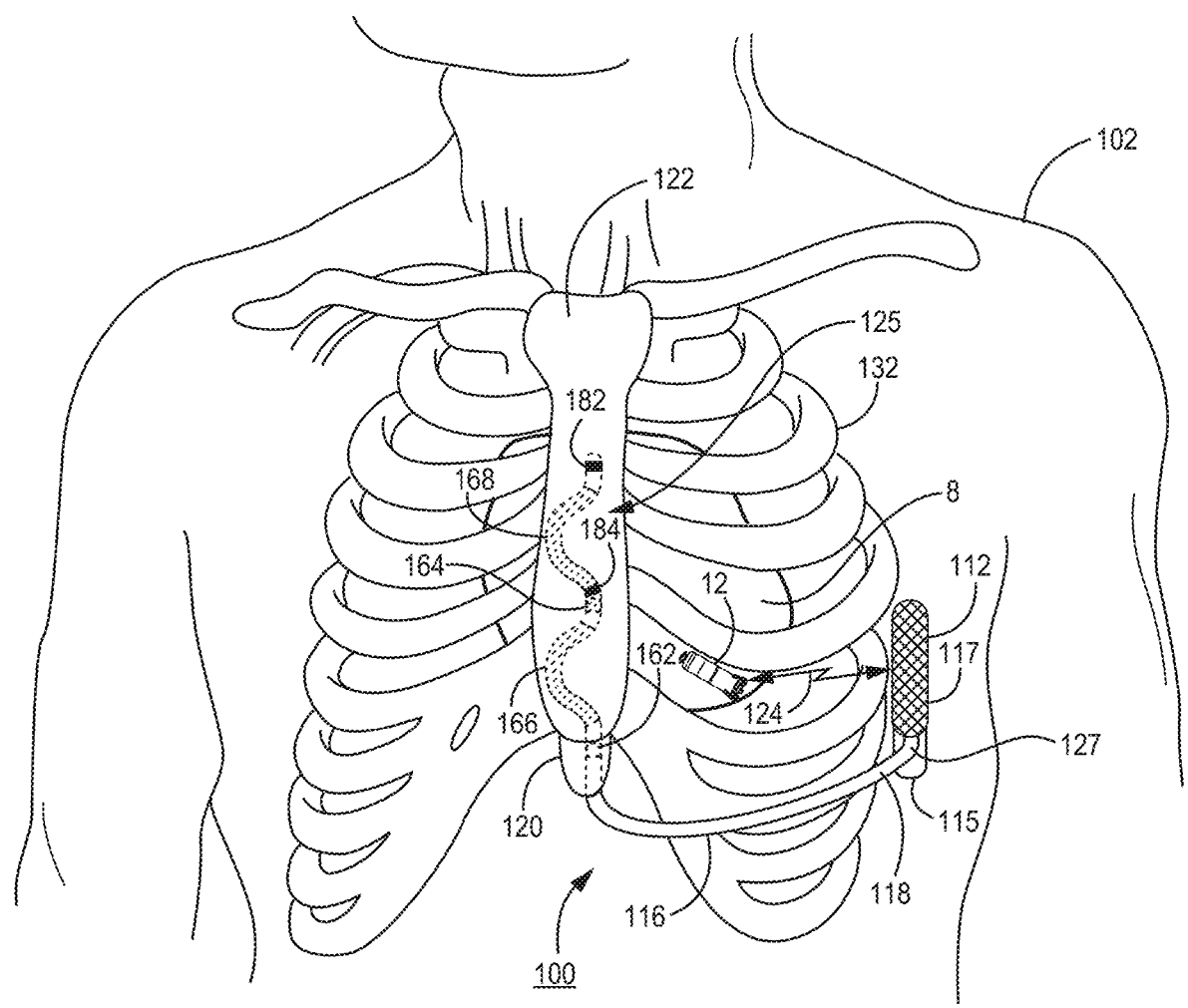
FIGS. 3A-3C are conceptual diagrams of a patient implanted with an IMD system that may be configured to deliver rate response pacing according to another example.
Figure 3B:
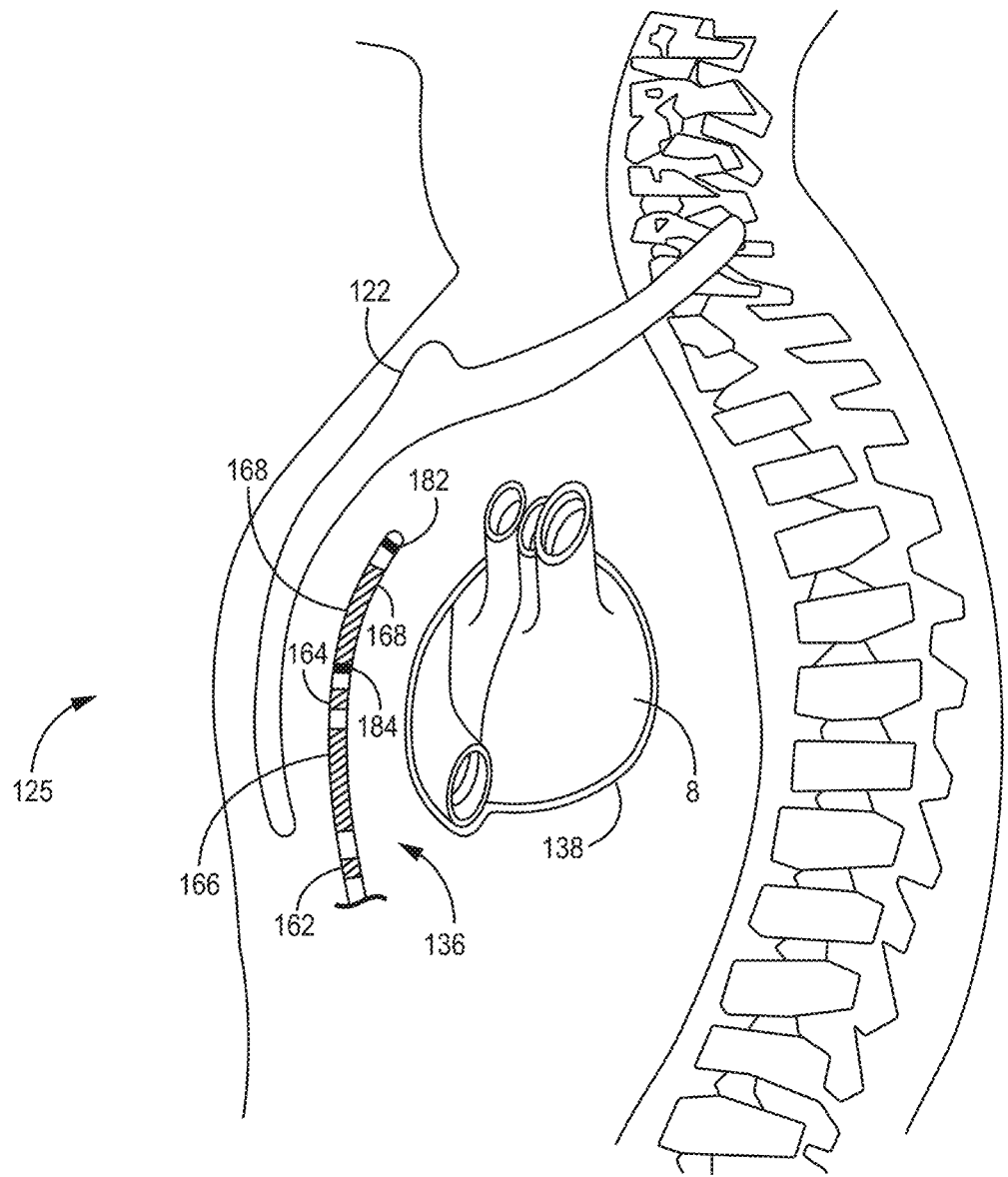
Figure 3C:
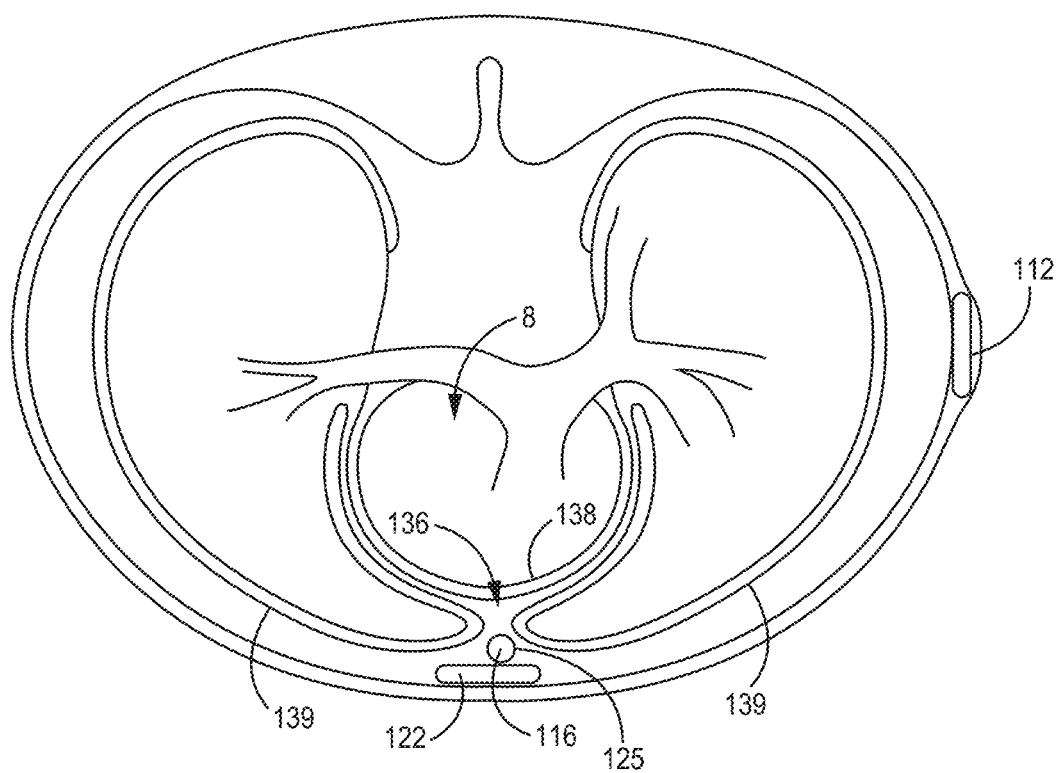

FIGS. 3A-3C are conceptual diagrams of a patient 102 implanted with an IMD system 100 that may be configured to deliver rate response pacing according to another example. FIG. 3A is a front view of patient 102 implanted with IMD system 100. FIG. 3B is a side view of patient 102 implanted with IMD system 100. FIG. 3C is a transverse view of patient 102 implanted with IMD system 100. In this example, IMD system 100 includes an implantable cardioverter defibrillator (ICD) 112 connected to an extra-cardiovascular electrical stimulation and sensing lead 116. In the implant configuration shown, lead 116 is implanted at least partially underneath sternum 122 of patient 102. Lead 116 extends subcutaneously or submuscularly from ICD 112 toward xiphoid process 120 and at a location near xiphoid process 120 bends or turns and extends superiorly within anterior mediastinum 136 (see FIGS. 3B and 3C) in a substernal position. The path of extra-cardiovascular lead 116 may depend on the location of ICD 112, the arrangement and position of electrodes carried by the lead body 118, and/or other factors. The techniques disclosed herein are not limited to a particular path of lead 116 or final locations of electrodes carried by lead body 118.

Anterior mediastinum 136 may be viewed as being bounded laterally by pleurae 139, posteriorly by pericardium 138, and anteriorly by sternum 122. The distal portion 125 of lead 116 may extend along the posterior side of sternum 122 substantially within the loose connective tissue and/or substernal musculature of anterior mediastinum 136. A lead implanted such that the distal portion 125 is substantially within anterior mediastinum 136, or within a pleural cavity or more generally within the thoracic cavity, may be referred to as a "substernal lead."

In the example illustrated in FIGS. 3A-3C, the distal portion 125 of lead 116 is located substantially centered under sternum 122. In other instances, however, lead 116 may be implanted such that the distal portion 125 may be offset laterally from the center of sternum 122. In some instances, lead 116 may extend laterally such that distal portion 125 is underneath/below the ribcage 132 in addition to or instead of sternum 122. In other examples, the distal portion 125 of lead 116 may be implanted in other extra-cardiovascular, intra-thoracic locations, including the pleural cavity or around the perimeter of and adjacent to or within the pericardium 138 of heart 8.

ICD 112 includes a housing 115 that forms a hermetic seal that protects internal components of ICD 112. The housing 115 of ICD 112 may be formed of a conductive material, such as titanium or titanium alloy. The housing 115 may function as an electrode (sometimes referred to as a "can" electrode). Housing 115 may be used as an active can electrode for use in delivering CV/DF shocks or other high voltage pulses delivered using a high voltage therapy circuit. In other examples, housing 115 may be available for use in delivering unipolar, low voltage cardiac pacing pulses and/or for sensing cardiac electrical signals in combination with electrodes carried by lead 116. In other instances, the housing 115 of ICD 112 may include a plurality of electrodes on an outer portion of the housing. The outer portion(s) of the housing 115 functioning as an electrode(s) may be coated with a material, such as titanium nitride, e.g., for reducing post-stimulation polarization artifact.

ICD 112 includes a connector assembly 117 (also referred to as a connector block or header) that includes electrical feedthroughs crossing housing 115 to provide electrical connections between conductors extending within the lead body 118 of lead 116 and electronic components included within the housing 115 of ICD 112. Housing 115 may house one or more processors, memories, transceivers, cardiac electrical signal sensing circuitry, therapy delivery circuitry, power sources and other components for sensing cardiac electrical signals, detecting a heart rhythm, and controlling and delivering electrical stimulation pulses to treat an abnormal heart rhythm. Circuitry that may be enclosed by housing 115 is generally described below in conjunction with FIG. 5 according to some examples.

Lead 116 is shown in this example as an extra-cardiovascular lead implanted in a substernal location. In other examples, lead 116 may be implanted outside the ribcage and sternum, e.g., in a suprasternal location or adjacent sternum 122, over ribcage 132. Lead 116 includes an elongated lead body 118 having a proximal end 127 that includes a lead connector (not shown) configured to be connected to ICD connector assembly 117 and a distal portion 125 that includes one or more electrodes. In the example illustrated in FIGS. 3A-3C, the distal portion 125 of lead body 118 includes defibrillation electrodes 166 and 168 and pace/sense electrodes 162 and 164. In some cases, defibrillation electrodes 166 and 168 may together form a defibrillation electrode in that they may be configured to be activated concurrently. Alternatively, defibrillation electrodes 166 and 168 may form separate defibrillation electrodes in which case each of the electrodes 166 and 168 may be activated independently.

Electrodes 166 and 168 (and in some examples housing 115) are referred to herein as defibrillation electrodes because they may be utilized, individually or collectively, for delivering high voltage stimulation therapy (e.g., cardioversion or defibrillation shocks). Electrodes 166 and 168 may be elongated coil electrodes and generally have a relatively high surface area for delivering high voltage electrical stimulation pulses compared to pacing and sensing electrodes 162 and 164. However, electrodes 166 and 168 and housing 115 may also be utilized to provide pacing functionality, including rate response pacing, sensing functionality, or both pacing and sensing functionality in addition to or instead of high voltage stimulation therapy. In this sense, the use of the term "defibrillation electrode" herein should not be considered as limiting the electrodes 166 and 168 for use in only high voltage cardioversion/defibrillation shock therapy applications. For example, either of electrodes 166 and 168 may be used as a sensing electrode in a sensing vector for sensing cardiac electrical signals and determining a need for an electrical stimulation therapy.

Electrodes 162 and 164 are relatively smaller surface area electrodes which are available for use in sensing electrode vectors for sensing cardiac electrical signals and may be used for delivering relatively low voltage pacing pulses in some configurations, e.g., for delivering rate response pacing pulses. Electrodes 162 and 164 are referred to as pace/sense electrodes because they are generally configured for use in low voltage applications, e.g., used as either a cathode or anode for delivery of pacing pulses and/or sensing of cardiac electrical signals, as opposed to delivering high voltage CV/DF shocks. In some instances, electrodes 162 and 164 may provide only pacing functionality, only sensing functionality or both.

ICD 112 may obtain cardiac electrical signals corresponding to electrical activity of heart 8 via a combination of sensing electrode vectors that include combinations of electrodes 162, 164, 166 and/or 168. In some examples, housing 115 of ICD 112 is used in combination with one or more of electrodes 162, 164, 166 and/or 168 in a sensing electrode vector. In the example illustrated in FIGS. 3A-3C, electrode 162 is located proximal to defibrillation electrode 166, and electrode 164 is located between defibrillation electrodes 166 and 168. One, two or more pace/sense electrodes (or none) may be carried by lead body 118 and may be positioned at different locations along distal lead portion 125 than the locations shown. Electrodes 162 and 164 are illustrated as ring electrodes; however, electrodes 162 and 164 may comprise any of a number of different types of electrodes, including ring electrodes, short coil electrodes, hemispherical electrodes, directional electrodes, segmented electrodes, or the like.

In some examples, lead body 118 may carry an accelerometer 182 and/or a second sensor 184 for sensing signals correlated to patient physical activity and metabolic demand. Accelerometer 182 is shown positioned toward the distal end of lead 116. Accelerometer 182 may be positioned in a substernal location when carried along the distal portion 125 of lead 116; however, accelerometer 182 may be carried anywhere along the length of lead body 118, including relatively more proximal portions of lead body 118 that may be outside the thoracic cavity. Accelerometer 182 may be located in a subcutaneous or submuscular location when located more proximally along lead body 118. Accelerometer 182 may produce acceleration signal correlated to patient physical activity for use in controlling rate response pacing. When accelerometer 182 is located more distally along lead body 118, e.g., in a substernal location generally over heart 8, cardiac motion may contribute to the acceleration signal. Increased cardiac motion at increased pacing rates and during exercise may lead to increasing or sustained high patient activity metrics determined from the acceleration signal, which could lead to a sustained high rate response pacing rate.

The second sensor 184 may be a temperature sensor carried by lead body 118. The temperature sensor 184 may be carried by the distal portion 125 of lead body 118 so that the temperature sensor is advanced to a substernal position, within the thoracic cavity. In this location, the temperature sensor 184 may sense core body temperature, which may increase and decrease in relation to patient physical activity. As such, temperature sensor 184 may provide a second signal that is responsive to changes in patient physical activity without being affected by cardiac motion. While temperature sensor 184 is shown positioned between defibrillation electrodes 166 and 168, temperature sensor 184 may be positioned at other locations along distal portion 125. Furthermore, in some examples, temperature sensor 184 is not required to be along the distal portion 125 and may be located at relatively more proximal portions of lead body 118 or even within or on housing 115. When located more proximally on lead body 118 or in or on housing 115, temperature sensor 184 may be located submuscularly or subcutaneously outside the thoracic cavity. The body temperature signal from temperature sensor 184 outside the thoracic cavity may still provide an acceptable response to changes in patient physical activity and metabolic demand for use in combination with an acceleration signal for controlling rate response pacing.

Electrical conductors (not illustrated) extend through one or more lumens of the elongated lead body 118 of lead 116 from the lead connector at the proximal lead end 127 to electrodes 162, 164, 166, 168, accelerometer 182 and temperature sensor 184. Elongated electrical conductors contained within the lead body 118, which may be separate respective insulated conductors within the lead body 118, are each electrically coupled with respective defibrillation electrodes 166 and 168 and pace/sense electrodes 162 and 164 as well as accelerometer 182 and temperature sensor 184. The respective conductors electrically couple the electrodes 162, 164, 166, 168 to circuitry, such as a therapy delivery circuit and/or a sensing circuit, of ICD 112 via connections in the connector assembly 117, including associated electrical feedthroughs crossing housing 115. The electrical conductors transmit therapy from a therapy delivery circuit within ICD 112 to one or more of defibrillation electrodes 166 and 168 and/or pace/sense electrodes 162 and 164 and transmit cardiac electrical signals from the patient's heart 8 from one or more of electrodes 162, 164, 166, 168 to the sensing circuit within ICD 112. Electrical conductors coupled to accelerometer 182 and temperature sensor 184 may provide power to the sensors as needed to turn on the sensors for sensing acceleration and temperature, respectively, and transmit the acceleration signal and the temperature signal from the accelerometer 182 and temperature sensor 184 to circuitry within housing 115 for processing and analysis. In other examples, accelerometer 182 may be contained within or on housing 115 of ICD 112 and temperature sensor 184 may be carried by lead body 118. In still other examples, both accelerometer 182 and a second sensor for controlling rate response may be contained within or on housing 115 of ICD 112.

The lead body 118 of lead 116 may be formed from a non-conductive material, including silicone, polyurethane, fluoropolymers, mixtures thereof, and/or other appropriate materials, and shaped to form one or more lumens within which the one or more conductors extend. Lead body 118 may be tubular or cylindrical in shape. In other examples, the distal portion 125 (or all of) the elongated lead body 118 may have a flat, ribbon or paddle shape. Lead body 118 may be formed having a preformed distal portion 125 that is generally straight, curving, bending, serpentine, undulating or zig-zagging. In the example shown, lead body 118 includes a curving distal portion 125 having two "C" shaped curves, which together may resemble the Greek letter epsilon, "ϵ." The techniques disclosed herein are not limited to any particular lead body design, however. In other examples, lead body 118 is a flexible elongated lead body without any pre-formed shape, bends or curves.

ICD 112 analyzes the cardiac electrical signals received from one or more sensing electrode vectors to monitor for abnormal rhythms, such as bradycardia, ventricular tachycardia (VT) or ventricular fibrillation (VF). ICD 112 may analyze the heart rate and morphology of the cardiac electrical signals to monitor for tachyarrhythmia in accordance with any of a number of tachyarrhythmia detection techniques. ICD 112 generates and delivers electrical stimulation therapy in response to detecting a tachyarrhythmia (e.g., VT or VF) using a therapy delivery electrode vector which may be selected from any of the available electrodes 162, 164, 166, 168 and/or housing 115. ICD 112 may deliver ATP in response to VT detection and in some cases may deliver ATP prior to a CV/DF shock or during high voltage capacitor charging in an attempt to avert the need for delivering a CV/DF shock. If ATP does not successfully terminate VT or when VF is detected, ICD 112 may deliver one or more CV/DF shocks via one or both of defibrillation electrodes 166 and 168 and/or housing 115. ICD 112 may generate and deliver other types of electrical stimulation pulses such as post-shock pacing pulses, asystole pacing pulses, or bradycardia pacing pulses, including rate response pacing pulses, using a pacing electrode vector that includes one or more of the electrodes 162, 164, 166, 168 and the housing 115 of ICD 112.

ICD 112 is shown implanted subcutaneously on the left side of patient 102 along the ribcage 132. ICD 112 may, in some instances, be implanted between the left posterior axillary line and the left anterior axillary line of patient 102. ICD 112 may, however, be implanted at other subcutaneous or submuscular locations in patient 102. For example, ICD 112 may be implanted in a subcutaneous pocket in the pectoral region. In this case, lead 116 may extend subcutaneously or submuscularly from ICD 112 toward the manubrium of sternum 22 and bend or turn and extend inferiorly from the manubrium to the desired location subcutaneously, submuscularly, substernally, over or beneath the ribcage 132. In yet another example, ICD 112 may be placed abdominally.

While ICD 112 is shown coupled to a non-transvenous lead 116 positioned in an extra-cardiovascular location, in other examples ICD 112 may be coupled to a transvenous lead that positions electrodes within a blood vessel but may remain outside the heart in an "extra-cardiac" location. For example, a transvenous medical lead may be advanced along a venous pathway to position electrodes within the internal thoracic vein (ITV), an intercostal vein, the superior epigastric vein, or the azygos, hemiazygos, or accessory hemiazygos veins, as examples. A transvenous medical lead, which may remain within a vein or be advanced within the heart 8, may carry one or more electrodes, an accelerometer, and/or a second sensor such as a temperature sensor for sensing a signal correlated to patient physical activity for use in controlling rate response pacing.

IMD system 100 is shown including pacemaker 12, shown implanted within the right ventricle in FIG. 3A. In some examples, pacemaker 12 is provided for delivering cardiac pacing therapy to heart 8, including rate response pacing, and ICD 112 is provided for detecting tachyarrhythmia and delivering CV/DF shocks. In this case, ICD 112 may or may not provide cardiac pacing therapy. Pacemaker 12 may include an accelerometer for sensing an acceleration signal used for determining a patient activity metric as described above and may include a second sensor, e.g., a temperature sensor, for controlling rate response pacing. ICD 112 may be configured to sense an accelerometer signal and/or a temperature signal, e.g., from respective accelerometer 182 and/or a temperature sensor 184 carried by lead 116 or enclosed by housing 115. ICD 112 and pacemaker 12 may be configured for bi-directional communication via telemetry link 124. ICD 112 may transmit activity metric data or activity-related notifications based on activity metrics determined from an accelerometer included on lead 116 or enclosed in ICD housing 115, e.g., as described below in conjunction with FIG. 11. For example, ICD 112 may determine a mismatch between a patient activity metric determined from an accelerometer signal and a sensed heart rate. ICD 112 may transmit an activity metric signal or related notification to pacemaker 12. Pacemaker 12 may be configured to enable temperature signal sensing based on an activity metric signal received from ICD 112 or make other adjustments to rate response pacing control.

Additionally or alternatively, ICD 112 may transmit temperature data or temperature related notifications to pacemaker 12. Due to size and power constraints, pacemaker 12 may include only an accelerometer and ICD 112 may include a second sensor, such as a temperature sensor. Pacemaker 12 may be configured to adjust the rate response pacing rate and/or adjust an SIR determined from its own accelerometer signal based on temperature related data received from ICD 112. As such, an IMD system, such as system 100, may perform the techniques disclosed herein in a distributed manner across one or more devices configured to sense an acceleration signal and at least one additional sensor signal, such as temperature, and providing rate response pacing with coordinated control based on both the acceleration signal and the second sensor signal.

Figure 4:
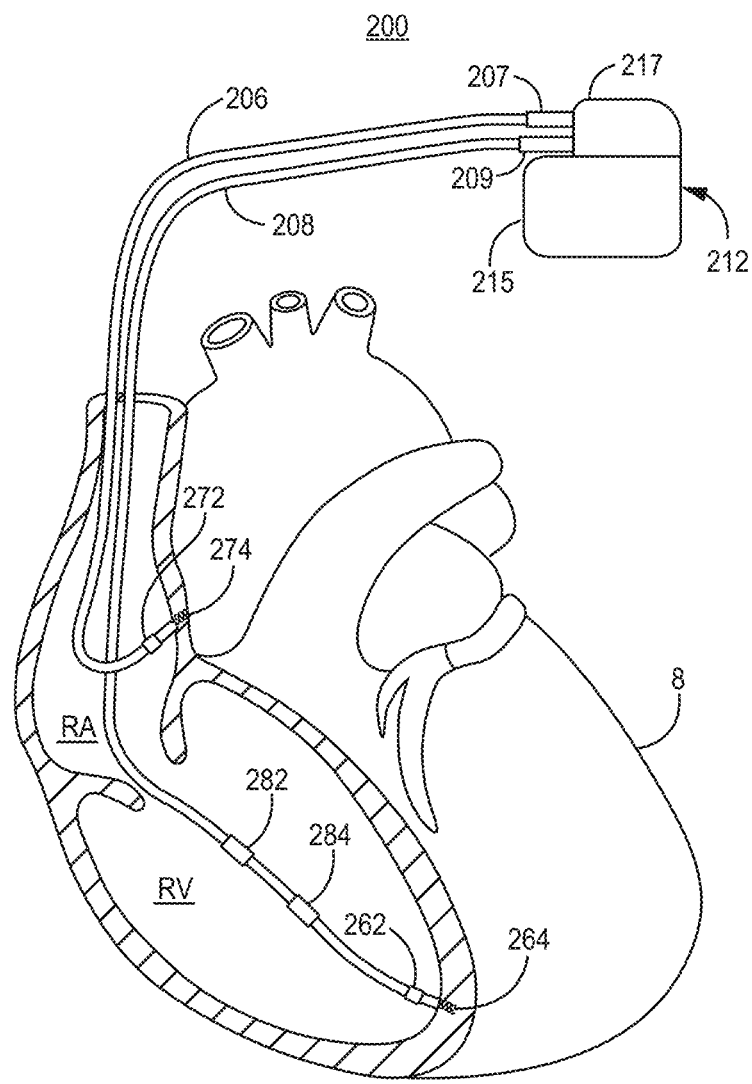
FIG. 4 is a conceptual diagram of an IMD system including a pacemaker capable of providing rate response pacing and sensing cardiac electrical signals and sensor signals via transvenous leads.

FIG. 4 is a conceptual diagram of an IMD system 200 including a pacemaker 212 capable of pacing a patient's heart 8 and sensing cardiac electrical signals and patient activity signals according to another example. Techniques disclosed herein are not necessarily limited to an IMD system that includes a leadless pacemaker, such as pacemakers 12 or 14 shown in FIG. 1. The disclosed techniques may be performed a medical device coupled to non-transvenous leads, such as ICD 112 shown in FIGS. 3A-3C as described above, or a medical device coupled to transvenous leads, such as pacemaker 212 coupled to one or more transvenous leads 206 and/or 208 as shown in FIG. 4.

The system 200 includes a pacemaker 212 coupled to a patient's heart 8 via at least one transvenous medical electrical lead 206 and/or lead 208. Pacemaker housing 215 encloses internal circuitry corresponding to the various circuits and components, for example as generally described below in conjunction with FIG. 5, for sensing cardiac electrical signals from heart 8, sensing an acceleration signal and a second sensor signal, and controlling electrical stimulation therapy, e.g., rate response pacing therapy, delivered by pacemaker 212.

Pacemaker 212 includes a connector block 217 configured to receive the proximal ends of one or more leads 206 and/or 208. Each of leads 206 and 208 are advanced transvenously for positioning electrodes for sensing and stimulation of the atria and the ventricles, respectively. Atrial lead 206 may be positioned such that its distal end is in the right atrium (RA). Atrial lead 206 is equipped with pacing and sensing electrodes, shown as a tip electrode 274 and a ring electrode 272 spaced proximally from tip electrode 274. The electrodes 272 and 274 provide sensing and pacing in the RA and are each connected to a respective insulated conductor extending within the elongated body of atrial lead 206. Each insulated conductor is coupled at its proximal end to a connector carried by proximal lead connector 207, and thereby is electrically coupled to internal pacemaker circuitry via connector block 217.

Ventricular lead 208 may be positioned such that its distal end is in the right ventricle (RV). Ventricular lead 208 is equipped with pacing and sensing electrodes, shown as tip electrode 264 at the lead distal end and ring electrode 262 spaced proximally from tip electrode 264. The electrodes 262 and 264 provide sensing and pacing in the RV and are each connected to a respective insulated conductor extending within the elongated body of ventricular lead 208. Each insulated conductor is coupled at its proximal end to a connector carried by proximal lead connector 209, and thereby electrically coupled to internal pacemaker circuitry via connector block 217.

Pacemaker 212 is shown as a dual chamber device capable of sensing cardiac signals and delivering pacing pulses in both an atrial chamber and a ventricular chamber. In other examples, pacemaker 212 may be configured as a single chamber device, e.g., coupled to only atrial lead 206 extending into the RA or only to ventricular lead 208 extending into the RV. In other examples, pacemaker 212 may be multi-chamber device including a third lead that may be advanced over the left ventricle within a cardiac vein via the coronary sinus. A multi-chamber pacemaker may be configured for delivering cardiac resynchronization therapy (CRT) in addition to rate response pacing.

While leads 206 and 208 are each shown carrying two electrodes, it is recognized that each lead may carry one or more electrodes for providing one or more pacing and/or sensing electrode vectors, which may include bipolar combinations of electrodes carried by the respective lead or unipolar combinations of an electrode carried by the respective lead and the pacemaker housing 215. In some examples, pacemaker 212 may be configured as an ICD capable of delivering both low voltage cardiac pacing therapies and high voltage CV/DF shocks. In this case, pacemaker 212 may be coupleable to at least one lead carrying at least one high voltage CV/DF electrode such as an elongated coil electrode.

Ventricular lead 208 is shown including an accelerometer 282 and a second sensor 284, which may be a temperature sensor. Accelerometer 282 may produce an acceleration signal that includes cardiac motion signals and patient body motion signals passed to circuitry enclosed by pacemaker housing 215 via an electrical conductor extending within the lead body to proximal connector 209. Accelerometer 274 may be a single or multi-axis accelerometer as described above. The acceleration signal from accelerometer 282 may be processed and analyzed by circuitry enclosed within housing 215 to determine a patient activity metric. As described above, a patient activity metric determined from an acceleration signal sensed within the heart may be elevated due to increased cardiac motion during exercise and rate response pacing at increased pacing rates and/or during a tachyarrhythmia. The elevated patient activity metric due to increased cardiac motion contributions may cause the pacing rate to remain higher longer than needed when patient activity actually decreases.

Accordingly, ventricular lead 208 may include a second sensor 284, which may be a temperature sensor, that produces a signal correlated to patient physical activity and is relatively less sensitive to cardiac motion than accelerometer 282. As described below, the second sensor signal and the accelerometer signal may be processed and analyzed by control circuitry within pacemaker 212 for controlling rate response pacing.

While ventricular lead 208 is shown carrying accelerometer 282 and second sensor 284, it is contemplated that atrial lead 206 may additionally or alternatively carry an accelerometer and/or a second sensor. When both leads 206 and 208 are included in the IMD system 200, one lead may carry accelerometer 282 and the other lead may carry the second sensor 284. When pacemaker 212 is coupled to a coronary sinus lead, the coronary sinus lead may carry an accelerometer and/or second sensor.

An IMD system configured to perform rate response pacing techniques disclosed herein may include pacemaker 212 coupled to atrial lead 206 and pacemaker 12 (as shown in FIG. 1) positioned in the RV. Atrial lead 206 may carry second sensor 284. Pacemaker 12 may provide rate response pacing based on an accelerometer signal. Pacemaker 212 may monitor temperature from second sensor 284 carried by atrial lead 206 and may transmit temperature-related data to pacemaker 12 for use in controlling rate response pacing according to techniques disclosed herein. In other examples, pacemaker 212 may include an accelerometer within pacemaker housing 215 and transmit an activity metric signal to pacemaker 12 (or pacemaker 14) when pacemaker 212 detects a mismatch between the activity metric and the sensed heart rate to trigger pacemaker 12 to enable temperature sensing for use in rate response pacing control.

Figure 5:
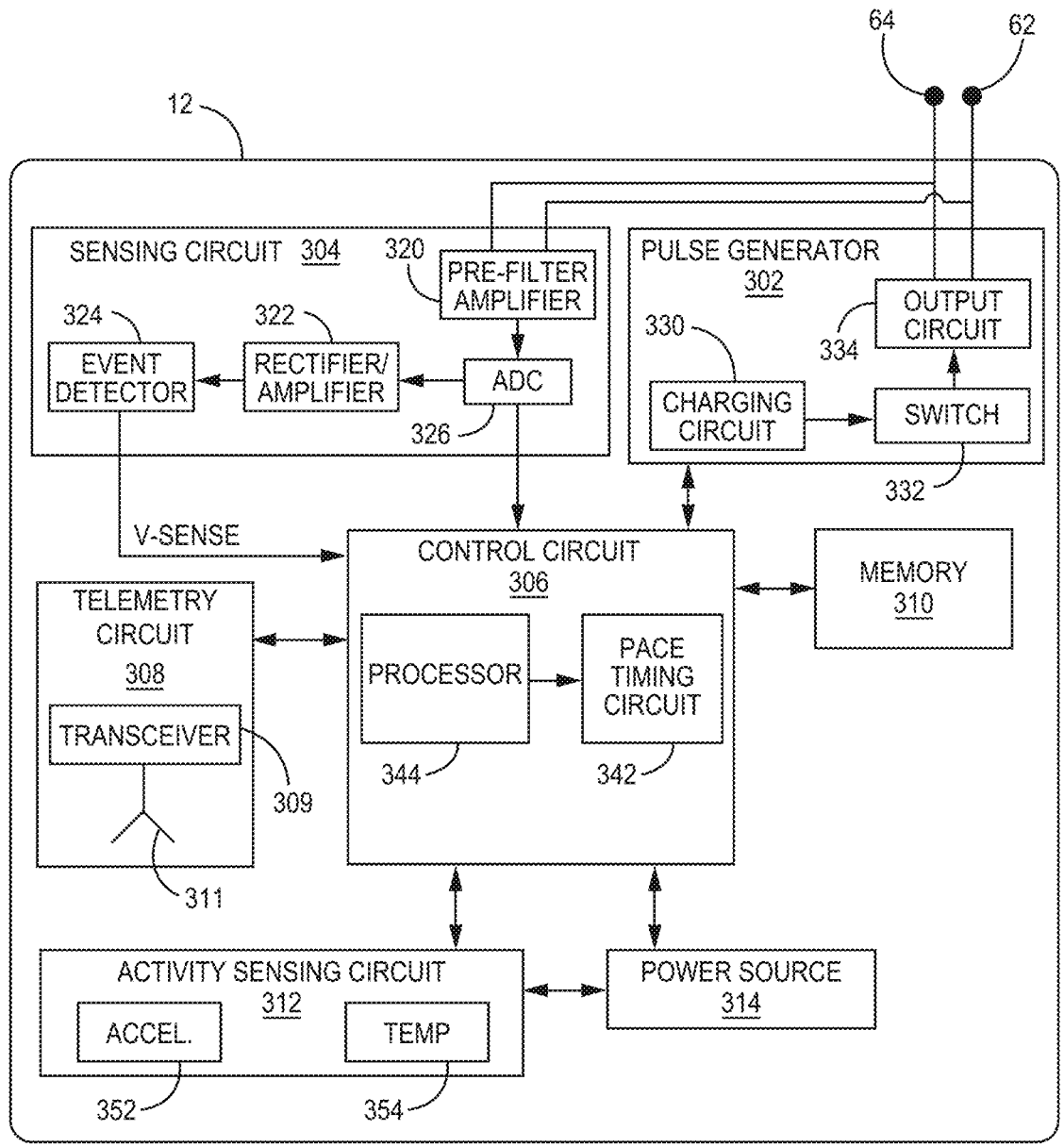
FIG. 5 is a conceptual diagram of an example configuration of a medical device configured to sense cardiac electrical signals and sensor signals for controlling rate response pacing according to one example.

FIG. 5 is a conceptual diagram of an example configuration of a medical device configured to sense cardiac signals and patient activity sensor signals and deliver rate response pacing according to one example. For the sake of convenience, FIG. 5 is described in the context of pacemaker 12 of FIG. 1; however it is to be understood that circuitry and components and the associated functionality generally described in conjunction with FIG. 5 and other flow charts and diagrams presented herein may be incorporated in pacemaker 14 shown in FIG. 1, ICD 112 shown in FIG. 4, or pacemaker 212 shown in FIG. 5.

Pacemaker 12 includes a pulse generator 302, a cardiac electrical signal sensing circuit 304, a control circuit 306, memory 310, telemetry circuit 308, activity sensing circuit 312, and a power source 314. The various circuits represented in FIG. 5 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Activity sensing circuit 312 may include an accelerometer 352 and a second sensor 354, shown as and referred to hereafter as temperature sensor 354. Examples of accelerometers that may be implemented in activity sensing circuit 312 include piezoelectric sensors and MEMS devices. Accelerometer 352 may be a single axis accelerometer or a multi-axis accelerometer, e.g., a two-dimensional or three-dimensional accelerometer, with each axis providing an axis signal that may be analyzed individually or in combination for sensing body motion. Accelerometer 352 produces an electrical signal correlated to motion or vibration of accelerometer 352 (and pacemaker 12), e.g., when subjected to flowing blood, cardiac motion and patient body motion.

One example of an accelerometer for use in implantable medical devices that may be implemented in conjunction with the techniques disclosed herein is generally disclosed in U.S. Pat. No. 5,885,471 (Ruben, et al.), incorporated herein by reference in its entirety. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers that may be implemented in pacemaker 12 and used for sensing acceleration signals are generally described in U.S. Pat. No. 5,593,431 (Sheldon) and U.S. Pat. No. 6,044,297 (Sheldon), both of which are incorporated herein by reference in their entirety. Other accelerometer designs may be used for producing an electrical signal that is correlated to motion imparted on pacemaker 12 due to patient body motion.

The activity sensing circuit 312 may include one or more filter, amplifier, rectifier, analog-to-digital converter (ADC) and/or other components for producing an acceleration signal that may be passed to control circuit 306 for use in determining a patient activity metric. For example, a vector signal produced by an individual axis of a multi-axis accelerometer may be filtered by a band pass or low pass filter, e.g., a 1-10 Hz bandpass filter or a 10 Hz low pass filter, digitized by an ADC and rectified for use by processor 344 of control circuit 306 for determining a patient activity metric.

Various activity metrics may be derived from the accelerometer signal by control circuit 306 that are correlated to patient activity. In the illustrative examples presented herein, the accelerometer-based activity metric derived from the accelerometer signal is obtained by integrating the absolute value of a selected accelerometer vector signal over a predetermined time duration (such as 2 seconds). For example, the selected accelerometer axis signal may be filtered by a 1-10 Hz bandpass filter, rectified and sampled at 128 Hz in one example. The amplitude of the sampled data points over a two-second interval may be summed to obtain the activity metric. This activity metric is referred to herein as an "activity count" and is correlated to the acceleration due to patient body motion imparted on the pacemaker 12 during the predetermined time interval. The 2-second (or other time interval) activity counts may be used by control circuit 306 directly to indicate patient activity for determining an SIR. In other examples, the activity count may be further processed, e.g., the 2-second interval activity counts may be averaged or summed over multiple intervals, to determine a patient activity metric for use in controlling rate response pacing.

Example techniques for determining activity counts are generally disclosed in commonly-assigned U.S. Pat. No. 6,449,508 (Sheldon, et al.), incorporated herein by reference in its entirety. In other examples, an activity count may be determined as the number of sample points of the accelerometer signal that are greater than a predetermined threshold during a predetermined time interval. The techniques disclosed herein are not limited to a particular method for determining a patient activity metric from the accelerometer signal and other methods may be used to determine the accelerometer-based activity metric.

Activity sensing circuit 312 includes temperature sensor 354 as a second sensor representative of metabolic demand for use in controlling rate response pacing. Temperature sensor 354 may include one or more temperature sensors, e.g., thermocouples or thermistors, configured to produce a signal correlated to temperature surrounding housing 15, e.g., correlated to venous blood within the RV. Temperature sensor 354 may be disposed internally within the housing 15 of pacemaker 12, contacting the housing, formed as a part of the housing, or disposed external of the housing 15. As described herein, temperature sensor 354 may be used to measure absolute or relative changes in temperature of blood/tissue surrounding and/or contacting the housing 15 of pacemaker 12. Processor 306 receives a temperature signal from activity sensing circuit 312 to detect changes in temperature, e.g., in the blood or core body temperature, that occur with changing metabolic demand during patient physical activity. Although a single temperature sensor may be adequate, multiple temperature sensors may be included in temperature sensor 354 to generate a more accurate temperature profile or average temperature signal. Control circuit 306 may continually sample the temperature signal at a desired sampling rate from temperature sensor 354. However, control circuit 306 may conserve energy from power source 314 by only sampling temperature when the activity metric or SIR determined from the acceleration signal is greater than a specified threshold. In other examples, control circuit 306 may increase the rate of sampling a temperature signal during specified ranges of the rate response pacing rates or specified ranges of the activity count or SIR determined from the activity count. Example techniques for controlling sampling of the temperature signal from activity sensing circuit 312 are described below.

While the second sensor included in activity sensing circuit 312 is shown as a temperature sensor 354, it is contemplated that that other types of sensors that are less sensitive to cardiac motion than accelerometer 352 and still produce a signal that is correlated to patient physical activity or metabolic demand may be included in activity sensing circuit 312 to provide second activity signal sensing. Another example of a second sensor that may be included in activity sensing circuit 312 is a blood oxygen saturation sensor for detecting changes in venous oxygen saturation within the RV or RA for instance, which may occur with changes in patient physical activity.

Activity sensing circuit 312 may be enclosed by the housing 15 (as shown in FIG. 5) of pacemaker 12. It is contemplated, however, that accelerometer 352 and/or temperature sensor 354 may be located on housing 15 in some examples, on an interior or exterior surface of housing 15. In the case of ICD 112 coupled to non-transvenous leads or in the case of pacemaker 212 coupled to transvenous leads and utilizing the techniques disclosed herein, the accelerometer and/or temperature sensor may be carried by the lead as described above and electrically coupled to activity sensing circuit 312 as an interface to control circuit 306.

Sensing circuit 304 is configured to receive at least one cardiac electrical signal via electrodes coupled to pacemaker 12, e.g., electrodes 62 and 64. While only electrodes 62 and 64 are shown in FIG. 5, it is to be understood that any housing-based electrodes and/or lead-based electrodes as shown in the example medical device configurations of FIGS. 1A-4 may be electrically coupled to circuitry depicted in FIG. 5. The cardiac electrical signal from electrodes 62 and 64 is received by a pre-filter and amplifier circuit 320. Pre-filter and amplifier circuit 320 may include a high pass filter to remove DC offset, e.g., a 2.5 to 5 Hz high pass filter, or a wideband filter having a bandpass of 2.5 Hz to 100 Hz or narrower to remove DC offset and high frequency noise. Pre-filter and amplifier circuit 320 may further include an amplifier to amplify the "raw" cardiac electrical signal passed to analog-to-digital converter (ADC) 326. ADC 326 may pass a multi-bit, digital electrogram (EGM) signal to control circuit 306 for use by control circuit 306 in identifying cardiac electrical events (e.g., sensed P-waves and/or sensed R-waves) or performing morphology analysis for detecting various cardiac arrhythmias. The digital signal from ADC 326 may be passed to rectifier and amplifier circuit 322, which may include a rectifier, narrow bandpass filter, and amplifier for passing a cardiac signal to cardiac event detector 324.

Cardiac event detector 324 may include a sense amplifier, comparator or other detection circuitry that compares the incoming rectified, cardiac electrical signal to a cardiac event sensing threshold, which may be an auto-adjusting threshold. For example, when the incoming signal crosses an R-wave sensing threshold, the cardiac event detector 324 produces a ventricular sensed event signal (V-sense) that is passed to control circuit 306. In other examples, cardiac event detector 324 may receive the digital output of ADC 326 for sensing R-waves by a comparator, waveform morphology analysis of the digital EGM signal or other R-wave sensing techniques.

Processor 344 may provide sensing control signals to sensing circuit 304, e.g., R-wave sensing threshold control parameters such as sensitivity and various blanking and refractory intervals applied to the cardiac electrical signal for controlling R-wave sensing. Ventricular sensed event signals passed from cardiac event detector 324 to control circuit 306 may be used for scheduling ventricular pacing pulses by pace timing circuit 342.

Control circuit 306 includes pace timing circuit 342 and processor 344. Control circuit 306 may receive ventricular sensed event signals and/or digital cardiac electrical signals from sensing circuit 304 for use in detecting and confirming cardiac events and controlling ventricular pacing. For example, ventricular sensed event signals may be passed to pace timing circuit 342 for starting a new ventricular pacing escape interval for use in controlling the timing of pacing pulses delivered by pulse generator 302. Processor 344 may include one or more clocks for generating clock signals that are used by pace timing circuit 342 to time out a pacing escape interval, e.g., a permanent lower rate pacing interval for treating bradycardia or a temporary lower rate interval for providing rate response pacing. The pacing escape interval may be restarted by pace timing circuit 342 in response to each cardiac electrical event, e.g., upon receipt of each ventricular sensed event signal and upon delivery of each ventricular pacing pulse by pulse generator 302.

When a ventricular sensed event signal is received by control circuit 306 before the pacing escape interval expires, pace timing circuit 342 may pass the time elapsed of the pacing escape interval to processor 344 as the cardiac event interval, e.g., an RR interval, between two consecutively sensed ventricular events. When a ventricular sensed event signal is not received by control circuit 306 before expiration of the pacing escape interval, pulse generator 302 generates a ventricular pacing pulse in response to the pacing escape interval expiration. The pacing escape interval is adjusted according to a rate response pacing rate that is set by control circuit 306 based on the accelerometer signal and the temperature signal according to the techniques disclosed herein.

It is to be understood that when the circuitry and components represented in FIG. 5 are included in RA pacemaker 14, sensing circuit 304 may be configured to produce an atrial sensed event signal in response to a sensed atrial electrical signal crossing a P-wave sensing threshold. The atrial sensed event signal is passed to control circuit 306 for use in controlling atrial pacing pulses and may be used in determining the atrial rate and detecting atrial tachyarrhythmias. When an atrial sensed event signal is not received by control circuit 306 before expiration of an atrial pacing escape interval, pulse generator 302 generates an atrial pacing pulse. The atrial pacing escape interval may be adjusted according to a rate response pacing rate set by control circuit 306 based on the accelerometer signal and temperature signal received from activity sensing circuit 312 according to techniques disclosed herein.

When an atrial sensed event signal is received before an atrial pacing escape interval expires, the PP interval from the most recent preceding atrial sensed event signal and the current atrial sensed event signal may be determined and compared to an atrial tachyarrhythmia detection interval. Control circuit 306 may count PP intervals falling into an atrial tachyarrhythmia detection interval zone for detecting atrial tachyarrhythmia. Control circuit 306 may be configured to detect tachyarrhythmia according to any tachyarrhythmia detection algorithm, which may include an analysis of sensed event intervals and/or cardiac electrical signal (e.g., EGM or ECG) signal morphology. In some examples, the acceleration signal received from accelerometer 352 may be used by control circuit 306 in detecting atrial tachyarrhythmia. As described in conjunction with FIG. 16, control circuit 306 may enable temperature change determination when atrial tachyarrhythmia is detected in order to avoid relying solely on the accelerometer signal for controlling rate response during atrial tachyarrhythmia, which may increase the cardiac motion signal contributions to the accelerometer signal.

Pulse generator 302 generates electrical pacing pulses according to the rate response pacing rate set by control circuit 306. The pacing pulses are delivered to the patient's heart via cathode electrode 64 and return anode electrode 62. Processor 344 may retrieve programmable pacing control parameters from memory 310, such as pacing pulse amplitude and pacing pulse width, which are passed to pulse generator 302 for controlling pacing pulse delivery. Pulse generator 302 may include charging circuit 330, switching circuit 332 and an output circuit 334. Charging circuit 330 is configured to receive current from power source 314 and may include a holding capacitor that may be charged to a pacing pulse amplitude under the control of a voltage regulator included in charging circuit 330. The pacing pulse amplitude may be set based on a control signal from control circuit 306. Switching circuit 332 may control when the holding capacitor of charging circuit 330 is coupled to the output circuit 334 for delivering the pacing pulse. For example, switching circuit 332 may include a switch that is activated by a timing signal received from pace timing circuit 342 upon expiration of a pacing escape interval and kept closed for a programmed pacing pulse width to enable discharging of the holding capacitor of charging circuit 330. The holding capacitor, previously charged to the pacing pulse voltage amplitude, is discharged across electrodes 62 and 64 (or other selected pacing electrode vector) through the output capacitor of output circuit 334 for the programmed pacing pulse duration. While not explicitly shown in FIG. 5, it is to be understood that when rate response pacing control techniques disclosed herein are implemented in a device, e.g., ICD 112, capable of delivering high voltage cardioversion/defibrillation shocks, pulse generator 302 may include high voltage capacitors that can be charged for delivering a high voltage shock under the control of control circuit 306.

Memory 310 may include computer-readable instructions that, when executed by control circuit 306, cause control circuit 306 to perform various functions attributed throughout this disclosure to pacemaker 12. The computer-readable instructions may be encoded within memory 310. Memory 310 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal.

Memory 310 may store patient activity metric and temperature data determined by control circuit 306 from signals from activity sensing circuit 312. Memory 310 may also store programmable control parameters and instructions executed by control circuit 306 for controlling rate response pacing. As described below, memory 310 may store control parameters used by control circuit 306 for determining a patient activity metric from the acceleration signal, determining an SIR from the activity metric and determining a rate response pacing rate based on the SIR and determined temperature change, and a transfer function used to control how fast or slow the rate response pacing rate is adjusted. In some examples, memory 310 stores a look-up table including rate response pacing rate adjustments according to determined changes in activity count and temperature.

Telemetry circuit 308 includes a transceiver 309 and antenna 311 for transferring and receiving data via a radio frequency (RF) communication link. Telemetry circuit 308 may be capable of bi-directional communication with external device 20 (FIG. 1) as described above. Acceleration signals, temperature signals, and cardiac electrical signals, and/or data derived therefrom, may be transmitted by telemetry circuit 308 to external device 20. Programmable control parameters and algorithms for sensing cardiac events and determining patient activity metrics from sensed signals for controlling pacing therapies delivered by pulse generator 302 may be received by telemetry circuit 308 and stored in memory 310 for access by control circuit 306.

Power source 314 provides power to each of the other circuits and components of pacemaker 12 as required. Power source 314 may include one or more energy storage devices, such as one or more rechargeable or non-rechargeable batteries. Power source 314 provides power to activity sensing circuit 312 as required for operating accelerometer 352 and temperature sensor 354. Control circuit 306 may control when power is supplied to temperature sensor 354 for producing a signal for controlling rate response pacing. When the temperature signal is not needed, e.g., when the accelerometer-based patient activity metric indicates a resting state, temperature sensor 354 may be powered down or powered for sampling the temperature signal at a relatively lower sampling rate to obtain a baseline, resting temperature signal in some examples. The connections between power source 314 and other pacemaker circuits and components are not explicitly shown in FIG. 5 for the sake of clarity but are to be understood from the general block diagram of FIG. 5. For example, power source 314 may provide power as needed to charging and switching circuitry included in pulse generator 302; amplifiers, ADC 326 and other components of sensing circuit 304; telemetry circuit 308 and memory 310.

The functions attributed to pacemaker 12 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, determination of a rate response pacing rate based on signals received from activity sensing circuit 312 may be implemented in control circuit 306 executing instructions stored in memory 310. Providing software, hardware, and/or firmware to accomplish the described functionality in the context of any modern medical device, given the disclosure herein, is within the abilities of one of skill in the art.

Figure 6:
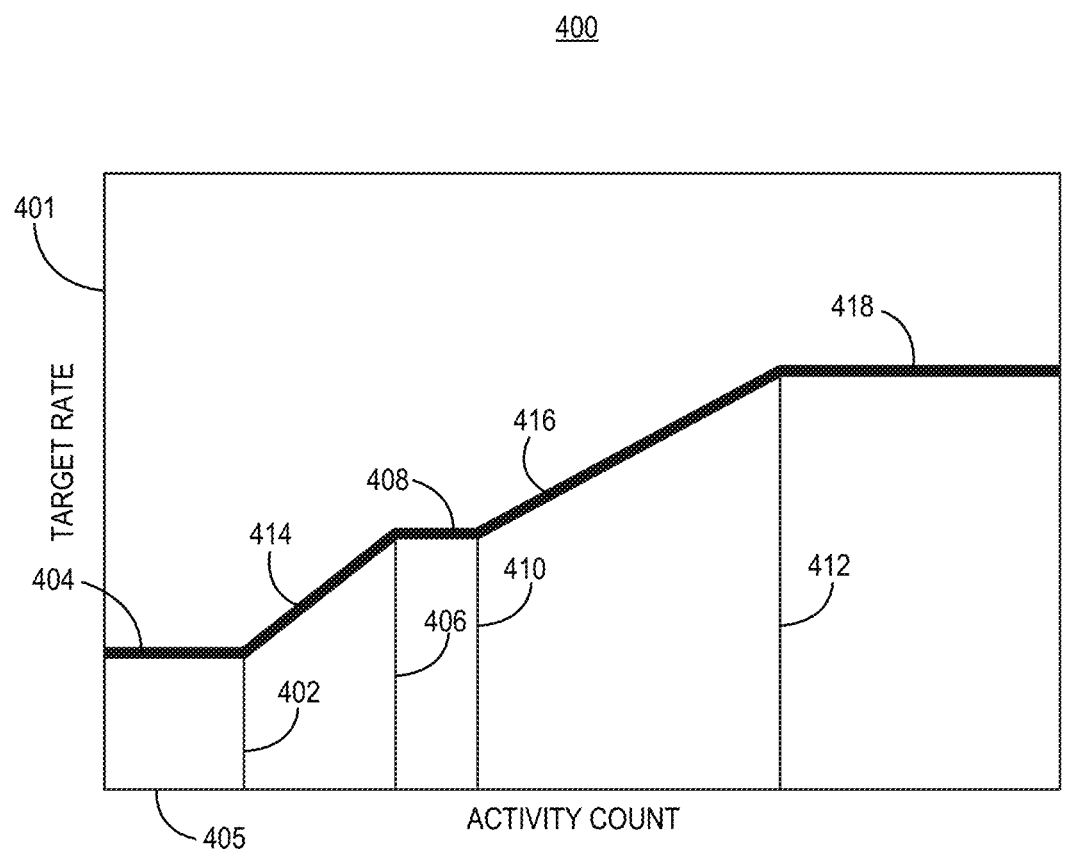
FIG. 6 is a plot of a transfer function that may be used by the medical device of FIG. 5 to control the pacing rate based on signals from an activity sensing circuit.

FIG. 6 is a plot 400 of a transfer function that may be used by control circuit 306 to control the pacing rate based on signals from activity sensing circuit 312 according to one example. As patient activity level changes, pacing rate is adjusted toward the target SIR determined from the activity counts (or other acceleration signal activity metric) according to a rate response transfer function, such as the function shown in the plot of FIG. 6. The transfer function is used to convert an activity metric to an SIR, which is the target pacing rate. However, control circuit 306 does not always adjust the pacing rate directly to the SIR to avoid abrupt changes in pacing rate. Rather, control circuit 306 can adjust the pacing rate toward the SIR according to a maximum rate of change, which may be controlled according to rate deceleration and rate acceleration rate control parameters in some examples. Activity metric thresholds, or "set points," may be used for determining the target SIR over activity count ranges corresponding to resting levels of activity, activity count ranges corresponding to activities of daily living (ADL) and activity counts corresponding to maximum activity or exertion. The rate response transfer function determines how quickly the target SIR rate is increased or decreased between these set points based on slopes 414 and 416 in the example of FIG. 6.

In plot 400, the target SIR is plotted along the y-axis 401 as a function of activity count plotted along the x-axis 405. The pacing lower rate (LR) 404 is the minimum pacing rate at which pulse generator 304 will generate pacing pulses in the absence of sensed R-waves. The LR is a predetermined minimum cardiac pacing rate which may be programmed by a user. The LR 404 is the pacing rate set by control circuit 306 when activity counts are equal to or less than the LR set point 402, indicating a resting level of patient activity that does not require an increase in heart rate. The pacing LR 404 may be programmable by a user, e.g., between 40 and 70 pulses per minute, and may be set to a default rate of 60 pulses per minute as an example. LR set point 402 may be programmed by a user and may be between 15 and 45, or about 20 in one example. In various examples, the LR set point may be 18, 32 or 42, for instance, when the maximum range of the activity count is 255 determined as the summation of the acceleration signal amplitudes sampled at 128 Hz over a two second time interval and scaled by dividing by 32. The LR set point 402 may be selected to discriminate between activity counts that occur due to cardiac motion when the patient is at rest and activity counts that occur when the patient is physically active. The value of the LR set point and other set points described herein will depend on the patient activity metric being determined, the sampling rate of the acceleration signal (e.g., 64 Hz, 128 Hz, 256 Hz, 512 Hz or other selected sampling rate), the time interval (e.g., one second, two seconds, three seconds, etc.) over which the activity count (or other metric) is being determined, any scaling factor, and/or other parameters used for determining the activity metric. As such, the example values of set points provided herein are given as illustrative examples of relative set points used to convert a patient activity metric to an SIR.

In some examples, control module 306 may establish or adjust the LR set point 402 based on a historical analysis of the activity counts determined by control circuit 306 to promote pacing at the LR 404 an expected percentage of the time, e.g., over a 24-hour period, corresponding to the percentage of time that the patient is expected to be at rest (or engaged in a physical activity level that is less than the ADL). Control circuit 306 does not increase the pacing rate above the LR 404, sometimes referred to as the "base pacing rate," as long as the activity count is at or below the LR set point 402. Control circuit 306 may use only the activity count determined from accelerometer 252 for determining the target SIR when the activity counts are less than the LR set point 402. To conserve power, the temperature sensor may be disabled when activity counts are less than the LR set point 402. In other examples, the temperature sensor may be powered on to determine a baseline temperature at a relatively low sampling rate, e.g., a few times per minute, once per minute, once per hour or other selected baseline monitoring rate, for as long as the activity count is less than the LR set point 402. In still other examples, the temperature sensor may be powered on according to a continuous sampling rate for monitoring a temperature signal, e.g., once per second, once every two seconds, every ten seconds, every thirty seconds, every minute or other specified sampling rate. In some examples, when the temperature signal is sampled at a continuous rate, processing by control circuit 306 for determining a temperature change may be performed less frequently when the activity count is low, e.g., less than the ADL set point.

An ADL pacing rate 408 may be programmed by a user or established by control circuit 306 as the target SIR when the activity counts determined from the accelerometer signal fall within an ADL range, e.g., between lower ADL set point 406 and upper ADL set point 410. The ADL rate 408 is the targeted pacing rate when the patient is expected to be engaged in normal daily activities or moderate activity, such as moving about the house, driving a car, light chores, etc. The ADL pacing rate 408 may be in the range of 70 pulses per minute to 110 pulses per minute as examples. A default ADL pacing rate may be 95 pulses per minute. An example lower ADL set point 406 is between 30 and 50 or about 40 when the activity count is determined as a two second integral of the accelerometer signal sampled at 128 Hz and divided by 32. An example upper ADL set point 410 is between 30 and 50 or between 30 and 60. In illustrative examples, with no limitation intended, the lower ADL set point is 31, 40 or 50. The respective upper ADL set point may be 45, 50 or 60, as examples. As generally disclosed in U.S. Pat. No. 10,518,094 (Sheldon, et al.), the various set points described in conjunction with FIG. 6 may be adjustable by control circuit 306. The '094 patent is incorporated herein by reference in its entirety.

When the activity count falls between the LR set point 402 and the lower ADL set point 406, pace timing circuit 342 adjusts the pacing rate (by adjusting the pacing escape interval) according to slope 414 between LR 404 and ADL rate 408. Slope 414 represents the maximum rate of increasing (or decreasing) the pacing rate toward an SIR. When the activity count reaches the ADL range between lower ADL set point 406 and upper ADL set point 410, control circuit 306 adjusts the pacing rate no faster than the slope 414, for example, to avoid abrupt changes in pacing rate. As a result, the actual pacing rate may be different than the target SIR rate as the pacing rate is being adjusted toward the target SIR rate.

An upper rate (UR) set point 412 corresponds to a high level of patient activity, e.g., strenuous exercise or physical work that is greater than the ADL. When the activity counts determined from the accelerometer signal are greater than the UR set point 412, control circuit 306 sets the rate response pacing rate to the maximum UR 418. UR 418 may be programmed by a user and represents the maximum rate that pulse generator will generate and deliver pacing pulses. The maximum UR 418 may be 120 to 180 pulses per minute and is 150 pulses per minute as an example. When the activity count is greater than the upper ADL set point 410, control circuit 306 adjusts the pacing rate from the ADL rate 408 toward the target SIR according to slope 416, up to the maximum UR 418. The UR set point 412 may be programmable by a user between 50 and 80 and is set to 62 as a default value in one example. As the activity count varies between the upper ADL set point 410 and the UR set point 412, control circuit 306 may adjust the pacing rate up or down toward the target SIR according to slope 416.

The LR set point 402, the lower ADL set point 406, the upper ADL set point 410, and the UR set point 412 may all be adjusted by control circuit 306 based on monitored activity counts in some examples. For example, the lower ADL set point 406 may be adjusted based on a patient's monitored activity counts over time. Trends and averages of the activity counts determined over 24 hour periods, as an example, may be used to generate a patient activity profile for setting the LR set point 402, lower ADL set point 406 and the upper ADL set point 410, and/or the UR set point 412 based on daily or other longer-term histograms of activity counts. Control circuit 306 may adjust the set points 402, 406, 410 and/or 412 to predetermined percentiles of historical activity counts acquired daily or over longer periods of time, so that the percentage of time that the LR 404, ADL rate 408 and/or UR 418 pacing rates are delivered over the course of a day correspond to the respective percentage of time that the patient is expected to be resting, engaged in ADL, and/or engaged in strenuous exertion.

While both a lower ADL set point 406 and upper ADL set point 410 are shown in the example of FIG. 6, in some examples a single ADL set point may be used to control the rate response pacing rate according to a first slope 414 between the LR 404 and the ADL rate 408 (associated with an SIR at the ADL set point) and a second slope 416 between the ADL rate 408 and the maximum upper rate 418. The single ADL set point may be programmable and set in the range of 30 to 50, as examples. For example, if upper ADL setpoint 410 is excluded, control circuit 206 may set the target SIR rate at the LR 404 when activity count is less than the LR set point 402, increase the target SIR rate to the ADL rate 408 when the activity count is at the single ADL set point 406, and increase the SIR to the maximum UR 418 when the activity count is greater than the upper rate set point 412.

As described below, each of the lower rate set point 402, ADL set points 406 and 410, and upper rate set point 412 may be adjusted in order to adjust the rate response pacing rate depending on combinations of activity count changes and temperature changes. For example, the lower rate set point 402 may be increased when the activity count increases above the lower rate set point 402 but temperature is not increasing. In the situation of atrial tachyarrhythmia occurring while the patient is at rest, the activity count may increase but no change in temperature due to the resting state of the patient may cause control circuit 306 to increase the lower rate set point 402. When the activity count decreases, the lower rate set point 402 may be decreased again. In this way, the pacing rate is not increased due to an increase in cardiac motion contributions to the acceleration signal during atrial tachyarrhythmia.

In other examples, control circuit 306 may increase the upper rate set point 412 when activity counts are not decreasing (e.g., activity counts are increasing or staying the same) but temperature is decreasing. When cardiac motion due to increased pacing rate is preventing the activity count from decreasing with decreasing patient activity, control circuit 306 may determine that physical activity is decreasing based on decreasing temperature. By increasing the upper rate set point 412, the SIR may be decreased even though the activity count has not decreased. As the rate response pacing rate is decreased, the cardiac contribution to the activity counts may decrease allowing the pacing rate to be appropriately adjusted downward as physical activity decreases or ceases.

Figure 7:
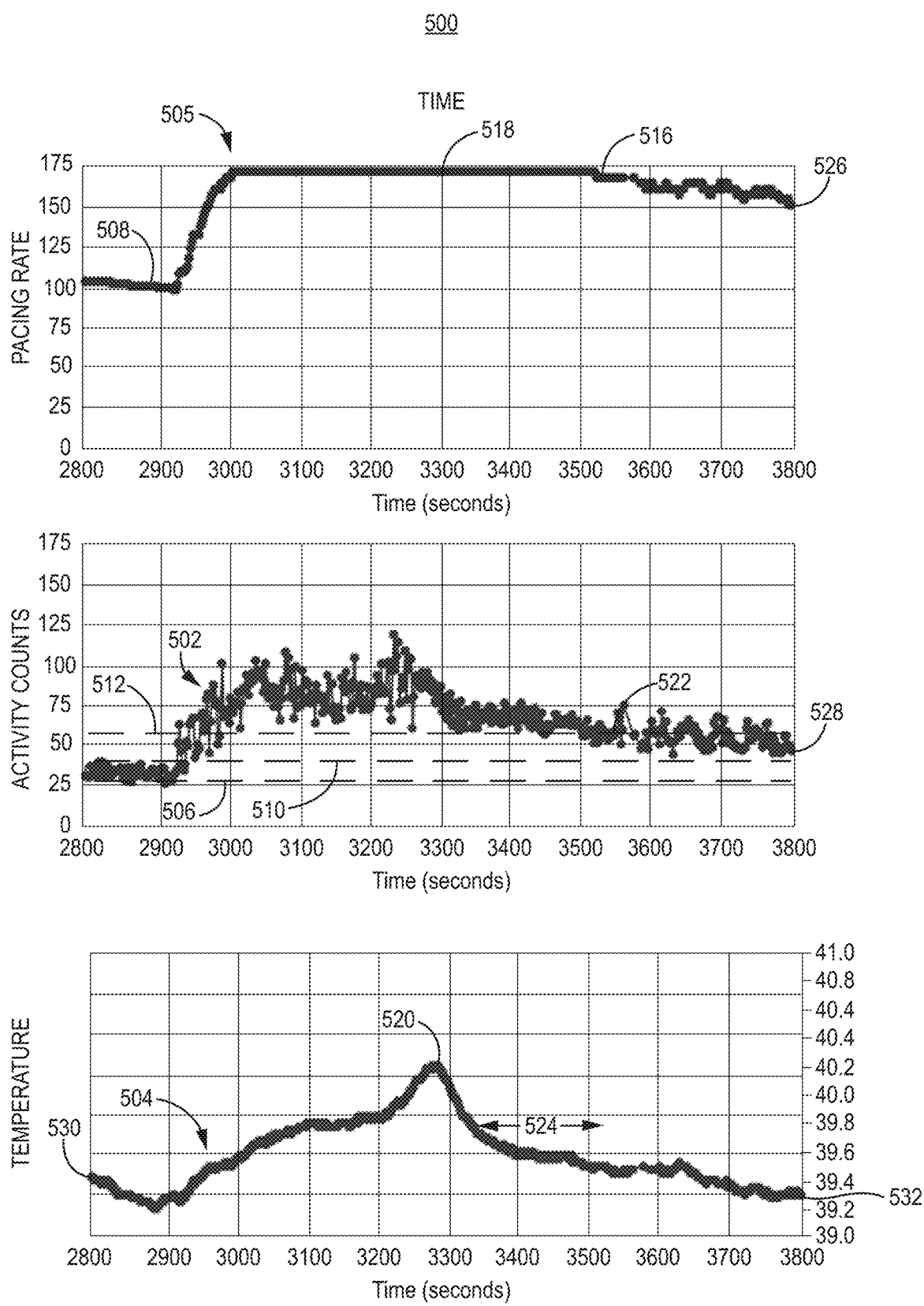
FIG. 7 is a plot of the rate response pacing rate delivered by a cardiac pacing device based on activity counts determined from an accelerometer signal produced within the patient's heart according to one example.

FIG. 7 is a plot 500 of the rate response pacing rate 505 controlled by control circuit 306 based on activity counts 502 according to one example. The rate response pacing rate 505 is adjusted based on activity counts determined from an accelerometer signal produced within the patient's heart according to a transfer function, such as the transfer function shown in FIG. 6, and within rate acceleration and deceleration limits. Plot 500 includes a graph of activity counts 502, temperature signal 504, and rate response pacing rate 505 over a time interval of approximately sixteen minutes. The activity counts 502 may be determined by control circuit 306 as two-second integrals of the accelerometer signal by summing the sample point amplitudes of the filtered, rectified accelerometer signal over each two-second time interval. The lower ADL set point 506, the upper ADL set point 510 and the maximum UR set point 512 are each shown relative to the plot of activity counts 502 by dashed lines. Initially, the activity counts 502 fall substantially between the lower ADL set point 506 and the upper ADL set point 510 such that an initial rate response pacing rate 505 remains substantially at the ADL rate 508, e.g., approximately 100 pulses per minute. It is to be understood that in some examples, a single ADL set point may be used such that the SIR is determined according to a first rate of change up to the ADL rate (from the programmed lower rate) and according to a second rate of change up to the upper rate (from the ADL rate). In this example, the patient may be initially engaged in moderate activities of daily living and then begins to engage in more strenuous activity.

As the activity counts 502 begin to increase above the upper ADL set point 510, the rate response pacing rate 505 increases. When the activity counts 502 exceed the UR set point 512, the rate response pacing rate 505 continues to increase toward the target SIR according to a maximum rate of increase. Upon reaching the maximum UR 518, the activity counts remain high, above the UR set point 512 until time point 522 when the rate response pacing rate 505 begins to decrease at 516. The activity counts 502, however, remain near the UR set point 512, above the upper ADL set point 510, until the end of the time segment shown by graph 500, such that the ending activity count 528 is greater than the upper ADL set point 510 and the ending rate response pacing rate 526 is still relatively high, greater than a default ADL rate of approximately 100 pulses per minute in this example. In this scenario, therefore, control circuit 306 adjusts the rate response pacing rate toward the maximum UR, e.g., 175 pulses per minute, and maintains the pacing rate at or near the maximum UR, above the ADL rate, when controlling the rate response pacing rate based solely on the activity counts 502.

Temperature 504 is observed to increase with activity counts 502 from a starting baseline temperature 530 up to a maximum peak temperature 520, after which temperature decreases. A time delay 524 is observed between a significant decrease in temperature 504 and when the rate response pacing rate 505 begins to decrease from the maximum UR 518 at time 516. The ending temperature 532 for the time segment shown by graph 500 has returned substantially to the starting baseline temperature 530. Accordingly, changes in temperature 504 suggest that the patient metabolic demand has decreased back to a level that may correspond to ADL by the end of the time segment shown by graph 500, yet the ending rate response pacing rate 526 remains high, nearer the maximum upper rate 518 than the ADL rate 508, based on the ending activity counts 528 remaining high, above the upper ADL set point 510.

This mismatch in the metabolic demand indicated by temperature 504 and the metabolic demand indicated by activity counts 502 may be due to increased cardiac motion contributing to the accelerometer signal. In this example, patient physical activity begins around 2930 seconds and ends around 3250 seconds. Temperature 504 increases throughout physical activity and continues to increase to a peak 520 after activity counts 502 begin to decrease. Temperature decreases back to an approximate baseline temperature 532, but activity counts 502 remain higher after activity ceases (at approximately 3250 seconds) than the activity counts before the onset of increased activity, which may be due to the increased cardiac motion contribution to the acceleration signal. This increased cardiac motion may be associated with both the high pacing rate and increased cardiac contractility associated with exercise.

In other examples, the increased cardiac motion may be due to atrial tachyarrhythmia, e.g., atrial tachycardia or atrial fibrillation, particularly when the pacemaker 14 is implanted in the right atrium. Atrial tachyarrhythmia may be present before an increase in patient physical activity and cause the SIR to increase to a target rate greater than needed to support the patient's actual physical activity level. In other instances, an atrial tachyarrhythmia may originate during patient physical activity and interfere with an appropriate decrease in rate response pacing rate as the patient's physical activity decreases.

Cardiac motion contributing to the activity counts 502 may cause the target SIR, and subsequently the rate response pacing rate 505, to remain high even after physical activity has decreased or ceased. The activity counts 502 are observed to decrease as temperature 504 decreases following the maximum peak temperature 520. Yet, since the rate response pacing rate 505 remains at or near the maximum UR, the cardiac contribution to the activity counts 502 creates a positive feedback loop that may cause the activity counts 502 to remain above the upper ADL set point 510 even after a reduction or cessation of physical activity, as suggested by the temperature signal 504.

A cardiac device delivering rate response pacing according to the techniques disclosed herein uses the temperature signal 504 to adjust the rate response pacing rate 505 during activity to avoid sustained periods of elevated pacing rates due to the cardiac motion contribution to the activity counts 502. For example, the temperature 504 may be used by control circuit 306 to adjust the pacing rate at least during activity that is greater than an ADL set point so that the pacing rate may be decreased by control circuit 306 as temperature 504 decreases, even when the SIR and activity counts 502 remain high. For example, the target SIR based on activity counts 502 may be adjusted based on temperature 504 or the delivered pacing rate may be adjusted directly based on the temperature signal 504 to allow the delivered pacing rate to be lower than the rate response rate determined according to the target SIR based only on activity counts.

In some examples, the upper ADL set point 510 (or a single ADL set point when used instead of upper and lower ADL set points) and/or the maximum UR set point 512 may be adjusted higher by control circuit 306 after the activity counts 502 become greater than the UR set point 512 if temperature 504 is detected to be decreasing. In this way, the activity counts 502 may fall below an adjusted UR set point 512 and/or fall below an adjusted upper ADL set point 52 more quickly when activity counts are decreasing but remain skewed high due to increased cardiac motion. By adjusting the UR set point 512 and/or an ADL set point upward in response to detecting a decrease in temperature 504 when the rate response pacing rate 505 is high, the rate response pacing rate 505 may return to a more appropriate pacing rate more quickly than when fixed setpoints 510 and 512 are used and the rate response pacing rate 505 is based solely on activity counts 502.

Figure 8:
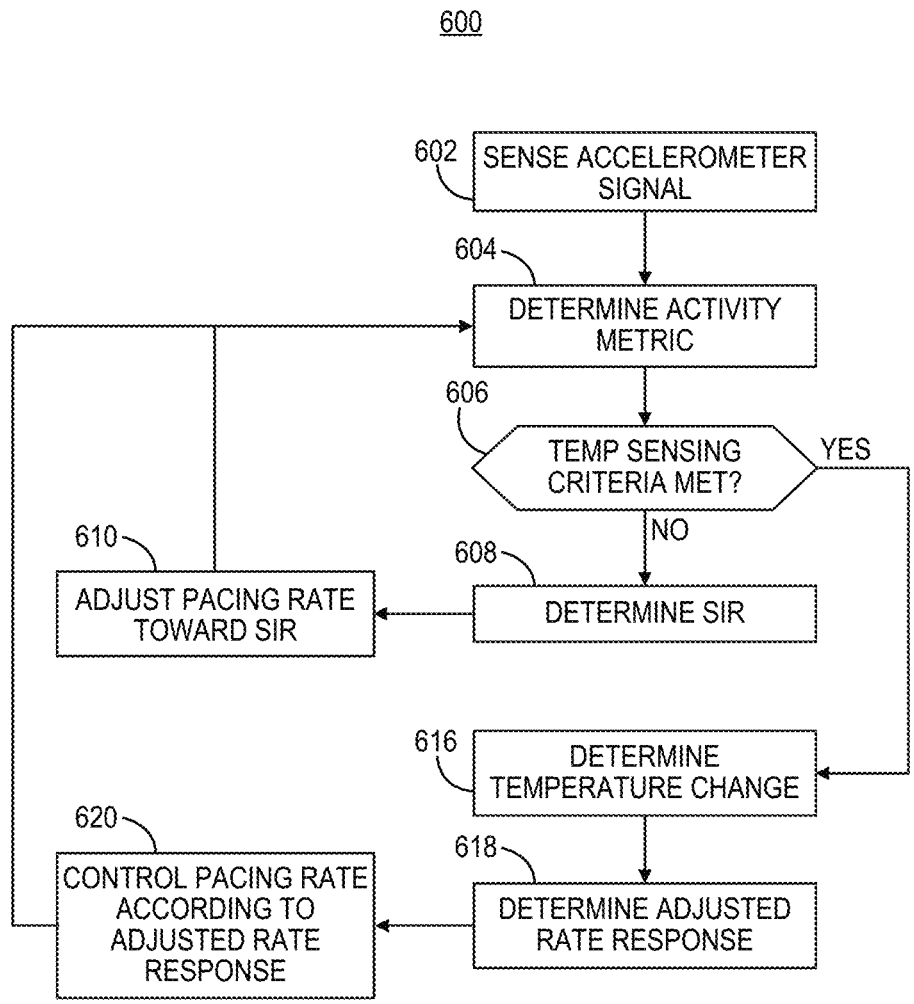
FIG. 8 is a flow chart of a method for controlling rate response pacing based on an accelerometer signal and a temperature signal according to one example.

FIG. 8 is a flow chart 600 of a method for controlling rate response pacing based on an accelerometer signal and a temperature signal according to one example. At block 602, activity sensing circuit 312 senses the accelerometer signal and may pass a filtered and rectified accelerometer signal to control circuit 306 for determining a patient activity metric at block 604. As described above, the patient activity metric determined from the accelerometer signal may be an activity count determined by integrating the rectified, low pass or band pass filtered acceleration signal in some examples.

At block 606, control circuit 306 may determine whether temperature sensing criteria are met based on the accelerometer signal and/or the actual pacing rate. For example, control circuit 306 may compare the patient activity metric to a threshold, the SIR to a threshold rate, or the actual pacing rate to a threshold rate. For instance, when the activity count is determined to be greater than or equal to the lower ADL set point or greater than or equal to the upper ADL set point (or greater than or equal to a single ADL set point), control circuit 306 may determine that temperature sensing criteria are met at block 606. In other examples, when the SIR or the actual pacing rate is greater than the ADL rate, control circuit 306 may determine that temperature sensing criteria are met. Other thresholds, higher or lower than the ADL set point(s) or ADL rate may be applied to the patient activity metric, SIR and/or actual pacing rate to trigger sensing of the temperature signal for use in controlling rate response. For instance, in RA pacemaker 14, when the activity count is greater than the LR set point, control circuit 306 may determine that temperature sensing criteria are met in order to avoid increasing pacing rate due to activity counts that are increased due to atrial tachyarrhythmia.

When the temperature sensing criteria are not met ("no" branch of block 606), the accelerometer signal may be relied upon for controlling pacing rate. For example, when the patient activity metric is less than a specified threshold, and subsequently the SIR and actual pacing rate are still relatively low, the cardiac motion contribution to the activity metric based on the accelerometer signal may be presumed to be insignificant for the purposes of controlling rate response.

At block 608, control circuit 306 determines the target cardiac pacing rate as the SIR based on the patient activity metric. The SIR may be updated based on each determination of the patient activity metric, e.g., after each 2-second activity count. In other examples, the SIR may be updated based on a mean or median activity count determined from multiple sequential activity counts, e.g., every three activity counts determined over six seconds, five activity counts determined over 10 seconds, ten activity counts determined over 20 seconds or other predetermined number of activity counts. At block 610, control circuit 306 adjusts the pacing rate (if needed) toward the SIR. When the SIR is at the LR or ADL rate and the pacing rate is already at the LR or ADL rate, respectively, no pacing rate adjustment is needed at block 610. When the pacing rate is greater than or less than the SIR, control circuit 306 adjusts the pacing rate toward the SIR according to a maximum rate of change as defined by a predetermined slope of the rate response transfer function, e.g., slope 414 of FIG. 6.

When the temperature sensing criteria are met at block 606, control circuit 306 may determine a temperature change at block 616 from the temperature signal received from activity sensing circuit 312. In some instances, the temperature change may be a change between a currently sampled temperature signal value and a most recent baseline temperature signal determined when the activity metric was less than the threshold. In other instances, the temperature change determined at block 616 may be determined as the change in the temperature signal over a specified time interval, e.g., one second, two seconds, five seconds, ten seconds, thirty seconds, one minute, two minutes, five minutes, ten minutes or other selected time interval. The temperature change may be determined by control circuit 306 by comparing a temperature sample point or an average of multiple temperature sample points determined at the beginning of the specified time interval to a temperature sample point or an average of multiple temperature sample points determined at the end of the specified time interval. The temperature change may be determined to be an increase (positive change when preceding temperature is subtracted from current temperature), a decrease (negative change when preceding temperature is subtracted from current temperature) or no change when the difference between the first and second temperatures is zero, e.g., within the resolution of the temperature sensor, or less than a change threshold. For example when the difference between the current temperature and the preceding temperature separated by a predetermined time interval (e.g., 30 seconds or more) is less than 0.05, 0.1, 0.15, 0.2, 0.5 degrees Celsius (C), or other specified threshold, the temperature may be determined to be non-changing. When the temperature difference is greater than the change threshold an increasing or decreasing temperature change is determined.

In some examples, control circuit 306 may determine the temperature change by determining a short-term moving average and subtracting the short-term moving average from a preceding short-term moving average. The short-term moving average may be determined by averaging the temperature signal sample points acquired over an averaging interval. For example, a short-term moving average may be determined by averaging temperature signal sample points acquired every 1 second, two seconds, 10 seconds, 30 seconds, or one minute over an averaging interval that is at least one minute long as examples. Since core body temperature is expected to increase and decrease relatively gradually, a temperature change may be determined as a difference in temperature after one minute, two minutes, five minutes or even ten minutes as examples.

In still other examples, the temperature change may be determined at block 616 by determining a threshold number of consecutive temperature differences that are trending in the same direction. For example, if the difference between the current temperature and a preceding temperature (where each of the current and preceding temperatures may be a single sample point of the temperature signal, a short-term average or a short-term moving average) is positive three consecutive times, an increasing temperature change may be determined at block 616. When the difference is negative three (or more) consecutive times, a decreasing temperature change may be determined at block 616. The individual differences may be any magnitude of change but the consecutive differences trending the same direction may be detected as an increasing or decreasing temperature change at block 616. When the three consecutively determined temperature differences include both positive and negative differences and/or zero differences, no temperature change may be detected by control circuit 306 at block 616. In this way, a threshold difference is not necessarily required in order to detect a temperature change, but a threshold number of consecutive temperature differences in the same direction indicate a rising or falling body temperature.

At block 618, control circuit 306 may determine an adjusted rate response pacing rate based on the determined temperature change. In some examples, control circuit 306 determines an adjusted rate response pacing rate based only on the temperature change and not based the accelerometer signal at block 618. In other examples, control circuit 306 determines the adjusted rate response pacing rate based on both the temperature signal and the accelerometer signal when the temperature sensing criteria are met at block 606.

At block 620, control circuit 306 controls the pacing rate according to the adjusted rate response pacing rate. For example, when control circuit 306 determines that the temperature change is an increase, control circuit 306 may increase the pacing rate from the current pacing rate to a second pacing rate, up to the programmed maximum UR, according to a maximum rate of increasing pacing rate. The pacing rate may be adjusted from the current pacing rate toward the SIR according to the slope 416 of FIG. 6.

If the temperature change is a decrease, control circuit 306 may decrease the pacing rate from the current pacing rate toward the ADL rate (or the LR) according to a maximum rate of decreasing the pacing rate, e.g., according to slope 416. These changes based on the temperature change when the activity metric is greater than or equal to the threshold may occur regardless of whether the patient activity metric is increasing, decreasing or staying the same. If control circuit 306 determines that the temperature has not changed, the pacing rate may be held at the current rate. Accordingly, control circuit 306 may adjust the rate response pacing rate at block 620 from a first rate to a second rate that may be higher, lower or equal to the first rate depending on the direction of the temperature change (or detecting no change) as determined at block 616.

In other examples, if the temperature change is decreasing at block 616, control circuit 306 may increase the maximum UR set point and/or an ADL set point and determine the adjusted rate response pacing rate based on a comparison of the activity counts to the adjusted set points. A lower SIR may be determined based on the increased set points, such that the rate response pacing rate is adjusted downward toward the lower SIR. As described below in conjunction with FIG. 10, control circuit 306 may determine whether to increase, decrease, or maintain the pacing rate based on both the acceleration signal and the temperature signal at block 618 and control the pacing rate accordingly at block 620.

In some examples, when the temperature is not increasing and the activity count is greater than the LR set point, control circuit 306 may adjust the rate response at block 618 by increasing the LR set point. As described above, an increase in the activity count above the LR set point may be caused by atrial tachyarrhythmia, particularly in pacemaker 14 implanted in the atrium. By increasing the LR set point, control circuit 306 may prevent an increase in pacing rate from the programmed lower rate until an increase in temperature and/or a relatively larger increase in activity counts that is most likely a true increase in patient physical activity is detected.

After adjusting the pacing rate at block 620, control circuit 306 may return to block 604 to determine the next activity metric from the acceleration signal. If the activity metric has decreased such that the temperature sensing criteria are unmet (block 606), the SIR may be determined at block 608, and control circuit 306 may adjust the pacing rate toward the SIR at block 610 without checking for a temperature change. If the temperature sensing criteria are still met at block 606, control circuit 306 determines the temperature change again at block 616 and continues to adjust the pacing rate (if needed) according to an adjusted rate response based on the temperature change. In this way, when the pacing rate is increased to a higher rate due to an increased activity metric and SIR, the temperature signal may be used by control circuit 306 to make pacing rate adjustments, particularly to decrease the rate response pacing rate from a rate greater than the ADL rate, to avoid prolonged pacing rates above the ADL rate due to cardiac motion contributions to the activity metric at the higher pacing rates.

Figure 9:
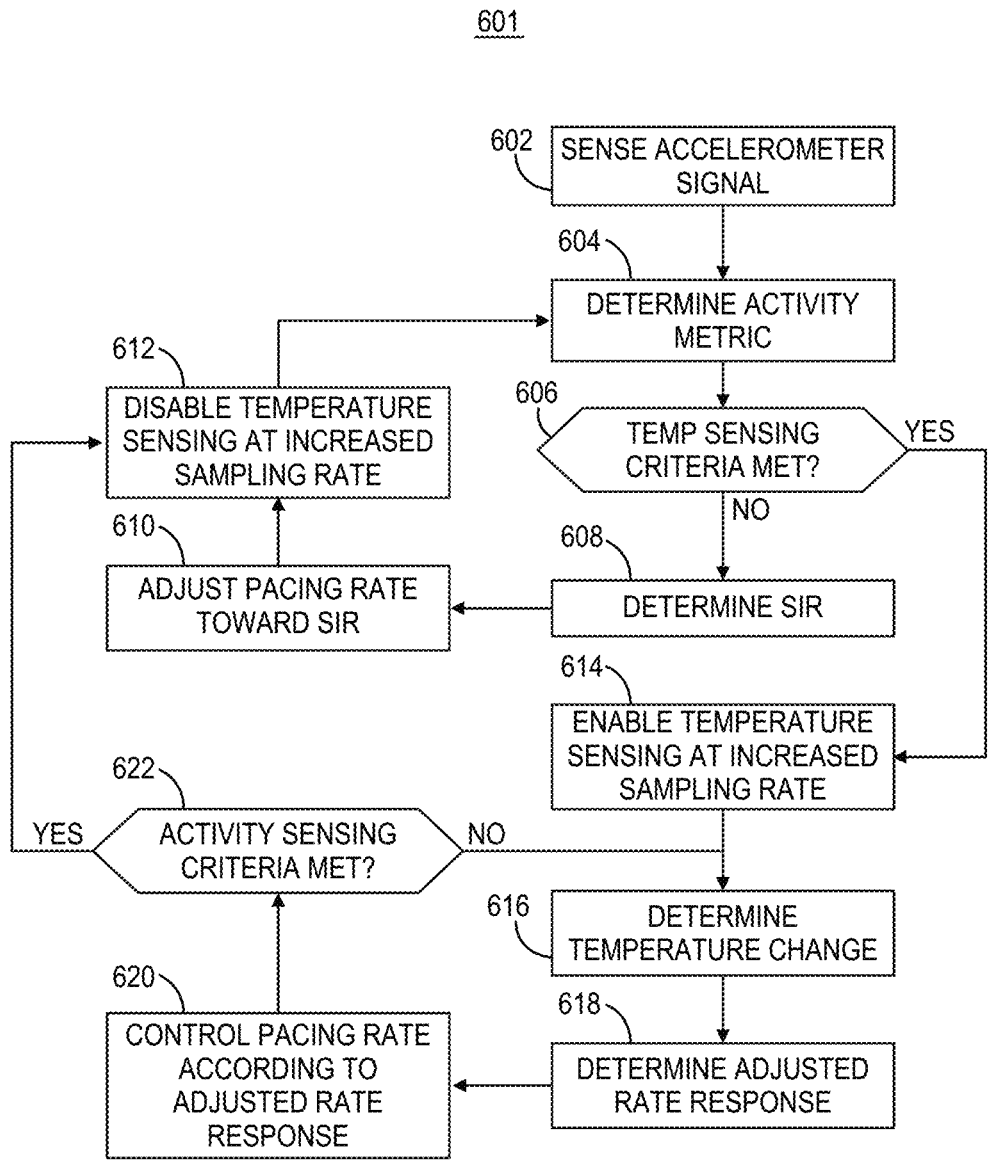
FIG. 9 is a flow chart of a method for controlling rate response pacing by a cardiac pacing device according to another example.

FIG. 9 is a flow chart 601 of a method for controlling rate response pacing by a cardiac pacing device according to another example. Identically numbered blocks in flow chart 601 correspond to like-numbered blocks shown in FIG. 9 as described above. In the process of flow chart 601, control circuit 306 may control when the accelerometer 352 and/or temperature sensor 354 are powered on and off (and/or how often the signals are processed for rate response control) to conserve power source 314 of pacemaker 12.

In some examples, accelerometer 352 may be powered on to enable sampling of the acceleration signal at a fixed sampling rate on an ongoing basis that allows two-second activity counts to be determined consecutively to detect changes in physical activity that may warrant a change in pacing rate. However, temperature sensor 354 may be powered on only when the temperature signal is needed (or processed only when a temperature change determination is needed), e.g., when the activity count, SIR and/or actual rate response pacing rate are greater than respective thresholds, when atrial tachyarrhythmia is detected or when other temperature sensing criteria are met, for use in controlling rate response pacing. The temperature sensor (or processing of the temperature signal) may be turned off to conserve power source 314 when temperature is not being used to control rate response.

In flow chart 601, the temperature sensor 354 may be powered off until the temperature sensing criteria are met at block 606. For example, the criteria applied at block 606 may require that an activity count determined from the accelerometer signal is greater than the lower ADL set point or greater than the upper ADL set point such that only the activity metric is used to determine the SIR and adjust pacing rate (blocks 608 and 610) when the SIR is between the LR and the ADL rate. In other examples, the criteria applied at block 606 may require an activity count greater than the LR set point such that an increase in temperature is required to increase the rate response pacing rate from the cardiac pacing LR.

When the temperature sensing criteria are met at block 606, e.g., when the activity count is greater than or equal to a threshold or specified set point, control circuit 306 may enable temperature sensing at an increased sampling rate at block 614. The temperature sensor 354 may be powered on by control circuit 306 by applying power from power source 314 at sampling rate intervals according to the increased sampling rate. In some examples, temperature sensor 354 is powered off with no temperature signal sampling (0 sampling rate) when temperature sensing criteria are not met. In other examples, temperature sensing may be enabled before temperature sensing criteria are met at block 606 but at a relatively low sampling rate, e.g., once per minute, once per ten minutes, every thirty minutes, once per hour, or less often. When temperature sensing is enabled at an increased sampling rate at block 614, the sampling rate may be once per second, once per two seconds, once per ten seconds, once per thirty seconds, once per minute, every two minutes, every five minutes, or other selected frequency for determining temperature changes for rate response control.

In this way, when the temperature sensing criteria are not met at block 606, temperature sensing may be disabled (zero sampling rate) or the temperature signal may be sampled at a relatively low sampling rate to obtain a baseline temperature signal such that power required to operate the temperature sensor and process the temperature sensor signal is conserved when the temperature sensing criteria are not met. It is to be understood that the enabling of an increased sampling rate at block 614 may be the frequency that the temperature sensor is powered on to generate a signal or the frequency that the temperature sensor signal is sampled, e.g., at 1 Hz, 0.5 Hz, etc., and processed by control circuit 306 for determining a temperature change. For example, when a temperature change is determined between a first sample point and a last sample point of temperature change interval, the temperature signal may be sampled once per minute before the temperature sensing criteria are met to obtain a baseline temperature signal. The temperature sensor may be powered on to produce a signal for a sampling rate of 1 Hz to allow the temperature change to be determined at one second intervals after the temperature sensing criteria are met. In other examples, the temperature signal may be sampled at a rate of 1 Hz continuously (before and after temperature sensing criteria are met), but control circuit 306 may process the signal at a higher rate for determining temperature changes more frequently after temperature sensing criteria are met.

When the temperature change is determined by averaging the temperature signal over an averaging time interval in order to obtain the difference between two consecutive average temperatures, the averaging time interval may be shortened and/or the sampling rate increased when temperature sensing criteria are met. Before temperature sensing criteria are met, the averaging intervals may be one minute, five minutes, or 10 minutes long, as examples, with the temperature signal sampled at 30 seconds or another sampling rate during the averaging interval. When temperature sensing criteria are met, the averaging interval may be decreased, e.g., to 10 seconds, and the sampling rate may be increased, e.g., to one second, to allow determination of a temperature change at a higher frequency at block 606. To illustrate, obtaining an average temperature every 20 seconds allows a 0.05 Hz sampling rate of the temperature change when the temperature sensing criteria are unmet. By obtaining an average temperature every second, when temperature sensing criteria are met, the sampling rate of the temperature change is increased to 1 Hz. When temperature sensing is enabled at an increased sampling rate at block 614, the first temperature change may be determined by control circuit 306 as the change from a most recent baseline temperature determined before increasing the temperature change sampling rate or determined from the first two temperature signal values determined after increasing the sampling rate. The various sampling rates and time intervals provided herein are illustrative in nature and not intended to be limiting.

In some examples, when control circuit 306 enables temperature sensing at an increased sampling rate at block 614, control circuit 306 may optionally disable or power off the accelerometer 352. To conserve power when the temperature signal is being used to control rate response, the accelerometer 352 may be powered off or the frequency of determining an activity metric may be decreased, e.g., every ten seconds instead of every two seconds.

After adjusting the pacing rate at block 620 according to the adjusted rate response based on the temperature change determined at block 616, control circuit 306 may determine whether activity sensing criteria are met at block 622. Control circuit 306 may compare the patient activity metric, e.g., an activity count, and/or a target SIR determined based on the activity metrics when the activity metrics are still being determined during temperature sensing. Additionally or alternatively, control circuit 306 may compare the actual pacing rate to a threshold rate. For example, when the actual pacing rate that is adjusted based on temperature sensing is less than the maximum UR, less than a predetermined percentage of the maximum UR, equal to the ADL rate, or equal to the LR rate, activity sensing criteria may be determined to be met by control circuit 306 at block 622.

When the pacing rate, the activity metric and/or the SIR is determined by control circuit 306 to be meet activity sensing criteria at block 622, control circuit 306 may disable sensing and/or processing the temperature signal at the increased sampling rate at block 612. Control circuit 306 may return to using the activity metric for determining the SIR and adjusting the pacing rate (blocks 608 and 610), without using the temperature signal for adjusting the pacing rate. If control circuit 306 previously disabled the accelerometer 352 or reduced the rate of determining the activity metric (at block 614 in response to temperature sensing criteria being met), control circuit 306 may re-enable the accelerometer 352 for producing an acceleration signal by providing power from power source 314 as needed and/or restore the rate of determining the activity metric at block 612.

In some examples, control circuit 306 may disable temperature sensing at block 612 until the temperature sensing criteria are met again at block 606. In other examples, control circuit 306 may reduce a temperature signal sampling rate to enable determination of a baseline temperature signal during periods of time that the temperature sensing criteria are unmet. Temperature sensing may be performed when temperature sensing criteria are unmet, but the sampling rate for determining temperature or a temperature change may be low and increased at block 614 to promote timely rate response to changes in temperature during changing metabolic demand. In still other examples, temperature sensing may be enabled at all times to enable determination of temperature changes at a fixed sampling rate.

In some examples, different criteria may be applied by control circuit 306 for determining whether temperature sensing criteria are met for enabling temperature sensing at an increased sampling rate than the criteria that are applied at block 622 for disabling temperature sensing at the increased sampling rate. To illustrate, when an activity count greater than the lower ADL set point 406 is required to meet temperature sensing criteria at block 606, control circuit 306 may require an activity count less than the upper ADL set point 410 (see FIG. 6) at block 622 to determine that activity sensing criteria are met and temperature sensing at the increased sampling rate can be disabled. The first threshold applied at block 606 for enabling temperature sensing at an increased sampling rate may be higher or lower than the second threshold applied at block 622 to reduce the temperature sensing sampling rate.

More than one threshold may be applied at block 622 by control circuit 306 for controlling temperature signal sensing. For example, with reference to FIG. 6, control circuit 306 may sample the temperature signal at a first sampling rate when the activity count is less than or equal to a first threshold, e.g., less than or equal to the lower ADL set point 406. Control circuit 306 may enable temperature signal sensing at a second sampling rate higher than the first sampling rate when the activity count is greater than the first threshold. Control circuit 306 may disable temperature signal sensing when the activity count is less than the second threshold, which may be a lower threshold than the first threshold.

It is contemplated that one or more activity metric thresholds (or SIR or actual pacing rate) may be set to control the sampling (and/or processing) rate of the temperature signal according to two or more sampling rates, which may include a zero sampling rate. In an example, control circuit 306 may disable temperature signal sensing when the activity count is less than the LR set point 402. In this way, the temperature sensor may be disabled (power withheld) by control circuit 306 and/or processing of the temperature sensor signal may be turned off when the activity count is less than the LR set point. Temperature signal sensing may be enabled at a low sampling rate when the activity count is between the LR set point 402 and an ADL set point (either the lower ADL set point 406 or upper ADL set point 410). The temperature signal sensing may be enabled at a higher sampling rate when the activity count is greater than an ADL set point, e.g., greater than either the lower ADL set point 406 or greater than the upper ADL set point 410.

In some examples, multiple requirements may be applied at block 606 and/or block 622 for enabling/disabling temperature signal sensing or adjusting the sampling rate. For example, at block 606, the activity count may be required to be greater than a first threshold at block 606 and the actual pacing rate may be required to be greater than the ADL rate plus an offset, e.g., plus 5 to 10 pulses per minute. At block 622, the activity count may be required to be less than a second threshold that is lower than the first threshold and the actual pacing rate may be required to be less than or equal to the ADL rate. In some examples, the control circuit 306 of RA pacemaker 14 may be configured to detect atrial tachyarrhythmia based on atrial sensed event signals and/or EGM signal analysis. In response to detecting atrial tachyarrhythmia, control circuit 306 may determine that temperature sensing criteria are met at block 606. It is recognized that a variety of criteria based on the activity metric determined from the accelerometer signal, the SIR, the actual pacing rate, a detected intrinsic heart rate and/or a detected tachyarrhythmia may be defined which correspond generally to an expected increase in the contribution of cardiac motion to the activity metric, which could lead to sustained pacing above the lower rate or even above the ADL, without a corresponding increase in physical activity or even after physical activity has decreased. When increased cardiac motion contribution to the activity metric is expected due to increased pacing rate, temperature sensing at an increased sampling rate is enabled for use in rate response control.

Figure 10:
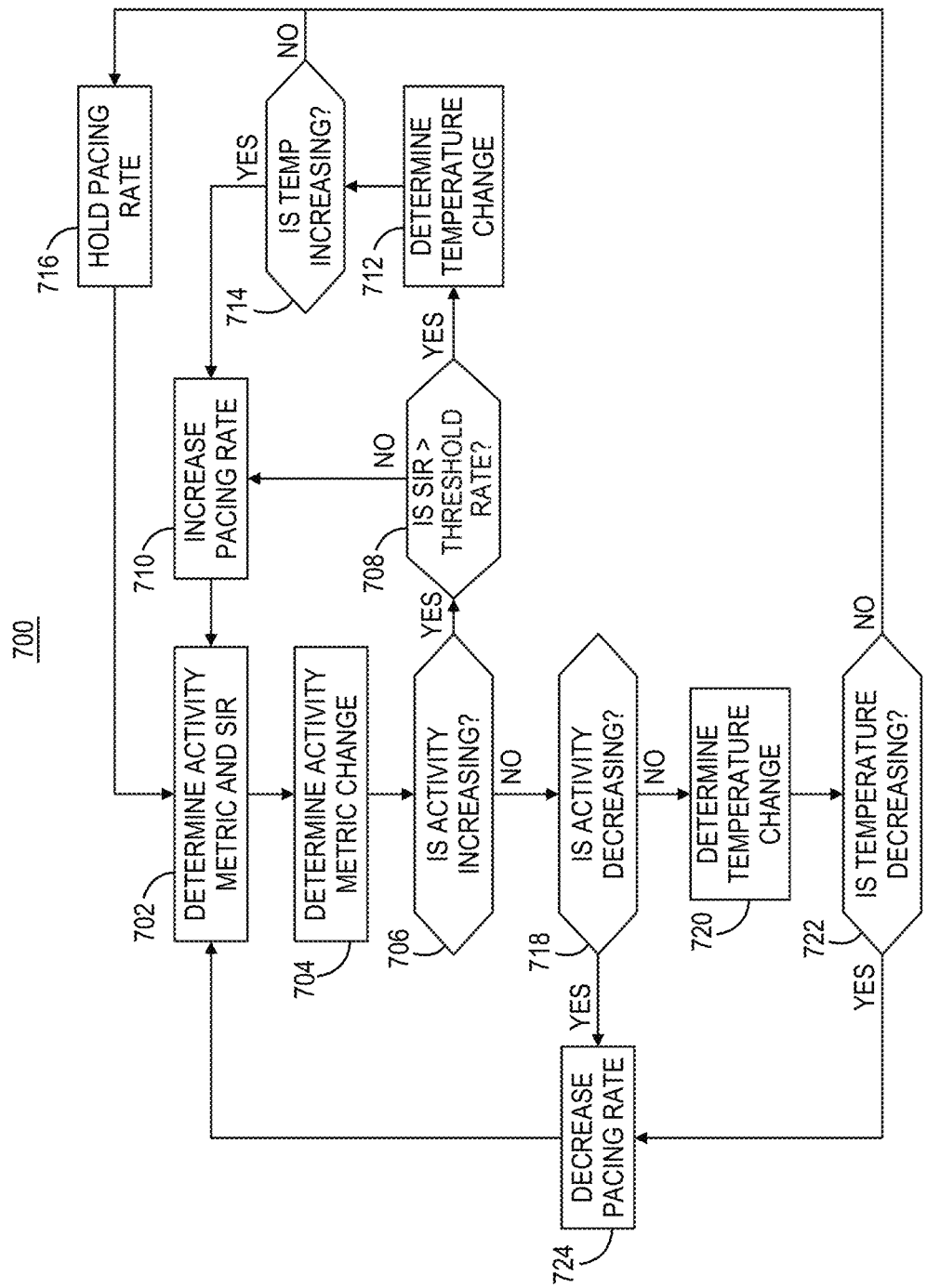
FIG. 10 is a flow chart of a method for controlling rate response pacing by a cardiac pacing device based on both an accelerometer signal and a temperature signal according to yet another example.

FIG. 10 is a flow chart 700 of a method for controlling rate response by a cardiac pacing device based on both an accelerometer signal and a temperature signal according to one example. At block 702, control circuit 306 determines a patient activity metric from the accelerometer signal received from activity sensing circuit 312. Control circuit 306 determines the target SIR based on the determined activity metric at block 702. At block 704, control circuit 306 determines the change in the activity metric since a most recent preceding activity metric in order to determine if the activity metric is increasing, decreasing or staying the same (no change). The activity metric may be determined to have no change when two consecutive activity metrics are equal or within a threshold difference of each other, e.g., when the current activity metric is within a 10% (or other percentage) threshold difference of the preceding activity metric. In other examples, the activity metric may be determined to be increasing if the target SIR increases, decreasing if the target SIR decreases, or have no change when the target SIR based on the activity metric does not change.

If control circuit 306 determines that the activity metric is increasing ("yes" branch of block 706), control circuit 306 may determine whether the SIR is greater than a threshold rate at block 708. In some examples, the threshold rate is the ADL rate at block 708. In other examples, the threshold rate at block 708 may be the programmed lower rate. For example, when pacemaker 12 is implanted in the RV, such that atrial tachyarrhythmia is not expected to be a significant contribution to the acceleration signal, the threshold rate applied at block 708 may be the ADL rate. If the SIR is not greater than the ADL rate, control circuit 306 may increase the pacing rate at block 710 in response to the increasing activity metric without determining a temperature change. The pacing rate may be increased toward the SIR, toward or up to the ADL rate, e.g., according to slope 414 in FIG. 6. Control circuit 306 is configured to increase the pacing rate up to the ADL rate based on the SIR determined from the activity metric without determining a temperature change in some examples.

In other examples, the SIR may be compared to a different threshold than the ADL rate, which may be higher or lower than the ADL rate. For instance, when the pacemaker 12 is implanted in the RA, the onset of atrial tachyarrhythmia while the patient is at rest may cause the SIR to increase. Control circuit 306 may be configured to determine the temperature change at block 712 when the SIR is greater than the lower rate (as determined at block 708) to verify that temperature is increasing at block 714, before increasing the pacing rate from the lower rate.

If the activity metric is increasing at block 706 and the SIR is greater than the threshold rate at block 708, control circuit 306 determines a temperature change at block 712 from the temperature signal received from activity sensing circuit 312. The temperature change may be determined by determining the difference between the current temperature signal amplitude and a previous temperature signal amplitude (which may be an averaged temperature signal amplitude). The current and previous temperature signal amplitudes may be determined one second apart, two seconds apart, five seconds apart or other selected time interval. In some examples, the temperature signal is being sampled at regular intervals so that when the SIR becomes greater than the threshold rate, a baseline temperature acquired when the SIR was less than or equal to the threshold rate can be used by control circuit 306 for determining the first temperature change at block 712.

When the temperature change is increasing (e.g., when the current temperature signal amplitude is at least a change threshold greater than the previous temperature signal amplitude), indicating that the increase in the activity metric is likely due to an increase in metabolic demand, control circuit 306 increases the pacing rate at block 710 toward the SIR according to a maximum rate of change of the pacing rate, e.g., according to slope 416 of FIG. 6. An increasing temperature change may be detected at block 714 by control circuit 306 when the current temperature is at least 0.1 degrees or 0.2 degrees greater than the previous temperature signal, as examples. If the determined temperature change is not an increase in temperature ("no" branch of block 714), then the temperature is decreasing or staying the same (which may include decreases and/or increases that are less than the change threshold range). Control circuit 306 does not increase the pacing rate in response to the increase in the activity metric and SIR. At block 716, the control circuit 306 may hold the pacing rate constant at the current pacing rate.

If the temperature is not changing or is decreasing when the activity metric is increasing, the increased activity metric may be due to increased cardiac motion contributing to the accelerometer signal and not correlated to an actual increase in metabolic demand. Accordingly, in some examples, control circuit 306 may only increase the pacing rate toward an SIR that is greater than the threshold rate if temperature is increasing (a positive temperature change). Control circuit 306 may determine that temperature is not changing (not increasing or decreasing) when the determined temperature change is zero or its absolute value is less than a change threshold.

When control circuit 306 determines that the activity metric is not increasing ("no" branch at block 706), the activity metric (and corresponding SIR) may be decreasing or staying the same (no change). If the activity metric is decreasing (block 718), control circuit 306 decreases the pacing rate at block 724 toward the SIR according to a maximum rate of change for adjusting the actual pacing rate, e.g., according to the transfer function shown in FIG. 6. Accordingly, in some examples, when the activity metric decreases, the pacing rate may be adjusted downward toward the corresponding SIR regardless of what the current pacing rate is (anywhere between the UR and LR) and without checking the temperature signal. A decreasing activity metric is expected to be indicative of a decrease in patient physical activity and metabolic demand, and cardiac motion is not interfering with detection of the decreasing physical activity.

In some instances, control circuit 306 determines that the activity metric is not changing (not increasing or decreasing). When the activity metric is not changing ("no" branch of block 718), control circuit 306 determines the temperature change at block 720. If the temperature is decreasing, control circuit 306 may decrease the pacing rate at block 724, even though the activity metric is not changing. A decreasing temperature is indicative of a likely decrease in physical activity and metabolic demand. The activity metric may be sustained at a current level due to the pacing rate causing cardiac motion contributions to the accelerometer signal rather than sustained patient activity when temperature is decreasing. In other instances, atrial tachyarrhythmia may be contributing to the accelerometer signal, such that the activity metric may not be decreasing as patient activity decreases. Accordingly, in either of these situations, control circuit 306 decreases the pacing rate at block 724 in response to a decrease in temperature when the activity metric and SIR based on the activity metric are not changing. A decreasing temperature change may be detected by control circuit 306 when the current temperature is at least 0.1 or 0.2 degrees or other change threshold less than the previous temperature signal. No change in temperature may be detected when the current temperature is within 0.1 degrees (or within another change threshold) of the preceding temperature, as an example.

Control circuit 306 may decrease the pacing rate at block 724 by a predetermined decrement or according to the rate of change dictated by the SIR transfer function, as shown in FIG. 6, even though the target pacing rate (e.g., the SIR) is not changed. In this case, the rate response is adjusted by control circuit 306 based on temperature sensing, which may include ignoring the current SIR and decreasing the pacing rate away from the current SIR. As the pacing rate is decreased, the cardiac motion contribution to the accelerometer signal may decrease, allowing the activity metric and SIR to follow. If patient physical activity is actually decreasing, the activity metric and SIR are expected to decrease to appropriate levels representative of the patient's metabolic need as control circuit 306 decreases the pacing rate based on the temperature signal, and thereby reduces the cardiac motion contribution to the activity metric, which may be keeping it artificially high. The accelerometer signal eventually becomes reliable again for controlling rate response as the pacing rate is decreased without requiring temperature sensing.

When control circuit 306 determines that the activity metric is not increasing or decreasing ("no" branch of block 718), i.e., staying the same, and temperature is not decreasing ("no" branch of block 722), control circuit 306 may hold the pacing rate at its current value at block 716. If temperature is increasing or the same, and the activity metric is not changing, the pacing rate may be held at its current rate. In some examples, the pacing rate is held at its current rate and not increased until an increase in the activity metric is also detected to verify an increased metabolic demand.

By modifying the rate response by decreasing the pacing rate when temperature is decreasing and the activity metric (or SIR) is staying relatively constant, control circuit 306 avoids a prolonged delivery of a fast pacing rate when cardiac motion is potentially interfering with determination of an accurate patient activity metric. Additionally, by modifying the rate response to prevent increases toward the UR when the SIR is greater than a threshold rate, but temperature is not increasing, control circuit 306 avoids increasing the pacing rate due to increased cardiac motion contributing to the accelerometer signal without a corresponding increase in actual physical activity and metabolic demand.

Figure 11:
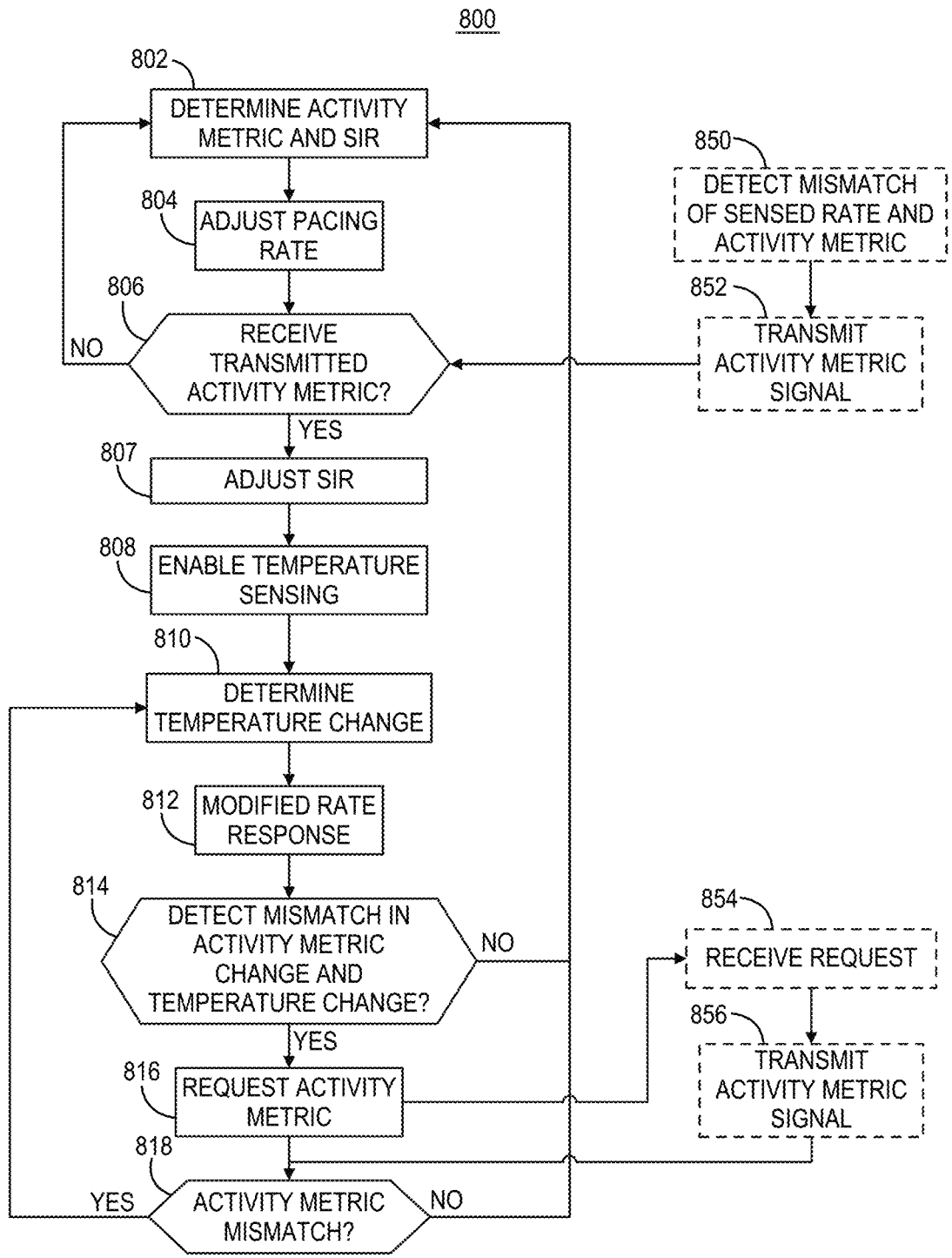
FIG. 11 is a flow chart of a method for controlling rate response pacing by a cardiac pacing device according to another example.

FIG. 11 is a flow chart 800 of a method for controlling rate response pacing by a cardiac pacing device according to another example. In some examples, the functions disclosed herein for monitoring an accelerometer signal and a temperature signal for controlling rate response pacing may be distributed among two or more medical devices. For example, a cardiac monitoring device, ICD, or pacemaker implanted outside the heart may include an accelerometer enclosed by the device housing that is subjected to less cardiac motion than pacemaker 12 or pacemaker 14 implanted in the heart. Pacemaker 12 (or pacemaker 14) implanted within the heart may be configured for communication with another medical device, e.g., ICD 112 as shown in FIG. 3A, implanted away from the patient's heart. Pacemaker 12 may be configured to receive, via telemetry circuit 308, an activity metric signal or a related signal or notification from ICD 112.

ICD 112 may include cardiac electrical signal sensing circuitry for sensing R-waves and an activity sensing circuit including an accelerometer for determining a patient activity metric as generally described herein. For example, a processor of ICD 112 may determine an activity count in the same manner as pacemaker 12. ICD 112 may be configured to transmit an activity metric signal to pacemaker 12 upon request and/or initiate transmission of an activity metric signal, e.g., in response to detecting a mismatch between a sensed ventricular rate and the activity metric (or SIR) determined by ICD 112.

At block 802 of FIG. 11, control circuit 306 of pacemaker 12 determines the activity metric from the accelerometer signal and the corresponding SIR. At block 804, control circuit 306 adjusts the pacing rate toward the SIR as needed, according to an SIR transfer function as described above. At block 806, control circuit 306 may receive a transmitted signal from ICD 112 relating to an activity metric and pacing rate mismatch determined by ICD 112.

In the example of FIG. 11, operations that may be performed by ICD 112 are shown in blocks with dashed lines. The processor of ICD 112 may be configured to compare a sensed ventricular rate determined from R-waves sensed by the ICD cardiac electrical signal sensing circuit to the activity metric (or an SIR based on the activity metric) determined by the ICD processor from its own accelerometer signal. The ICD 112 may be configured to detect a mismatch between the activity metric and the sensed ventricular rate, indicating that the rate response control by pacemaker 12 may not be appropriately tracking the patient physical activity. For example, if the sensed ventricular rate is greater than an SIR determined based on the ICD accelerometer signal, ICD 112 may detect a mismatch of rate and activity metric at block 850. In other examples, the ICD processor may be configured to detect a mismatch in a change in pacing rate and a change in activity metric. For example, if the sensed heart rate (paced by pacemaker 12) is increasing and the activity metric determined from the ICD accelerometer is staying the same or decreasing, ICD 112 may detect a mismatch of rate and activity metric at block 850. In another example, if the heart rate determined by ICD 112 during pacing by pacemaker 112 is staying constant at a high rate, and the activity metric or SIR determined by ICD 112 is decreasing, ICD 112 may detect a mismatch of rate and activity metric.

In response to detecting the mismatch at block 850, ICD 112 may transmit a signal to pacemaker 12 at block 852. ICD 112 may initiate a communication link by transmitting a ping or wake up signal that is detected by pacemaker telemetry circuit 308. Pacemaker telemetry circuit 308 may wake up and listen for the transmitted signal according to a communication protocol implemented in pacemaker 12 and ICD 112. The transmitted signal may be an activity metric and/or a target SIR determined by ICD 112. In other examples, the signal may be a notification that an activity and paced rate mismatch has been detected.

As long as control circuit 306 does not receive a transmitted signal, the rate response pacing control may be deemed appropriate based on the accelerometer signal. When no transmitted signal is received, control circuit 306 continues to determine the activity metric at block 802 and adjust the pacing rate according to the SIR at block 804. The transmitted signal may be an activity metric or SIR determined by ICD 112. When the transmitted signal is received at block 806, control circuit 306 may optionally adjust the SIR at block 807 based on the activity metric or SIR received from ICD 112. In this way, control circuit 306 may make a correction to the pacing rate based on the adjusted SIR. For example, the pacing rate may be decreased toward the adjusted SIR at block 807 to reduce the mismatch detected by ICD 112.

In response to receiving the transmitted signal, control circuit 306 may enable temperature sensing at block 808 if not already enabled. At block 810, control circuit 306 may determine a temperature change and determine a modified rate response based on the temperature change at block 812. As described above in conjunction with FIG. 10, control circuit 306 may adjust or hold the pacing rate based on whether temperature is increasing, decreasing or staying the same and based on whether the activity metric determined from the pacemaker accelerometer signal is increasing, decreasing or staying the same.

When temperature sensing is enabled, control circuit 306 may determine the activity metric change and determine the temperature change to detect a mismatch in the direction of change of the activity metric and temperature. For example, a mismatch may be detected by control circuit 306 when one is increasing and the other decreasing and/or when one is staying the same and the other is either increasing or decreasing. When a mismatch between the temperature trend and the activity metric trend is detected by control circuit 306 at block 814, control circuit 306 may control telemetry circuit 308 to transmit a request to ICD 112 at block 816 to cause ICD 112 to transmit an activity metric signal.

At block 854, ICD 112 receives the request from pacemaker 12 and transmits the activity metric (or corresponding SIR) determined from the ICD accelerometer signal to pacemaker 12 at block 856. Control circuit 306 may compare the received activity metric to the activity metric determined from its own accelerometer signal at block 818. When a mismatch is detected, such that the ICD 112 is detecting a different level of activity than pacemaker 12, control circuit 306 continues to use the temperature signal for controlling the pacing rate by returning to block 810. Control circuit 306 may adjust the pacing rate toward the SIR received from the ICD 112. When control circuit 306 determines that the received activity metric matches the activity metric determined from the pacemaker accelerometer signal, control circuit 306 may return to block 802 to control rate response based on the accelerometer signal. The accelerometer signal may be deemed reliable again for controlling rate response.

While FIG. 11 is described using the example of ICD 112 transmitting an activity metric signal or notification to pacemaker 12 or pacemaker 14, other medical devices, such as pacemaker 212 coupled only to an atrial lead or another cardiac signal sensing device, such as the Reveal LINQ® Insertable Cardiac Monitor available from Medtronic, Minneapolis, Minn., USA, may transmit an activity metric signal or notification to pacemaker 12 to signal that a correction of the rate response is warranted.

In other examples, instead of transmitting an activity metric signal, the second medical device, such as ICD 112 or pacemaker 212, may transmit a temperature change signal to pacemaker 12 when a mismatch in an expected pacing rate and a sensed rate is detected. As described above, ICD 112 or pacemaker 212 may be coupled to a lead carrying a temperature sensor for sensing a signal correlated to core body temperature. Pacemaker 12 or pacemaker 14 may not include a temperature sensor due to space or power constraints. Temperature change signals may be transmitted to pacemaker 12 or pacemaker 14 from another medical device until the sensed heart rate or an activity metric or SIR determined by ICD 112 or pacemaker 212 is determined to be less than a threshold, e.g., less than an ADL set point or corresponding rate. Accordingly, in the techniques described above in conjunction with the flow charts of FIGS. 8-10, control circuit 306 may receive the temperature signal (or determined temperature change) from another device implanted in the patient, e.g., via telemetry circuit 314.

Figure 12:
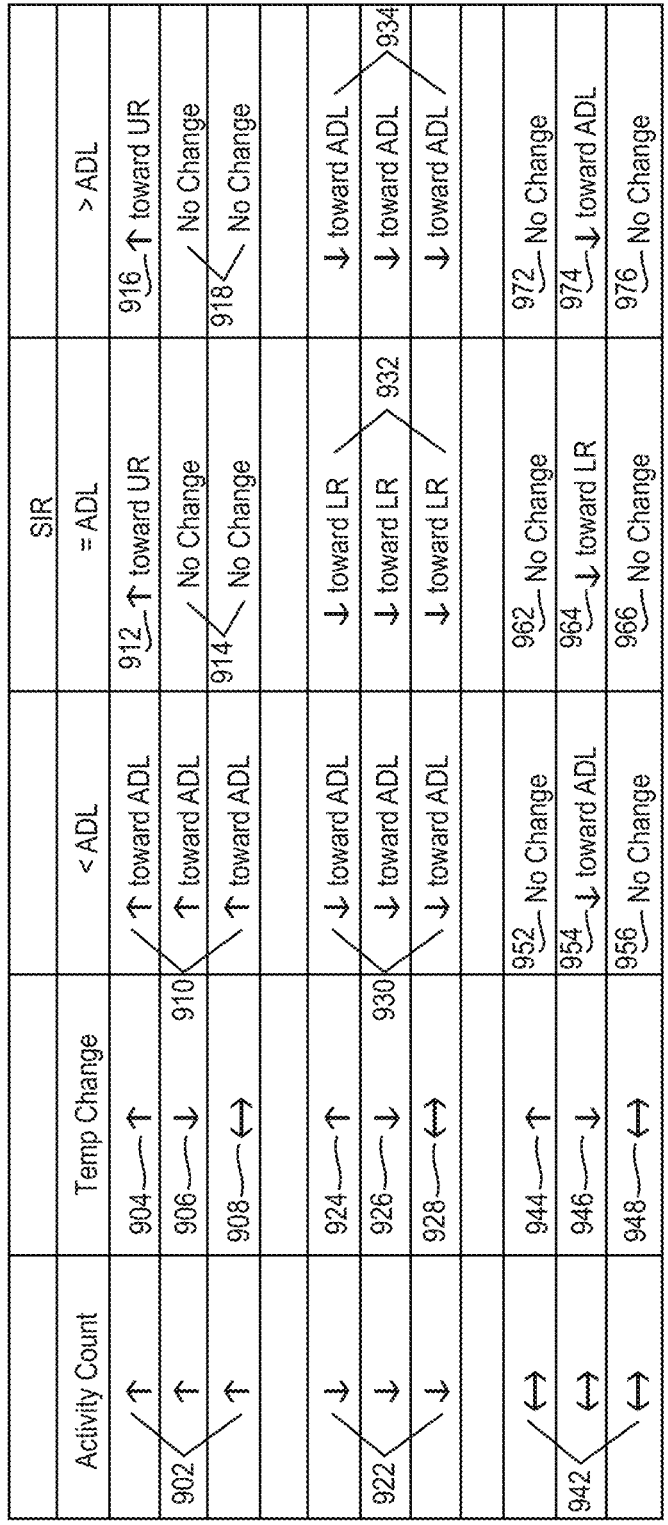
FIG. 12 is a diagram of the rate response pacing rate adjustments that may be made based on whether activity count is increasing, decreasing or not changing and whether temperature is increasing, decreasing or not changing.

FIG. 12 is a diagram 900 of adjustments to controlling the rate response pacing rate that may be made by control circuit 306 based on whether activity count is increasing, decreasing or not changing and/or whether temperature is increasing, decreasing or not changing. Each combination of the direction of change in activity count and temperature is listed in diagram 900 with a corresponding adjusted rate response instruction executed by control circuit 306 by adjusting (or holding constant) the SIR. The adjusted rate response instruction may also depend on the current value of the SIR. For example, the rate response adjustment may depend on whether the SIR is less than the ADL rate, equal to the ADL rate or greater than the ADL rate, as shown in this example. In other examples, the threshold rate applied to the SIR may be different than the ADL rate as shown in FIG. 12. For example, pacemaker 14 implanted in the RA may adjust the rate response based on combinations of activity count change and temperature change when the SIR is greater than the programmed lower rate to account for atrial tachyarrhythmia causing an SIR greater than the lower rate when the patient is at rest.

Diagram 900 may represent a look up table (LUT) of instructions stored in memory 310 and retrieved by control circuit 306. Control circuit 306 may determine a rate response adjustment instruction by looking up the SIR adjustment in the LUT represented by diagram 900. Control circuit 306 may determine the direction of an activity count change (increase, decrease, or no change), determine the direction of a temperature change (increase, decrease, or no change), and compare the current SIR to one or more threshold rates to select a rate response adjustment from the LUT represented by diagram 900. The LUT may store instructions for either increasing, decreasing or holding the current SIR constant based on the combination of activity count change and temperature change. When the rate response adjustment is an increase or a decrease in the SIR, the rate response pacing rate may be adjusted toward the SIR according to a maximum rate of change and as defined by a slope of the SIR transfer function as described above in conjunction with FIG. 6.

In the first three rows of the LUT, SIR adjustment instructions may be stored for when control circuit 306 detects an increasing activity count 902, depending on what the change (if any) in temperature is and what the current SIR is. For the sake of illustration, FIG. 12 is described with reference to a threshold rate applied to the SIR being the ADL rate, though it is to be understood that other threshold rates may be used. When control circuit 306 determines an increase in activity count 902, and the SIR is less than the ADL rate 910, the SIR is increased from the current SIR toward the ADL rate, e.g., according to slope 414 shown in FIG. 6, regardless of whether temperature is increasing 904, decreasing 906 or not changing 908. Increasing activity counts at the low pacing rate (less than ADL) can be expected to be insignificantly affected by cardiac motion and therefore indicative of a true increase in patient physical activity, warranting an increase in the SIR toward the ADL rate.

If the SIR is equal to or greater than the ADL rate, the SIR is not changed (914 and 918) when the temperature is decreasing 906 or not changing 908, even though activity counts are increasing 902. If temperature is not increasing to confirm a true increase in physical activity when activity count is increasing, the rate response is adjusted by holding the SIR at the current rate instead of increasing the SIR toward the UR when the activity count increases. When both an increased activity count 902 and increased temperature 906 are detected (first line of the LUT), as corroborating evidence of an increase in physical activity, and the SIR is equal to or greater than the ADL rate, the rate response pacing rate may be increased toward the maximum UR (912 and 916).

The next three rows of the LUT represented by diagram 900 may store instructions for adjusting the rate response, by adjusting the SIR, when control circuit 306 detects a decrease in activity count 922. When activity counts are decreasing, physical activity is likely decreasing and this decrease in physical activity is being detected based on activity counts without confounding effects of cardiac motion in the accelerometer signal. As such, in all conditions of temperature change (increasing temperature 924, decreasing temperature 926, or no change in temperature 928) and regardless of current SIR (less than, equal to, or greater than the ADL rate), a decreasing activity count is relied on by control circuit 306 in controlling the rate response. As such, control circuit 306 decreases the SIR toward the LR 930 and 932 when the SIR is less than or equal to the ADL rate, respectively. When the SIR is greater than the ADL rate, control circuit 306 decreases the SIR toward the ADL rate 934.

The next three rows of the LUT represented by diagram 900 may include instructions for adjusting the rate response by adjusting the SIR when activity count is not changing 942. When activity count is not changing and temperature is increasing 944, other factors (such as fever) may be causing the rise in body temperature or the level of physical activity may be constant with increasing core body temperature lagging increased activity counts, e.g., as shown in the graph of FIG. 7. Accordingly, control circuit 306 may hold the SIR at its current value (no change 952, 962, 972) regardless of the current value of the SIR. An increase in temperature and no change in the activity count may not be sufficient evidence to increase or decrease the SIR.

When temperature is decreasing 946, however, the unchanging activity count may be due to cardiac motion contributing to the accelerometer signal. Decreasing temperature may be evidence of decreasing or cessation of physical activity. As such, control circuit 306 adjusts the rate response based on the temperature signal by decreasing the SIR. The SIR is decreased toward the LR 954 and 964 when the current SIR is less than or equal to the ADL rate and decreased toward the ADL rate 974 when the SIR is greater than the ADL rate. When neither activity count nor temperature is changing (942 and 948), control circuit 306 holds the SIR at its current value 956, 966 and 976, regardless of the current SIR rate.

The LUT represented by diagram 900 is shown including instructions for adjusting the rate response by adjusting the SIR based on both activity and temperature signals. In other examples, a LUT storing instructions executed by control circuit 306 for adjusting rate response based on positive, negative or no changes in activity counts and/or temperature may include other adjustments to the rate response control parameters, such as adjustments to the ADL and/or UR set points and/or the slopes of the rate response transfer function, e.g., slopes 414 and 416 shown in FIG. 6. For instance, as described above, an ADL and/or UR set point may be increased when temperature is decreasing and the activity count is not changing and the SIR is greater than the ADL rate. This adjustment has the effect of decreasing the rate response pacing rate in response to decreasing temperature when cardiac motion may be contributing to the activity counts. Increasing the slope 416 between the UR 418 and the ADL rate 408 when the SIR is greater than the ADL rate and temperature is decreasing may allow the rate response pacing rate to be decreased more quickly toward the ADL rate when the activity count is not changing. In this way, the reduction in patient physical activity based on decreasing temperature allows control circuit 306 to reduce the pacing rate, which in turn may reduce the contribution of cardiac motion to the accelerometer signal, restoring the reliability of the activity counts in detecting a true decrease in patient physical activity.

When atrial tachyarrhythmia is the source of increased cardiac motion contributing to the accelerometer signal, termination of the atrial tachyarrhythmia may result in a sudden decrease in the SIR if patient activity is low or has decreased since the onset of the atrial tachyarrhythmia. In this situation, when activity count is decreasing 922, control circuit 306 may adjust the pacing rate toward the SIR regardless of temperature change. When the activity count is increasing 902 or not changing 942 and the SIR is greater than a threshold rate, e.g., greater than the lower rate, control circuit 306 may rely on the temperature change to determine whether to increase, decrease or hold the current pacing rate.

Figure 13:
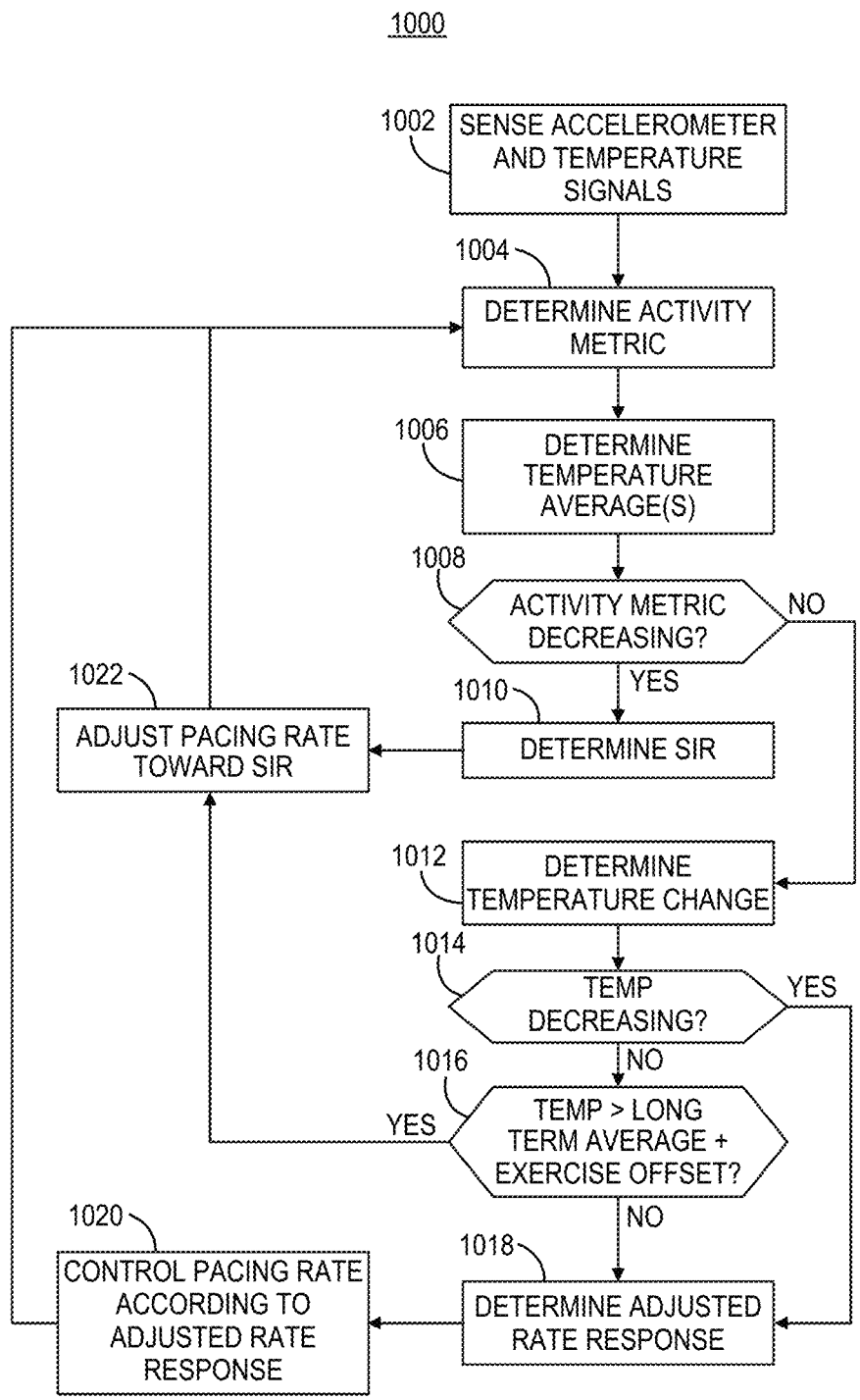
FIG. 13 is a flow chart of a method for controlling rate response pacing based on an accelerometer signal and temperature signal according to another example.

FIG. 13 is a flow chart 1000 of a method for controlling rate response pacing based on an accelerometer signal and temperature signal according to another example. At block 1002, the activity sensing circuit 312 may sense both the accelerometer signal and the temperature signal to pass a filtered and rectified acceleration signal and the temperature signal to control circuit 306. At block 1004, control circuit 306 may determine the activity metric from the accelerometer signal, which may be determined as an activity count as described above.

At block 1006, control circuit 306 may determine a long term average of the temperature signal. The temperature signal may be sampled at a selected sampling interval, e.g., once per second, once per ten seconds, once per thirty seconds, once per minute, once every two minutes, once every ten minutes or other sampling rate. The sampled temperatures may be averaged over one hour, two hours, four hours, eight hours, twelve hours, twenty-four hours or other selected long term averaging time interval. In some examples, the long term average is a moving average, e.g., determined over the most recent twenty-four hours. In other examples, the long term average may be a daily average determined by averaging all sampled temperatures over a given day.

Figure 14:
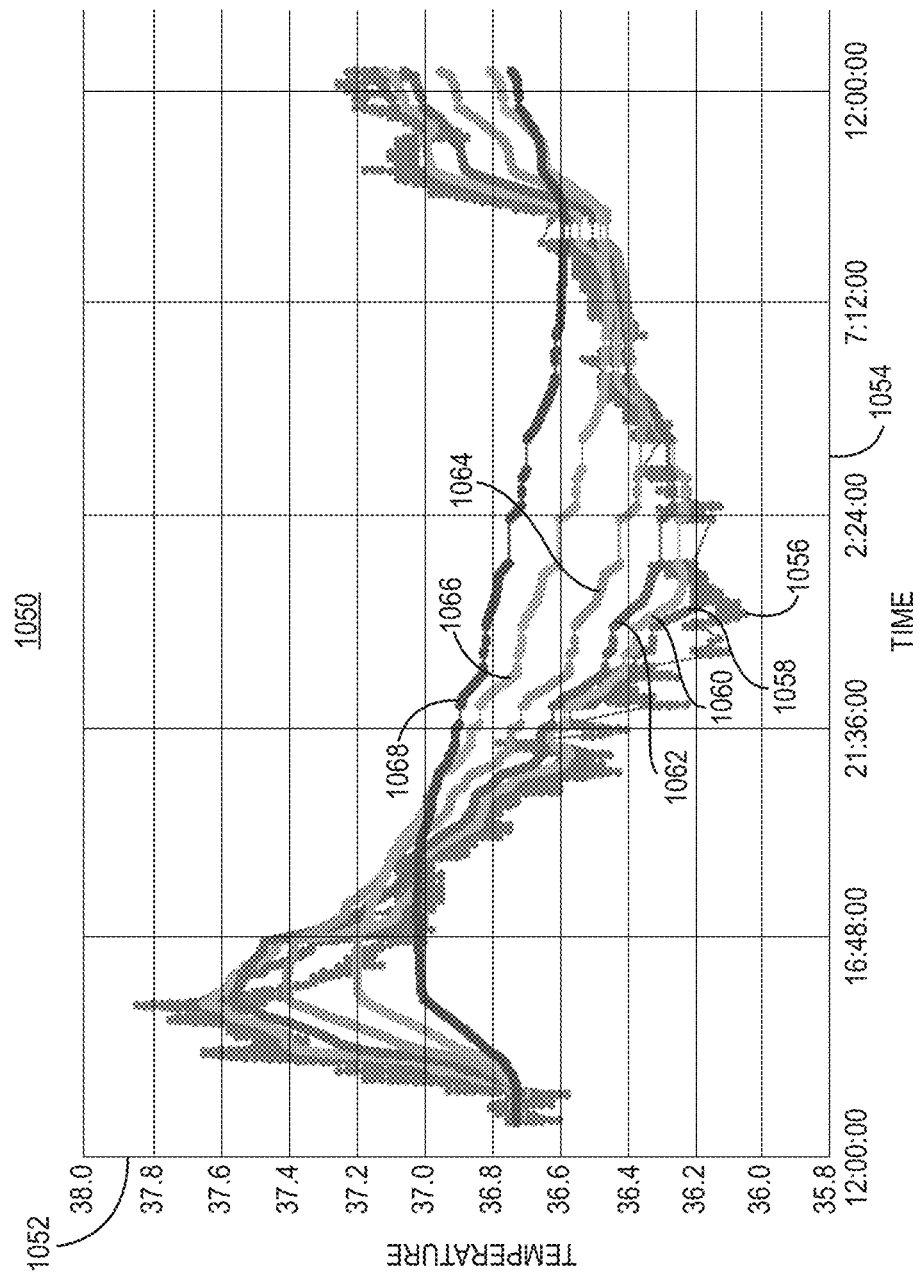
FIG. 14 is a plot of different moving averages of temperature that may be determined over different averaging intervals by a medical device.

FIG. 14 is a plot 1050 of different moving averages of temperature determined over different averaging intervals. In this example, control circuit 306 samples the temperature signal every two seconds over a 24-hour period. The sampled temperature signal is plotted as curve 1056, with time on the x-axis 1054 and temperature on the y-axis 1052. Different sampling rates may be used than the 2-second sampling rate represented here. For instance lower sampling rates, such as once per minute or less often may be used since temperature is not expected to change rapidly, particularly when the patient is not physically active. The moving averages determined over different averaging intervals of 7.5 minutes (1058), 15 minutes (1060), 30 minutes (1062), one hour (1064), two hours (1066) and four hours (1068) are also plotted. As described below, the short term moving averages (e.g., averaging interval of ten minutes or less) and/or long term moving averages (e.g., more than ten minutes) may be determined and used by control circuit 306 in determining when and how to adjust the rate response based on temperature.

Referring again to FIG. 13, at block 1006, control circuit 306 may determine one or more moving averages of the temperature signal over one or more respective averaging intervals. The moving averages determined at block 1006 may depend on the current activity level. For example, when activity counts are low at rest or less than an ADL set point, control circuit 306 may determine a long term moving average of temperature. When activity counts are higher, e.g., equal to or greater than the ADL set point, a short term moving average may additionally or alternatively be determined at block 1006. The moving averages determined at block 1006 may be buffered in memory 310. In some examples, a first-in-first-out memory buffer may be configured to store at least one long term moving average and two or more short term moving averages.

At block 1008, control circuit 306 may determine if the activity metric is decreasing. The activity metric may be determined to be decreasing when the activity count is at least one count less than the preceding activity count. In other examples, the activity metric may be determined to be decreasing when a threshold number, e.g., three or more, of consecutive activity counts represent consecutive decreases in activity count. When the activity metric is decreasing, control circuit 306 may determine the SIR based on the activity count at block 1010 and adjust the rate response pacing rate toward the SIR at block 1022. A decreasing activity count is expected to be reliable for controlling rate response without a significant confounding influence of cardiac motion.

When control circuit 306 determines that the activity count is not decreasing (increasing or not changing) at block 1008, control circuit 306 may determine the temperature change at block 1012. In some examples, as described above, control circuit 306 may first verify whether the current activity count or associated SIR are greater than a threshold level, for example at least an ADL set point or the ADL rate, respectively, before determining the temperature change. In some examples, as long as the activity metric (and associated SIR) corresponding to rest or patient activity is at or below ADL, the activity counts continue to be used for setting the SIR and controlling rate response without using temperature. In other examples, control circuit 306 may determine the temperature change when the activity metric (or SIR) is not decreasing ("no" branch of block 1008), regardless of the current level of the activity metric (or associated SIR).

At block 1012, control circuit 306 determines if the temperature change is increasing, decreasing or not changing. Any of the techniques described above may be used to determine a trend in the temperature change. In some examples, a short term moving average, e.g., a moving average determined over two minutes, five minutes or other averaging interval such as 10 minutes or less may be determined and compared to the preceding short term moving average. In some examples, these short term moving averages may be determined at block 1006 and stored in a buffer in memory 310. In other examples, control circuit 306 conserves processing power and determines the short term moving averages at block 1012 in response to a non-decreasing trend in the activity metric (or associated SIR).

The temperature change may be determined by subtracting a current temperature (which may be a single sample point, average temperature over a predetermined time interval, or a short term moving average temperature) from a preceding temperature occurring at a temperature monitoring time interval earlier than the current temperature. The temperature monitoring time interval for determining a temperature change may be one minute, two minutes, or five minutes as examples. When one or more consecutively determined temperature differences are positive, temperature is determined to be increasing. When one or more consecutive temperature differences are negative, temperature is determined to be decreasing. When one or more consecutive temperature differences are zero and/or include both positive and negative difference, temperature may be determined to be non-changing by control circuit 306.

When temperature is decreasing ("yes" branch of block 1014), control circuit 306 determines an adjusted rate response at block 1018. As described above in conjunction with FIG. 12, control circuit 306 may retrieve an instruction from a LUT for decreasing or holding constant the SIR based on the decreasing temperature, which may depend on what the current SIR and/or activity metric trend is. For example, if the activity count is not changing and the SIR is greater than the ADL rate, the SIR may be decreased at block 1018. When temperature is decreasing and the SIR is greater than the equal to or greater than the ADL rate, the SIR may be held constant when the activity metric is increasing.

If temperature is not decreasing as determined by control circuit 306 at block 1014, control circuit 306 may compare the current temperature (which may be single sample point, average of multiple sample points or short term moving average) to a long term average temperature at block 1016. The long term average temperature may be determined at block 1004 as described above and stored in memory 310. The long term average may be a daily average, in some examples, and may be determined over the preceding day or may be a moving 24-hour (or other selected long time interval) average.

When the current temperature is greater than the long term average, "yes" branch of block 106, the higher than average temperature supports a determination that the patient is active and requires pacing rate support. The comparison at block 1016 may be a comparison of the current temperature to the long term average plus an exercise offset, e.g., 0, 0.5, 1.0, 1.25 or 1.5 degrees as examples. The exercise offset may represent a minimum rise in body temperature expected when the patient is physically active. The long term average plus the exercise offset, therefore, represents a minimum patient-specific body temperature expected during physical activity that requires rate response pacing support.

In some instances, if the activity metric is sustained at a high level, e.g., at or greater than the ADL rate, the patient may or may not still be physically active since an increased rate response pacing rate may be causing cardiac motion to contribute to the activity metric. A determined temperature change may not meet criteria for determining a decreasing temperature when the temperature has decreased very gradually or has already reached a baseline temperature (less than the long term average plus the exercise offset). In order to avoid a sustained, increased pacing rate under these conditions, control circuit 306 may verify that the current temperature is greater than the long term average (plus any specified exercise offset) as evidence that the patient is indeed still physically active.

When both activity counts and temperature are not changing, and the current temperature is greater than the long term average plus any exercise offset, the patient may be engaged in sustained activity. Control circuit 306 may adjust the pacing rate toward the SIR based on the activity metric at block 1022 in response to the non-changing temperature that is greater than the long term average plus any offset, in order to continue providing ventricular pacing rate support during sustained exercise. No adjustment is made to the rate response (e.g., by not adjusting the SIR) at block 1018.

However, when the current temperature is less than or equal to the long term average, "no" branch of block 1016, the core body temperature may have gradually returned to a baseline indicating sustained high rate pacing is no longer needed. In this case, control circuit 306 may determine the adjusted rate response at block 1018. In response to the current temperature being less than the long term average plus any specified exercise offset, control circuit 306 may adjust the rate response at block 1018 by decreasing the SIR toward the next lower set point. At block 1020, control circuit 306 adjusts the rate response pacing rate based on the adjusted SIR. In this way, control circuit 306 may avoid the situation of a sustained high pacing rate when the activity metric is not changing due to heart motion contributions and temperature is not changing because activity has already decreased to a relatively lower level (or ceased).

Referring to FIG. 12 as an example, when the activity count is not changing 942, and temperature is not changing 948, and the current SIR is greater than the ADL rate, the SIR may be held constant 976 based on the instruction stored in the LUT. In these conditions, the situation may exist that physical activity has stopped or decreased and temperature is no longer decreasing, but activity counts are not changing because of heart motion at the higher pacing rate. To avoid having the rate response pacing rate being stuck at an SIR that is not being adjusted under the instruction 976, control circuit 306 may apply the additional criterion at block 1016 of requiring the current temperature, which may be a single sample point or a short term average, be greater than the long term average in order to maintain the SIR at its current value according to the instruction 976. Otherwise, when the current temperature is not greater than the long term average plus any exercise offset at block 1016, control circuit 306 decreases the SIR at block 1018. The rate response pacing rate is adjusted toward the lower SIR at block 1020.

Figure 15:
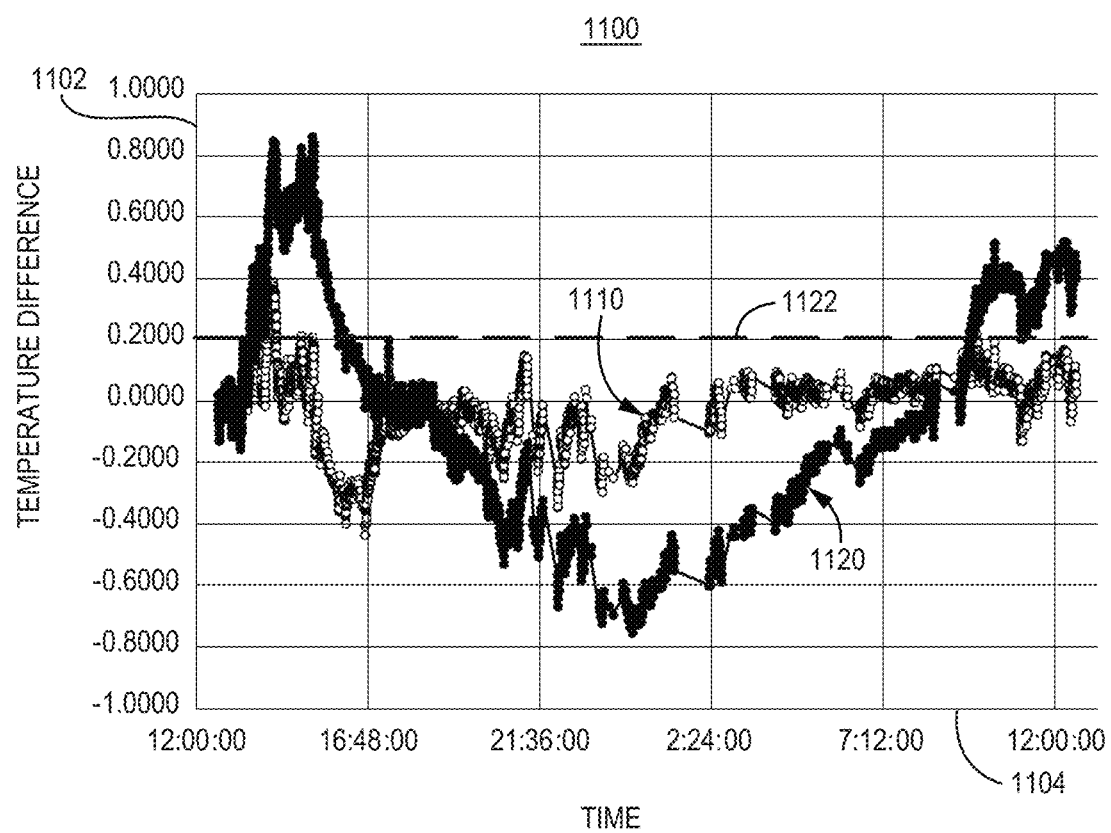
FIG. 15 is a graph of temperature differences that may be determined by a medical device for use in controlling rate response pacing.

FIG. 15 is a graph 1100 of temperature differences that may be determined by control circuit 306 for use in controlling rate response pacing. Temperature differences are plotted along the y-axis 1102 and time is plotted along the x-axis 1104. The plotted curve 1110 represents the current temperature minus a short term moving average of temperature. In this example, temperature is sampled from the temperature signal every two seconds. The short term moving average is the average of all temperature signal sample points over a moving fifteen minute averaging time interval (the most recent 450 temperature signal sample points in this example). The plotted curve 1110 represents the difference between the current temperature sample point and the short term moving average. In some examples, control circuit 306 may detect a temperature change as an increase, decrease or no change by subtracting the current temperature from the short term moving average. When the difference is positive, the temperature change is an increase. When the difference is negative, temperature is decreasing. In other examples, two short term moving averages may be determined over different averaging intervals. For example, a one minute average may be determined as the current temperature and the fifteen minute average may be subtracted from current temperature to determine a temperature change as an increase, decrease or no change. Control circuit 306 may determine the temperature change based on short term moving averages and use the determined temperature change to adjust the rate response as described above, e.g., in conjunction with FIG. 12.

The second plotted curve 1120 represents the difference between the current temperature and a long term moving average. The long term moving average is determined by averaging the two-second temperature signal sample points over four hours, 7200 sample points, in this example, but may be averaged over longer time intervals, e.g., up to twenty four hours or more. As described in conjunction with FIG. 13, control circuit 306 may verify that the difference between a current temperature signal sample point (or a short term moving average) and a long term moving average temperature is positive or greater than a positive exercise offset threshold 1122, indicating that current body temperature is greater than a patient-specific average body temperature. This verification may be used to maintain a current SIR at the same rate without rate response adjustment when both activity counts and temperature are not changing. However, when the difference between the current temperature and the long term average temperature (curve 1120) is negative or less than an exercise offset threshold 1122, the patient's current body temperature may have fallen to a body temperature that is closer to the long term average due to decreased or ceased activity. In this case, control circuit 306 may adjust the rate response by decreasing the SIR even though temperature and activity counts are not changing.

In the example shown, the exercise offset threshold 1122 is shown as 0.2 degrees C. As such, if the current body temperature is not at least 0.2 degrees C. higher than the long term average temperature, control circuit 306 may decrease the SIR when both activity counts and temperature are not changing. The exercise offset threshold 1122 may be 0.1 to 1.0 degrees C., as examples.

Figure 16:
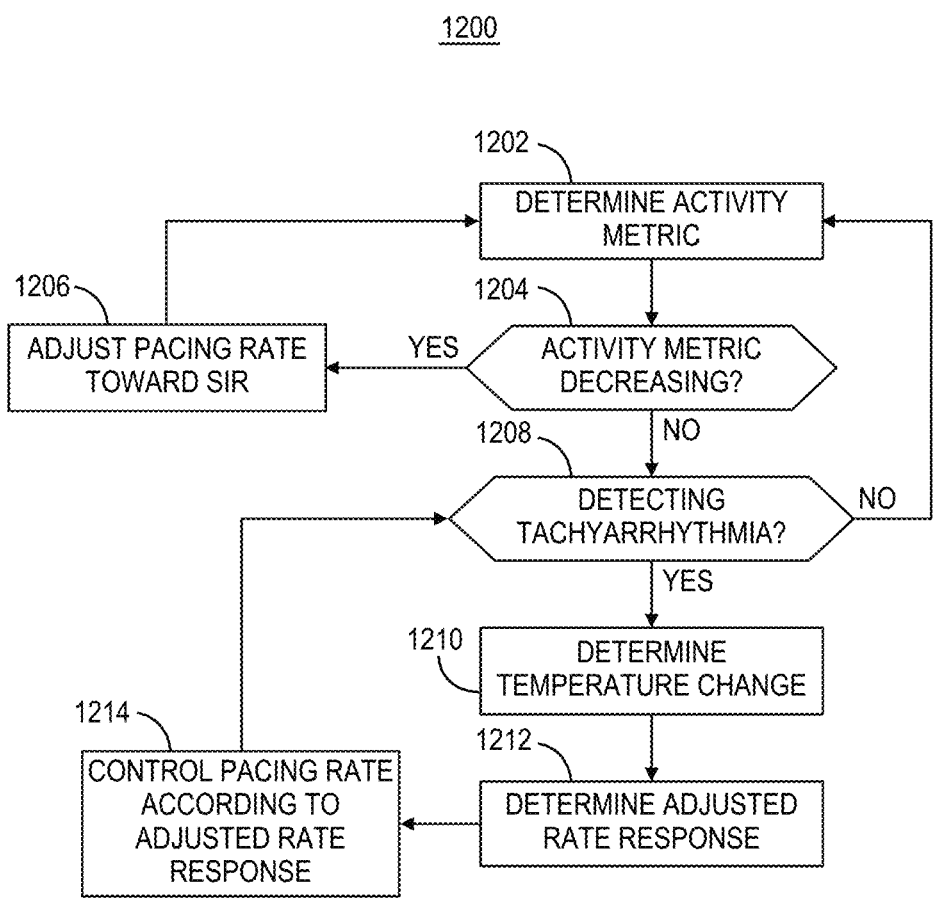
FIG. 16 is a flow chart of a method for controlling rate response according to dual sensors according to another example.

FIG. 16 is a flow chart 1200 of a method for controlling rate response according to dual sensors according to another example. At block 1202, control circuit 306 determines the activity metric, e.g., an activity count, from the acceleration signal received from activity sensing circuit 312. At block 1204, control circuit 306 determines if the activity metric is increasing, decreasing or not changing compared to a previously determined activity metric. For example, the most recent preceding activity count may be compared to a currently determined activity count at block 1204. If the activity metric is decreasing, control circuit 306 may adjust the pacing rate toward the SIR based on the activity metric at block 1206. When the activity metric is decreasing, cardiac contributions to the acceleration signal are presumed to be non-confounding signals in the determination of the SIR.

When the activity metric is not decreasing ("no" branch of block 1204), control circuit 306 may determine if tachyarrhythmia is being detected at block 1208. For example, control circuit 306 may detect atrial tachyarrhythmia, e.g., based on an analysis of atrial event signals received from sensing circuit 304, which may include an analysis of atrial event intervals and/or morphology, and/or an analysis of the acceleration signal. Any tachyarrhythmia detection technique may be used at block 1208 for detecting a tachyarrhythmia. A variety of tachyarrhythmia detection methods may be used in conjunction with the techniques disclosed herein for causing control circuit 306 to change to using the temperature signal for rate response pacing control during a tachyarrhythmia. If tachyarrhythmia is not being detected at block 1208, control circuit 306 returns to block 1202 and continues to control the rate response based on the accelerometer signal.

When tachyarrhythmia is being detected at block 1208, control circuit 306 determines a temperature change from the temperature signal at block 1210 in response to a non-decreasing activity metric and tachyarrhythmia detection.

Control circuit 306 determines an adjusted rate response at block 1212 based on the determined temperature change and controls the pacing rate according to the adjusted rate response at block 1214. As described above, if temperature is decreasing, the pacing rate may be decreased from the current pacing rate according to a maximum rate of deceleration. If the temperature is not changing, the pacing rate may be held at the current pacing rate. If temperature is increasing, the pacing rate may be increased toward the SIR determined based on the accelerometer signal.

In some examples, the adjusted rate response is an increased set point when the temperature is not increasing and a tachyarrhythmia is being detected. For example, the LR set point or the lower ADL set point may be increased at block 1212. By increasing a set point, the pacing rate may be held at the current pacing rate. To illustrate, the LR set point may be increased at block 1212. The pacing rate may be held at the lower rate at block 1214 based on the activity count being less than or equal to the increased LR set point. The LR set point may be increased to the current activity count value in response to a detected tachyarrhythmia and non-increasing temperature change. In other examples, the LR set point may be increased to a value greater than the current activity count or to a predetermined increased value, e.g., up to the lower ADL set point. In addition to or instead of adjusting a set point, control circuit 306 may adjust the slope of the transfer function of FIG. 6. For example, the slope 414 between the LR set point 402 and the lower ADL rate 406 may be decreased by control circuit 306 to slow the rate response to increasing activity count that may be due to the tachyarrhythmia. Temperature increase typically lags exercise onset. By adjusting the slope 414, the pacing rate may be increased more slowing during detected tachyarrhythmia until an increase in patient physical activity is confirmed based on an increase in temperature and continued increase in the activity metric.

Although a temporary rate response pacing rate is determined at block 1214, control circuit 306 will likely inhibit pulse generator 302 from generating pacing pulses because sensing circuit 304 is likely to be sensing P-waves and passing P-wave sensed event signals to control circuit 306 at the fast intrinsic atrial rate during the atrial tachyarrhythmia. If undersensing of atrial depolarization signals occurs during the atrial tachyarrhythmia, pacing pulses generated by pulse generator 302 according to the adjusted rate response at block 1214 may or may not capture the atrium during the detected tachyarrhythmia. In some instances, P-waves or fibrillation waves may be undersensed resulting in pacing pulses generated according to the adjusted rate response. However, the adjusted rate response that holds the pacing rate at the lower rate when temperature is not increased acts to conserve power source 314 since the pacing pulses are not delivered at an increased rate based on the activity metric. When P-wave or fibrillation waves are sensed at a rate greater than the lower rate, pulse generator 302 withholds the pacing pulses. If sustained undersensing of low amplitude P-waves or fibrillation waves occurs during the detected tachyarrhythmia, pacing pulses may be generated at the lower rate. Pacing pulses generated by pulse generator 302 during the atrial tachyarrhythmia due to undersensing are not expected to have any adverse effects and will conserve power source 314 compared to pacing at the SIR that is elevated due to the atrial tachyarrhythmia.

After adjusting the pacing rate as needed according to the adjusted rate response at block 1214, control circuit 306 may determine if the tachyarrhythmia is still being detected. If not, control circuit 306 may restore the programmed value of any adjusted set points and/or slopes of the target rate transfer function (if adjusted) and return to block 1212 to determine the activity metric and control the rate response based on the accelerometer signal. If control circuit 306 is still detecting tachyarrhythmia at block 1208, control circuit 306 may continue adjusting the pacing rate based on the temperature change determined at block 1210. Adjustments to the pacing rate may be based on the temperature change alone or based on a combination of the determined activity metric change and the determined temperature change, e.g., by determining a rate adjustment from a LUT stored in memory 310. By setting the rate response pacing rate based on temperature alone or a combination of temperature and the activity counts during atrial tachyarrhythmia, pacing pulses generated at an appropriate rate response pacing rate may be delivered according to physiological, metabolic need when the atrial tachyarrhythmia terminates (such that the pacing pulses are no longer inhibited due to the intrinsic fast atrial rate).

It is to be understood that operations represented in FIG. 16 may be combined with any of the methods described above for controlling the rate response pacing rate. For example, the process of FIG. 16 may be used when the activity metric is less than a threshold, e.g., less than or equal to an ADL set point. When the activity metric is greater than the threshold, temperature sensing criteria may be met even if tachyarrhythmia is not being detected, e.g., as described in conjunction with FIG. 8. As such, control circuit 306 may control rate response pacing based only on the accelerometer signal when the activity metric is less than the ADL set point (or another threshold) and tachyarrhythmia is not being detected. When the activity metric is less than the ADL set point (or another threshold) and tachyarrhythmia is being detected, control circuit 306 may rely on the temperature signal alone or a combination of the temperature signal and the accelerometer signal for controlling the rate response. When the activity metric is greater than the ADL set point, whether or not tachyarrhythmia is being detected, control circuit 306 may use only the temperature signal or a combination of both the temperature signal and the accelerometer signal for controlling the rate response using the techniques described above.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device comprising:
   an accelerometer configured to generate an acceleration signal;
   a temperature sensor configured to generate a temperature signal;
   a therapy delivery circuit configured to deliver cardiac pacing pulses at a pacing rate;
   a memory configured to store a transfer function that relates an activity metric to a target cardiac pacing rate, the transfer function being defined by at least one slope and at least one set point; and
   a control circuit configured to:
      receive the acceleration signal and the temperature signal;
      determine a first activity metric representative of patient physical activity from the acceleration signal;
      determine from the acceleration signal a second activity metric representative of patient physical activity at a time later than the first activity metric;
      determine the target cardiac pacing rate based on the second activity metric according to the transfer function;
      determine that the second activity metric is equal to or greater than the first activity metric;
      determine a temperature change from the temperature signal; and
      in response to the second activity metric being equal to or greater than the first activity metric, determine an adjusted target cardiac pacing rate by:
         adjusting the transfer function by adjusting at least one of the at least one slope or the least one set point based on the temperature change; and
         determining the adjusted target cardiac pacing rate based on the second activity metric according to the adjusted transfer function; and
      adjust the pacing rate according to the adjusted target cardiac pacing rate.

2. The medical device of claim 1, wherein the control circuit is further configured to:
   determine that at least one of:
      the second activity metric is greater than or equal to an activity threshold; or
      the target cardiac pacing rate based on the second activity metric is greater than or equal to a rate threshold; and
   determine the temperature change in response to the at least one of the second activity metric being greater than or equal to the activity threshold or the target cardiac pacing rate based on the second activity metric being greater than or equal to the rate threshold.

3. The medical device of claim 1, wherein the control circuit is further configured to:
   determine that the temperature change is less than a threshold change; and
   withhold adjusting the transfer function in response to the temperature change being less than the threshold change when the second activity metric is greater than or equal to the first activity metric.

4. The medical device of claim 1, wherein the control circuit is further configured to:
- determine a moving average of the temperature signal;
- determine a current temperature from the temperature signal;
- determine a difference between the current temperature and the moving average;
- determine that the difference is less than an exercise offset threshold; and
- adjust the target cardiac pacing rate by decreasing the target cardiac pacing rate in response to the difference being less than the exercise offset threshold.

5. The medical device of claim 1, wherein the control circuit is further configured to:
- determine that the temperature change is an increase in temperature; and
- adjust the target cardiac pacing rate by increasing the target cardiac pacing rate in response to the temperature change being an increase.

6. The medical device of claim 1, wherein the control circuit is further configured to:
- determine a temperature from the temperature signal at a first rate for determining a second temperature change when at least one of:
  - the second activity metric is less than an activity threshold; or
  - the target cardiac pacing rate based on the second activity metric is less than a rate threshold; and
- determine the temperature from the temperature signal at a second rate for determining the second temperature change when at least one of:
  - the second activity metric is greater than or equal to the activity threshold; or
  - the target cardiac pacing rate based on the second activity metric is greater than or equal to the rate threshold, the second rate higher than the first rate.

7. The medical device of claim 1, wherein the control circuit is further configured to:
- determine the target cardiac pacing rate based on the second activity metric according to the transfer function defined by the at least one slope and the at least one set point where the at least one set point includes an upper rate set point; and
- adjust the transfer function by adjusting at least the upper rate set point.

8. The medical device of claim 7 wherein the transfer function includes a first slope and a second slope of the at least one slope of the transfer function, wherein the control circuit is further configured to:
- determine the target cardiac pacing rate based on the second activity metric according to the transfer function by determining the target cardiac pacing rate according to the first slope when the second activity metric is less than the upper rate set point;
- determine the target cardiac pacing rate according to the second slope when the second activity metric is greater than the upper rate set point; and
- adjust the upper rate set point by increasing the upper rate set point based on the temperature change.

9. The medical device of claim 8 wherein the control circuit is further configured to determine the target cardiac pacing rate based on the second activity metric according to the transfer function by determining the target cardiac pacing rate to be a maximum upper rate when the second activity metric is greater than the upper rate set point.

10. The medical device of claim 1, wherein the control circuit is further configured to:
- receive a signal transmitted by another device; and
- determine the temperature change in response to receiving the transmitted signal.

11. The medical device of claim 1, wherein the control circuit is configured to determine the temperature change by:
- determining a moving average of the temperature signal over a time interval;
- determining a current temperature from the temperature signal;
- comparing the current temperature to the moving average; and
- determining the temperature change based on the comparison.

12. The medical device of claim 1, wherein the transfer function includes a lower rate set point of the at least one set point and the control circuit is further configured to:
- determine that the first activity metric is less than or equal to the lower rate set point;
- determine that the second activity metric is increased from the lower rate set point;
- determine that the temperature change is not increasing; and
- set the target cardiac pacing rate to a pacing lower rate in response to the temperature change not increasing when the second activity metric is increased from the lower rate set point.

13. The medical device of claim 1, further comprising a sensing circuit configured to sense a cardiac electrical signal;
- wherein the control circuit is further configured to:
  - detect a tachyarrhythmia from at least one of the sensed cardiac electrical signal and the acceleration signal; and
  - determine the temperature change in response to detecting the tachyarrhythmia.

14. A method comprising:
- generating cardiac pacing pulses at a pacing rate;
- generating an acceleration signal;
- generating a temperature signal;
- storing a transfer function that relates an activity metric to a target cardiac pacing rate, the transfer function being defined by at least one slope and at least one set point;
- determining a first activity metric representative of patient physical activity from the acceleration signal;
- determining from the acceleration signal a second activity metric representative of patient physical activity at a time later than the first activity metric;
- determining the target cardiac pacing rate based on the second activity metric according to the transfer function;
- determining that the second activity metric is equal to or greater than the first activity metric;
- determining a temperature change from the temperature signal;
- in response to the second activity metric being equal to or greater than the first activity metric, determining an adjusted target cardiac pacing rate by:
  - adjusting the transfer function by adjusting at least one of the at least one slope or the least one set point based on the temperature change; and
  - determining the adjusted target cardiac pacing rate based on the second activity metric according to the adjusted transfer; and
- adjusting the pacing rate according to the adjusted target cardiac pacing rate.

15. The method of claim 14, further comprising:
determining that at least one of:
  the second activity metric is greater than or equal to an activity threshold; or
  the target cardiac pacing rate based on the second activity metric is greater than or equal to a rate threshold; and
determining the temperature change in response to the at least one of the second activity metric being greater than or equal to the activity threshold or the target cardiac pacing rate based on the second activity metric being greater than or equal to the rate threshold.

16. The method of claim 14, further comprising:
determining that the temperature change is less than a threshold change; and
withholding adjusting the transfer function in response to the temperature change being less than the threshold change when the second activity metric is greater than or equal to the first activity metric.

17. The method of claim 14, further comprising:
determining a moving average of the temperature signal;
determining a current temperature from the temperature signal;
determining a difference between the current temperature and the moving average;
determining that the difference is less than an exercise offset threshold; and
adjusting the target cardiac pacing rate by decreasing the target cardiac pacing rate in response to the difference being less than the exercise offset threshold.

18. The method of claim 14, further comprising:
determining that the temperature change is an increase in temperature; and
adjusting the target cardiac pacing rate by increasing the target cardiac pacing rate in response to the temperature change being an increase.

19. The method of claim 14, further comprising:
determining a temperature from the temperature signal at a first rate for determining a second temperature change when at least one of:
  the second activity metric is less than an activity threshold; or
  the target cardiac pacing rate based on the second activity metric is less than a rate threshold; and
determining the temperature from the temperature signal at a second rate for determining the second temperature change when at least one of:
  the second activity metric is greater than or equal to the activity threshold; or
  the target cardiac pacing rate based on the second activity metric is greater than or equal to the rate threshold, the second rate higher than the first rate.

20. The method of claim 14, further comprising:
determining the target cardiac pacing rate based on the second activity metric according to the transfer function defined by the at least one slope and the at least one set point, where the at least one set point includes an upper rate set point; and
adjusting the transfer function by adjusting at least the upper rate set point based on the temperature change.

21. The method of claim 14, further comprising:
receiving a signal transmitted by another device; and
determining the temperature change in response to receiving the transmitted signal.

22. The method of claim 14, wherein determining the temperature change comprises:
determining a moving average of the temperature signal over a time interval;
determining a current temperature from the temperature signal;
comparing the current temperature to the moving average; and
determining the temperature change based on the comparison.

23. The method of claim 14, further comprising:
storing the transfer function including a lower rate set point of the at least one set point;
determining that the first activity metric is less than or equal to the lower rate set point;
determining that the second activity metric is increased from the lower rate set point;
determining that the temperature change is not increasing; and
setting the target cardiac pacing rate to a pacing lower rate in response to the temperature change not increasing when the second activity metric is increased from the lower set point.

24. The method of claim 14, further comprising:
sensing a cardiac electrical signal;
detecting a tachyarrhythmia from at least one of the sensed cardiac electrical signal and the acceleration signal; and
determining the temperature change in response to detecting the tachyarrhythmia.

25. A non-transitory, computer-readable storage medium storing a transfer function that relates an activity metric to a target cardiac pacing rate, the transfer function being defined by at least one slope and at least one set point, and storing a set of instructions which, when executed by a control circuit of a medical device, cause the medical device to:
deliver cardiac pacing pulses at a pacing rate;
generate an acceleration signal;
generate a temperature signal;
determine a first activity metric representative of patient physical activity from the acceleration signal;
determine from the acceleration signal a second activity metric representative of patient physical activity at a time later than the first activity metric;
determine the target cardiac pacing rate based on the second activity metric according to the transfer function;
determine that the second activity metric is equal to or greater than the first activity metric and the first activity metric is greater than a first set point of the at least one set point of the transfer function;
determine a temperature change from the temperature signal; and
in response to the second activity metric being greater than or equal to the first activity metric, determine an adjusted target cardiac pacing rate based at least on the temperature change by:
  adjusting the transfer function by adjusting at least one of the at least one slope or the least one set point based on the temperature change; and
  determining the adjusted target cardiac pacing rate based on the second activity metric according to the adjusted transfer function; and
adjust the pacing rate according to the adjusted target cardiac pacing rate.

* * * * *